United States Patent
Tong et al.

(10) Patent No.: US 10,925,587 B2
(45) Date of Patent: Feb. 23, 2021

(54) ANCHOR DELIVERY SYSTEM

(71) Applicant: NeoTract, Inc., Pleasanton, CA (US)

(72) Inventors: Ling-Kang Tong, Fremont, CA (US); Joseph Catanese, III, San Leandro, CA (US); Floria Cheng, San Francisco, CA (US); Jolene Cutts, San Francisco, CA (US); Daniel Merrick, Dublin, CA (US); Theodore C. Lamson, Pleasanton, CA (US); Kristin Taylor, San Ramon, CA (US); Earl A. Bright, II, Los Altos, CA (US); Michael Gearhart, Fremont, CA (US); Matthew McLean, San Francisco, CA (US); James Niederjohn, San Jose, CA (US); Brian Y. Tachibana, Oakland, CA (US); Andrew L. Johnston, Redwood City, CA (US); John Stiggelbout, Sausalito, CA (US)

(73) Assignee: NeoTract, Inc., Pleasanton, CA (US)

( * ) Notice: Subject to any disclaimer, the term of this patent is extended or adjusted under 35 U.S.C. 154(b) by 198 days.

(21) Appl. No.: 15/974,899

(22) Filed: May 9, 2018

(65) Prior Publication Data
US 2018/0256142 A1    Sep. 13, 2018

Related U.S. Application Data

(60) Continuation of application No. 13/830,684, filed on Mar. 14, 2013, now abandoned, which is a
(Continued)

(51) Int. Cl.
*A61B 17/00* (2006.01)
*A61B 17/04* (2006.01)
(Continued)

(52) U.S. Cl.
CPC .... *A61B 17/00234* (2013.01); *A61B 17/0401* (2013.01); *A61B 17/0469* (2013.01);
(Continued)

(58) Field of Classification Search
CPC .......... A61B 17/00234; A61B 17/0218; A61B 17/3486; A61B 2017/00274;
(Continued)

(56) References Cited

U.S. PATENT DOCUMENTS

| 659,422 A | 10/1900 | Shidler |
| 780,392 A | 1/1905 | Wanamaker et al. |

(Continued)

FOREIGN PATENT DOCUMENTS

| CA | 2477220 | 11/2007 |
| CN | 1697633 A | 11/2005 |

(Continued)

OTHER PUBLICATIONS

Bacharova, O.A., et al. "The Effect of Rhodiolae rosea Extract on Incidence Rate of Superficial Bladder Carcinoma Relapses", Kozin 1995.

(Continued)

*Primary Examiner* — Gregory A Anderson
(74) *Attorney, Agent, or Firm* — Christopher J. Buchko

(57) ABSTRACT

A system and associated method for manipulating tissues and anatomical or other structures in medical applications for the purpose of treating diseases or disorders or other purposes. In one aspect, the system includes a delivery device configured to deploy and implant anchor devices for such purposes.

9 Claims, 47 Drawing Sheets

Related U.S. Application Data continuation-in-part of application No. 13/692,876, filed on Dec. 3, 2012, now Pat. No. 8,939,996, which is a continuation-in-part of application No. 12/852,243, filed on Aug. 6, 2010, now Pat. No. 8,333,776, which is a continuation-in-part of application No. 12/512,674, filed on Jul. 30, 2009, now Pat. No. 8,216,254, and a continuation-in-part of application No. 11/775,162, filed on Jul. 9, 2007, now Pat. No. 8,945,152, and a continuation-in-part of application No. 11/671,914, filed on Feb. 6, 2007, now Pat. No. 8,157,815, and a continuation-in-part of application No. 11/492,690, filed on Jul. 24, 2006, now Pat. No. 7,896,891, which is a continuation-in-part of application No. 11/318,246, filed on Dec. 22, 2005, now Pat. No. 7,645,286, and a continuation-in-part of application No. 11/134,870, filed on May 20, 2005, now Pat. No. 7,758,594, said application No. 12/852,243 is a continuation-in-part of application No. 11/838,036, filed on Aug. 13, 2007, now Pat. No. 7,914,542, which is a division of application No. 11/134,870, filed on May 20, 2005, now Pat. No. 7,758,594, said application No. 12/852,243 is a continuation-in-part of application No. 11/833,660, filed on Aug. 3, 2007, now Pat. No. 8,940,001, which is a division of application No. 11/318,246, filed on Dec. 22, 2005, now Pat. No. 7,645,286, and a continuation-in-part of application No. 11/134,870, filed on May 20, 2005, now Pat. No. 7,758,594.

(60) Provisional application No. 61/084,937, filed on Jul. 30, 2008.

(51) Int. Cl.
  *A61B 17/32* (2006.01)
  *A61B 17/34* (2006.01)
  *A61B 17/42* (2006.01)
  *A61B 17/06* (2006.01)
  *A61B 17/29* (2006.01)
  *A61B 18/00* (2006.01)

(52) U.S. Cl.
  CPC .......... *A61B 17/0482* (2013.01); *A61B 17/32* (2013.01); *A61B 17/3468* (2013.01); *A61B 17/3478* (2013.01); *A61B 17/42* (2013.01); *A61B 2017/00022* (2013.01); *A61B 2017/0046* (2013.01); *A61B 2017/00274* (2013.01); *A61B 2017/00792* (2013.01); *A61B 2017/00796* (2013.01); *A61B 2017/00805* (2013.01); *A61B 2017/0409* (2013.01); *A61B 2017/0417* (2013.01); *A61B 2017/0419* (2013.01); *A61B 2017/0464* (2013.01); *A61B 2017/0479* (2013.01); *A61B 2017/0488* (2013.01); *A61B 2017/06052* (2013.01); *A61B 2017/06095* (2013.01); *A61B 2017/2923* (2013.01); *A61B 2018/00547* (2013.01)

(58) Field of Classification Search
  CPC .... A61B 2017/0409; A61B 2017/0417; A61B 2017/0419; A61B 2017/0464; A61B 2017/0488; A61B 2018/00547
  See application file for complete search history.

(56) References Cited

U.S. PATENT DOCUMENTS

| | | |
|---|---|---|
| 789,467 A | 5/1905 | West |
| 2,360,164 A | 10/1944 | Frank |
| 2,485,531 A | 10/1949 | William et al. |
| 2,579,192 A | 12/1951 | Alexander |
| 2,646,298 A | 7/1953 | Leary |
| 2,697,624 A | 12/1954 | Thomas et al. |
| 2,734,299 A | 2/1956 | Masson |
| 2,825,592 A | 3/1958 | Mckenzie |
| 3,326,586 A | 6/1967 | Frost et al. |
| 3,470,834 A | 10/1969 | Bone |
| 3,521,918 A | 7/1970 | Hammond |
| 3,541,591 A | 11/1970 | Hoegerman |
| 3,664,345 A | 5/1972 | Dabbs et al. |
| 3,713,680 A | 1/1973 | Pagano |
| 3,716,058 A | 2/1973 | Tanner |
| 3,756,638 A | 9/1973 | Stockberger |
| 3,873,140 A | 3/1975 | Bloch |
| 3,875,648 A | 4/1975 | Bone |
| 3,886,933 A | 6/1975 | Mori et al. |
| 3,931,667 A | 1/1976 | Merser et al. |
| 3,976,079 A | 8/1976 | Samuels et al. |
| 4,006,747 A | 2/1977 | Kronenthal et al. |
| 4,137,920 A | 2/1979 | Bonnet |
| 4,164,225 A | 8/1979 | Johnson et al. |
| 4,210,148 A | 7/1980 | Stivala |
| 4,235,238 A * | 11/1980 | Ogiu ............... A61B 17/04 606/145 |
| 4,291,698 A | 9/1981 | Fuchs et al. |
| 4,409,974 A | 10/1983 | Freedland |
| 4,419,094 A | 12/1983 | Patel |
| 4,452,236 A * | 6/1984 | Utsugi ............ A61M 25/0147 600/107 |
| 4,493,323 A | 1/1985 | Albright et al. |
| 4,513,746 A | 4/1985 | Aranyi et al. |
| 4,621,640 A | 11/1986 | Mulhollan et al. |
| 4,655,771 A | 4/1987 | Wallsten |
| 4,657,461 A | 4/1987 | Smith |
| 4,669,473 A | 6/1987 | Richards et al. |
| 4,705,040 A | 11/1987 | Mueller et al. |
| 4,714,281 A | 12/1987 | Peck |
| 4,738,255 A | 4/1988 | Goble et al. |
| 4,741,330 A | 5/1988 | Hayhurst |
| 4,744,364 A | 5/1988 | Kensey |
| 4,750,492 A | 6/1988 | Jacobs |
| 4,762,128 A | 8/1988 | Rosenbluth |
| 4,823,794 A | 4/1989 | Pierce |
| 4,863,439 A | 9/1989 | Sanderson |
| 4,893,623 A | 1/1990 | Rosenbluth |
| 4,899,743 A | 2/1990 | Nicholson et al. |
| 4,926,860 A | 5/1990 | Stice et al. |
| 4,935,028 A | 6/1990 | Drews |
| 4,946,468 A | 8/1990 | Li |
| 4,955,859 A | 9/1990 | Zilber |
| 4,955,913 A | 9/1990 | Robinson |
| 4,968,315 A | 11/1990 | Gatturna |
| 4,994,066 A | 2/1991 | Voss |
| 5,002,550 A | 3/1991 | Li |
| 5,019,032 A | 5/1991 | Robertson |
| 5,041,129 A | 8/1991 | Hayhurst et al. |
| 5,046,513 A | 9/1991 | Gatturna et al. |
| 5,053,046 A | 10/1991 | Janese |
| 5,078,731 A | 1/1992 | Hayhurst |
| 5,080,660 A | 1/1992 | Buelna |
| 5,098,374 A | 3/1992 | Othel-Jacobsen et al. |
| 5,100,421 A | 3/1992 | Christoudias |
| 5,123,914 A | 6/1992 | Cope |
| 5,127,393 A | 7/1992 | McFarlin et al. |
| 5,129,912 A | 7/1992 | Noda et al. |
| 5,133,713 A | 7/1992 | Huang et al. |
| 5,159,925 A | 11/1992 | Neuwirth et al. |
| 5,160,339 A | 11/1992 | Chen et al. |
| 5,163,960 A | 11/1992 | Bonutti |
| 5,167,614 A | 12/1992 | Tessmann et al. |
| 5,192,303 A | 3/1993 | Gatturna et al. |
| 5,203,787 A | 4/1993 | Noblitt et al. |
| 5,207,672 A | 5/1993 | Roth et al. |
| 5,217,470 A | 6/1993 | Weston |
| 5,217,486 A | 6/1993 | Rice et al. |
| 5,234,454 A | 8/1993 | Bangs |
| 5,236,445 A | 8/1993 | Hayhurst et al. |
| 5,237,984 A | 8/1993 | Williams et al. |

(56) References Cited

U.S. PATENT DOCUMENTS

| | | |
|---|---|---|
| 5,254,126 A | 10/1993 | Filipi et al. |
| 5,258,015 A | 11/1993 | Li et al. |
| 5,267,960 A | 12/1993 | Hayman et al. |
| 5,269,802 A | 12/1993 | Garber |
| 5,269,809 A | 12/1993 | Hayhurst et al. |
| 5,300,099 A | 4/1994 | Rudie |
| 5,306,280 A | 4/1994 | Bregen et al. |
| 5,322,501 A | 6/1994 | Mahmud-Durrani |
| 5,330,488 A | 7/1994 | Goldrath |
| 5,334,200 A | 8/1994 | Johnson |
| 5,336,240 A | 8/1994 | Metzler et al. |
| 5,350,399 A | 9/1994 | Erlebacher et al. |
| 5,354,271 A | 10/1994 | Voda |
| 5,358,511 A | 10/1994 | Gatturna et al. |
| 5,364,408 A | 11/1994 | Gordon |
| 5,366,490 A | 11/1994 | Edwards et al. |
| 5,368,599 A | 11/1994 | Hirsch et al. |
| 5,370,646 A | 12/1994 | Reese et al. |
| 5,370,661 A | 12/1994 | Branch |
| 5,372,600 A | 12/1994 | Beyar et al. |
| 5,380,334 A | 1/1995 | Torrie et al. |
| 5,391,182 A | 2/1995 | Chin |
| 5,403,348 A | 4/1995 | Bonutti |
| 5,405,352 A | 4/1995 | Weston |
| 5,409,453 A | 4/1995 | Lundquist et al. |
| 5,411,520 A | 5/1995 | Nash et al. |
| 5,417,691 A | 5/1995 | Hayhurst |
| 5,435,805 A | 7/1995 | Edwards et al. |
| 5,458,612 A | 10/1995 | Chin |
| 5,464,416 A | 11/1995 | Steckel |
| 5,470,308 A * | 11/1995 | Edwards ............ A61B 10/0233 604/22 |
| 5,470,337 A | 11/1995 | Moss |
| 5,472,446 A | 12/1995 | Torre |
| 5,480,406 A | 1/1996 | Nolan et al. |
| 5,499,994 A | 3/1996 | Tihon et al. |
| 5,501,690 A | 3/1996 | Measamer et al. |
| 5,507,754 A | 4/1996 | Green et al. |
| 5,522,846 A | 6/1996 | Bonutti |
| 5,531,759 A | 7/1996 | Kensey et al. |
| 5,531,763 A | 7/1996 | Mastri et al. |
| 5,534,012 A | 7/1996 | Bonutti |
| 5,536,240 A | 7/1996 | Edwards et al. |
| 5,540,655 A | 7/1996 | Edwards et al. |
| 5,540,704 A | 7/1996 | Gordon et al. |
| 5,542,594 A | 8/1996 | McKean et al. |
| 5,545,171 A | 8/1996 | Sharkey et al. |
| 5,545,178 A | 8/1996 | Kensey et al. |
| 5,549,631 A | 8/1996 | Bonutti |
| 5,550,172 A | 8/1996 | Regula et al. |
| 5,554,162 A | 9/1996 | DeLange |
| 5,554,171 A | 9/1996 | Gatturna et al. |
| 5,562,688 A | 10/1996 | Riza |
| 5,562,689 A | 10/1996 | Green et al. |
| 5,569,305 A | 10/1996 | Bonutti |
| 5,571,104 A | 11/1996 | Li |
| 5,573,540 A | 11/1996 | Yoon |
| 5,578,044 A | 11/1996 | Gordon et al. |
| 5,591,177 A | 1/1997 | Lehrer |
| 5,591,179 A | 1/1997 | Edelstein |
| 5,593,421 A | 1/1997 | Bauer |
| 5,611,515 A | 3/1997 | Benderev et al. |
| 5,620,461 A | 4/1997 | Moer et al. |
| 5,626,614 A | 5/1997 | Hart |
| 5,630,824 A | 5/1997 | Hart |
| 5,643,321 A | 7/1997 | McDevitt |
| 5,647,836 A | 7/1997 | Blake et al. |
| 5,653,373 A | 8/1997 | Green et al. |
| 5,665,109 A | 9/1997 | Yoon |
| 5,667,486 A | 9/1997 | Mikulich et al. |
| 5,667,488 A | 9/1997 | Lundquist et al. |
| 5,667,522 A | 9/1997 | Flomenblit et al. |
| 5,669,917 A | 9/1997 | Sauer et al. |
| 5,672,171 A | 9/1997 | Andrus et al. |
| 5,690,649 A | 11/1997 | Li |
| 5,690,677 A | 11/1997 | Schmieding et al. |
| 5,697,950 A | 12/1997 | Fucci et al. |
| 5,707,394 A | 1/1998 | Miller et al. |
| 5,716,368 A | 2/1998 | Torre et al. |
| 5,718,717 A | 2/1998 | Bonutti |
| 5,725,556 A | 3/1998 | Moser et al. |
| 5,725,557 A | 3/1998 | Gatturna et al. |
| 5,733,306 A | 3/1998 | Bonutti |
| 5,741,276 A | 4/1998 | Poloyko et al. |
| 5,746,753 A | 5/1998 | Sullivan et al. |
| 5,749,846 A | 5/1998 | Edwards et al. |
| 5,749,889 A | 5/1998 | Bacich et al. |
| 5,752,963 A | 5/1998 | Allard et al. |
| 5,775,328 A | 7/1998 | Lowe et al. |
| 5,782,862 A | 7/1998 | Bonutti |
| 5,782,864 A | 7/1998 | Lizardi |
| 5,791,022 A | 8/1998 | Bohman |
| 5,800,445 A | 9/1998 | Ratcliff et al. |
| 5,807,403 A | 9/1998 | Beyar et al. |
| 5,810,848 A | 9/1998 | Hayhurst |
| 5,810,853 A | 9/1998 | Yoon |
| 5,814,072 A | 9/1998 | Bonutti |
| 5,830,179 A | 11/1998 | Mikus et al. |
| 5,830,221 A | 11/1998 | Stein et al. |
| 5,845,645 A | 12/1998 | Bonutti |
| 5,846,254 A | 12/1998 | Schulze et al. |
| 5,861,002 A | 1/1999 | Desai |
| 5,868,762 A | 2/1999 | Cragg et al. |
| 5,873,891 A | 2/1999 | Sohn |
| 5,879,357 A | 3/1999 | Heaton et al. |
| 5,897,574 A | 4/1999 | Bonutti |
| 5,899,911 A | 5/1999 | Carter |
| 5,899,921 A | 5/1999 | Caspari et al. |
| 5,904,679 A | 5/1999 | Clayman |
| 5,904,696 A | 5/1999 | Rosenman |
| 5,908,428 A | 6/1999 | Scirica et al. |
| 5,908,447 A | 6/1999 | Schroeppel et al. |
| 5,919,198 A | 7/1999 | Graves et al. |
| 5,919,202 A | 7/1999 | Yoon |
| 5,921,982 A | 7/1999 | Lesh et al. |
| 5,921,986 A | 7/1999 | Bonutti |
| 5,928,252 A | 7/1999 | Steadman et al. |
| 5,931,844 A | 8/1999 | Thompson et al. |
| 5,941,439 A | 8/1999 | Kammerer et al. |
| 5,944,739 A | 8/1999 | Zlock et al. |
| 5,948,000 A | 9/1999 | Larsen et al. |
| 5,948,001 A | 9/1999 | Larsen |
| 5,948,002 A | 9/1999 | Bonutti |
| 5,954,057 A | 9/1999 | Li |
| 5,954,747 A | 9/1999 | Clark |
| 5,964,732 A | 10/1999 | Willard |
| 5,971,447 A | 10/1999 | Steck |
| 5,971,967 A | 10/1999 | Willard |
| 6,010,514 A | 1/2000 | Burney et al. |
| 6,011,525 A | 1/2000 | Piole |
| 6,015,428 A | 1/2000 | Pagedas |
| 6,024,751 A | 2/2000 | Lovato et al. |
| 6,030,393 A | 2/2000 | Corlew |
| 6,033,413 A | 3/2000 | Mikus et al. |
| 6,033,430 A | 3/2000 | Bonutti |
| 6,036,701 A | 3/2000 | Rosenman |
| 6,048,351 A | 4/2000 | Gordon et al. |
| 6,053,908 A | 4/2000 | Crainich et al. |
| 6,053,935 A | 4/2000 | Brenneman et al. |
| 6,056,722 A | 5/2000 | Jayaraman |
| 6,056,772 A | 5/2000 | Bonutti |
| 6,066,160 A | 5/2000 | Colvin et al. |
| 6,068,648 A | 5/2000 | Cole et al. |
| 6,080,167 A | 6/2000 | Lyell |
| 6,086,608 A | 7/2000 | Ek et al. |
| 6,110,183 A | 8/2000 | Cope |
| 6,117,133 A | 9/2000 | Zappala |
| 6,117,160 A | 9/2000 | Bonutti |
| 6,117,161 A | 9/2000 | Li et al. |
| 6,120,539 A | 9/2000 | Eldridge et al. |
| 6,132,438 A | 10/2000 | Fleischman et al. |
| 6,139,555 A | 10/2000 | Hart et al. |
| RE36,974 E | 11/2000 | Bonutti |
| 6,143,006 A | 11/2000 | Chan |

(56) References Cited

U.S. PATENT DOCUMENTS

| | | |
|---|---|---|
| 6,152,935 A | 11/2000 | Kammerer et al. |
| 6,156,044 A | 12/2000 | Kammerer et al. |
| 6,156,049 A | 12/2000 | Lovato et al. |
| 6,159,207 A | 12/2000 | Yoon |
| 6,159,234 A | 12/2000 | Bonutti et al. |
| 6,193,714 B1 | 2/2001 | McGaffigan et al. |
| 6,200,329 B1 | 3/2001 | Fung et al. |
| 6,203,565 B1 | 3/2001 | Bonutti et al. |
| 6,206,895 B1 | 3/2001 | Levinson |
| 6,206,907 B1 | 3/2001 | Marino et al. |
| 6,228,096 B1 | 5/2001 | Marchand |
| 6,235,024 B1 | 5/2001 | Tu |
| 6,258,124 B1 | 7/2001 | Darois et al. |
| 6,261,302 B1 | 7/2001 | Voegele et al. |
| 6,261,320 B1 | 7/2001 | Tam et al. |
| 6,270,530 B1 | 8/2001 | Eldridge et al. |
| 6,280,441 B1 | 8/2001 | Ryan |
| 6,280,460 B1 | 8/2001 | Bolduc et al. |
| 6,287,317 B1 | 9/2001 | Makower et al. |
| 6,290,711 B1 | 9/2001 | Caspari et al. |
| 6,306,158 B1 | 10/2001 | Bartlett |
| 6,312,448 B1 | 11/2001 | Bonutti |
| 6,319,263 B1 | 11/2001 | Levinson |
| 6,322,112 B1 | 11/2001 | Duncan |
| 6,332,889 B1 | 12/2001 | Sancoff et al. |
| 6,382,214 B1 | 5/2002 | Raz et al. |
| 6,387,041 B1 | 5/2002 | Harari et al. |
| 6,398,795 B1 | 6/2002 | McAlister et al. |
| 6,398,796 B2 | 6/2002 | Levinson |
| 6,425,900 B1 | 7/2002 | Knodel et al. |
| 6,425,919 B1 | 7/2002 | Lambrecht |
| 6,428,538 B1 | 8/2002 | Blewett et al. |
| 6,428,562 B2 | 8/2002 | Bonutti |
| 6,436,107 B1 | 8/2002 | Wang et al. |
| 6,461,355 B2 | 10/2002 | Svejkovsky et al. |
| 6,482,235 B1 | 11/2002 | Lambrecht et al. |
| 6,488,691 B1 | 12/2002 | Carroll et al. |
| 6,491,672 B2 | 12/2002 | Slepian et al. |
| 6,491,707 B2 | 12/2002 | Makower et al. |
| 6,494,888 B1 | 12/2002 | Laufer et al. |
| 6,500,184 B1 | 12/2002 | Chan et al. |
| 6,500,195 B2 | 12/2002 | Bonutti |
| 6,506,190 B1 | 1/2003 | Walshe |
| 6,506,196 B1 | 1/2003 | Laufer |
| 6,514,247 B1 | 2/2003 | McGaffigan et al. |
| 6,517,569 B2 | 2/2003 | Mikus et al. |
| 6,527,702 B2 | 3/2003 | Whalen et al. |
| 6,527,794 B1 | 3/2003 | McDevitt et al. |
| 6,530,932 B1 | 3/2003 | Swayze et al. |
| 6,533,796 B1 | 3/2003 | Sauer et al. |
| 6,544,230 B1 | 4/2003 | Flaherty et al. |
| 6,547,725 B1 | 4/2003 | Paolitto et al. |
| 6,551,328 B2 | 4/2003 | Kortenbach |
| 6,551,333 B2 | 4/2003 | Kuhns et al. |
| 6,565,578 B1 | 5/2003 | Peifer et al. |
| 6,569,187 B1 | 5/2003 | Bonutti et al. |
| 6,572,626 B1 | 6/2003 | Knodel et al. |
| 6,572,635 B1 | 6/2003 | Bonutti |
| 6,572,653 B1 | 6/2003 | Simonson |
| 6,582,453 B1 | 6/2003 | Tran et al. |
| 6,592,609 B1 | 7/2003 | Bonutti |
| 6,595,911 B2 | 7/2003 | LoVuolo |
| 6,596,013 B2 | 7/2003 | Yang et al. |
| 6,599,311 B1 | 7/2003 | Biggs et al. |
| 6,626,913 B1 | 9/2003 | McKinnon et al. |
| 6,626,916 B1 | 9/2003 | Yeung et al. |
| 6,626,919 B1 | 9/2003 | Swanstrom |
| 6,629,534 B1 | 10/2003 | Goar et al. |
| 6,638,275 B1 | 10/2003 | McGaffigan et al. |
| 6,641,524 B2 | 11/2003 | Kovac |
| 6,641,592 B1 | 11/2003 | Sauer et al. |
| 6,656,182 B1 | 12/2003 | Hayhurst |
| 6,660,008 B1 | 12/2003 | Foerster et al. |
| 6,660,023 B2 | 12/2003 | McDevitt et al. |
| 6,663,589 B1 | 12/2003 | Halevy |
| 6,663,633 B1 | 12/2003 | Pierson |
| 6,663,639 B1 | 12/2003 | Laufer et al. |
| 6,699,263 B2 | 3/2004 | Cope |
| 6,702,846 B2 | 3/2004 | Mikus et al. |
| 6,706,047 B2 | 3/2004 | Trout et al. |
| 6,709,493 B2 | 3/2004 | DeGuiseppi et al. |
| 6,715,804 B2 | 4/2004 | Beers |
| 6,719,709 B2 | 4/2004 | Whalen et al. |
| 6,730,112 B2 | 5/2004 | Levinson |
| 6,736,823 B2 | 5/2004 | Darois et al. |
| 6,736,854 B2 | 5/2004 | Vadurro et al. |
| 6,740,098 B2 | 5/2004 | Abrams et al. |
| 6,767,037 B2 | 7/2004 | Wenstrom |
| 6,770,076 B2 | 8/2004 | Foerster |
| 6,773,438 B1 | 8/2004 | Knodel et al. |
| 6,773,441 B1 | 8/2004 | Laufer et al. |
| 6,790,213 B2 | 9/2004 | Cherok et al. |
| 6,790,223 B2 | 9/2004 | Reever |
| 6,802,838 B2 | 10/2004 | Loeb et al. |
| 6,802,846 B2 | 10/2004 | Hauschild et al. |
| 6,821,282 B2 | 11/2004 | Perry et al. |
| 6,821,285 B2 | 11/2004 | Laufer et al. |
| 6,821,291 B2 | 11/2004 | Bolea et al. |
| 6,835,200 B2 | 12/2004 | Laufer et al. |
| 6,905,475 B2 | 6/2005 | Hauschild et al. |
| 6,908,473 B2 | 6/2005 | Skiba et al. |
| 6,921,361 B2 | 7/2005 | Suzuki et al. |
| 6,926,732 B2 | 8/2005 | Derus et al. |
| 6,951,565 B2 | 10/2005 | Keane et al. |
| 6,986,775 B2 | 1/2006 | Morales et al. |
| 6,986,784 B1 | 1/2006 | Weiser et al. |
| 6,988,983 B2 | 1/2006 | Connors et al. |
| 6,991,596 B2 | 1/2006 | Whalen et al. |
| 6,991,647 B2 | 1/2006 | Jadhav |
| 6,997,940 B2 | 2/2006 | Bonutti |
| 7,001,327 B2 | 2/2006 | Whalen et al. |
| 7,004,965 B2 | 2/2006 | Gross |
| 7,008,381 B2 | 3/2006 | Janssens |
| 7,011,688 B2 | 3/2006 | Gryska et al. |
| 7,015,253 B2 | 3/2006 | Escandon et al. |
| 7,041,111 B2 | 5/2006 | Chu |
| 7,048,698 B2 | 5/2006 | Whalen et al. |
| 7,048,747 B2 | 5/2006 | Arcia et al. |
| 7,060,077 B2 | 6/2006 | Gordon et al. |
| 7,063,715 B2 | 6/2006 | Onuki et al. |
| 7,065,325 B2 | 6/2006 | Zegelin et al. |
| 7,081,126 B2 | 7/2006 | McDevitt et al. |
| 7,083,638 B2 | 8/2006 | Foerster |
| 7,087,073 B2 | 8/2006 | Bonutti |
| 7,089,064 B2 | 8/2006 | Manker et al. |
| 7,090,690 B2 | 8/2006 | Foerster et al. |
| 7,093,601 B2 | 8/2006 | Manker et al. |
| 7,096,301 B2 | 8/2006 | Beaudoin et al. |
| 7,104,949 B2 | 9/2006 | Anderson et al. |
| 7,105,004 B2 | 9/2006 | DiCesare et al. |
| 7,108,655 B2 | 9/2006 | Whalen et al. |
| 7,112,226 B2 | 9/2006 | Gellman |
| 7,141,038 B2 | 11/2006 | Whalen et al. |
| 7,153,314 B2 | 12/2006 | Laufer et al. |
| 7,179,225 B2 | 2/2007 | Shluzas et al. |
| 7,226,558 B2 | 6/2007 | Nieman et al. |
| 7,232,448 B2 | 6/2007 | Battles et al. |
| 7,255,675 B2 | 8/2007 | Gertner et al. |
| 7,261,709 B2 | 8/2007 | Swoyer et al. |
| 7,261,710 B2 | 8/2007 | Elmouelhi et al. |
| 7,282,020 B2 | 10/2007 | Kaplan |
| 7,288,063 B2 | 10/2007 | Petros et al. |
| 7,303,108 B2 | 12/2007 | Shelton |
| 7,320,701 B2 | 1/2008 | Haut et al. |
| 7,322,974 B2 | 1/2008 | Swoyer et al. |
| 7,326,221 B2 | 2/2008 | Sakamoto et al. |
| 7,334,822 B1 | 2/2008 | Hines |
| 7,335,197 B2 | 2/2008 | Sage et al. |
| 7,340,300 B2 | 3/2008 | Christopherson et al. |
| 7,399,304 B2 | 7/2008 | Gambale et al. |
| 7,402,166 B2 | 7/2008 | Feigl |
| 7,416,554 B2 | 8/2008 | Lam et al. |
| 7,417,175 B2 | 8/2008 | Oda et al. |
| 7,437,194 B2 | 10/2008 | Skwarek et al. |

(56) References Cited

U.S. PATENT DOCUMENTS

| | | |
|---|---|---|
| 7,463,934 B2 | 12/2008 | Tronnes et al. |
| 7,470,228 B2 | 12/2008 | Connors et al. |
| 7,481,771 B2 | 1/2009 | Fonseca et al. |
| 7,485,124 B2 | 2/2009 | Kuhns et al. |
| 7,553,317 B2 | 6/2009 | William et al. |
| 7,608,108 B2 | 10/2009 | Bhatnagar et al. |
| 7,632,297 B2 | 12/2009 | Gross |
| 7,645,286 B2 | 1/2010 | Catanese et al. |
| 7,658,311 B2 | 2/2010 | Boudreaux |
| 7,666,197 B2 | 2/2010 | Orban |
| 7,674,275 B2 | 3/2010 | Martin et al. |
| 7,682,374 B2 | 3/2010 | Foerster et al. |
| 7,695,494 B2 | 4/2010 | Foerster |
| 7,704,261 B2 | 4/2010 | Sakamoto et al. |
| 7,727,248 B2 | 6/2010 | Smith et al. |
| 7,731,725 B2 | 6/2010 | Gadberry et al. |
| 7,736,374 B2 | 6/2010 | Vaughan et al. |
| 7,758,594 B2 | 7/2010 | Lamson et al. |
| 7,766,923 B2 | 8/2010 | Catanese et al. |
| 7,766,939 B2 | 8/2010 | Yeung et al. |
| 7,780,682 B2 | 8/2010 | Catanese et al. |
| 7,815,655 B2 | 10/2010 | Catanese et al. |
| 7,850,712 B2 | 12/2010 | Conlon et al. |
| 7,862,584 B2 | 1/2011 | Lyons et al. |
| 7,887,551 B2 | 2/2011 | Bojarski et al. |
| 7,896,891 B2 | 3/2011 | Catanese et al. |
| 7,905,889 B2 | 3/2011 | Catanese et al. |
| 7,905,904 B2 | 3/2011 | Stone et al. |
| 7,909,836 B2 | 3/2011 | McLean et al. |
| 7,914,542 B2 | 3/2011 | Lamson et al. |
| 7,922,645 B2 | 4/2011 | Kaplan |
| 7,951,158 B2 | 5/2011 | Catanese et al. |
| 8,007,503 B2 | 8/2011 | Catanese et al. |
| 8,043,309 B2 | 10/2011 | Catanese et al. |
| 8,114,070 B2 | 2/2012 | Rubinsky et al. |
| 8,145,321 B2 | 3/2012 | Gross |
| 8,152,804 B2 | 4/2012 | Elmouelhi et al. |
| 8,157,815 B2 | 4/2012 | Catanese et al. |
| 8,162,960 B2 | 4/2012 | Manzo |
| 8,167,830 B2 | 5/2012 | Noriega |
| 8,211,118 B2 | 7/2012 | Catanese et al. |
| 8,216,254 B2 | 7/2012 | McLean et al. |
| 8,236,011 B2 | 8/2012 | Harris et al. |
| 8,251,985 B2 | 8/2012 | Hoey et al. |
| 8,273,079 B2 | 9/2012 | Hoey et al. |
| 8,298,132 B2 | 10/2012 | Connors et al. |
| 8,303,604 B2 | 11/2012 | Stone et al. |
| 8,308,765 B2 | 11/2012 | Saadat et al. |
| 8,333,776 B2 | 12/2012 | Cheng et al. |
| 8,343,187 B2 | 1/2013 | Lamson et al. |
| 8,361,112 B2 | 1/2013 | Kempton et al. |
| 8,372,065 B2 | 2/2013 | Hoey et al. |
| 8,388,611 B2 | 3/2013 | Shadduck et al. |
| 8,388,653 B2 | 3/2013 | Nobis et al. |
| 8,394,110 B2 | 3/2013 | Catanese et al. |
| 8,394,113 B2 | 3/2013 | Wei et al. |
| 8,419,723 B2 | 4/2013 | Shadduck et al. |
| 8,425,535 B2 | 4/2013 | McLean et al. |
| 8,444,657 B2 | 5/2013 | Saadat et al. |
| 8,454,655 B2 | 6/2013 | Yeung et al. |
| 8,465,551 B1 | 6/2013 | Wijay et al. |
| 8,480,686 B2 | 7/2013 | Bakos et al. |
| 8,491,606 B2 | 7/2013 | Tong et al. |
| 8,496,684 B2 | 7/2013 | Crainich et al. |
| 8,521,257 B2 | 8/2013 | Whitcomb et al. |
| 8,529,584 B2 | 9/2013 | Catanese et al. |
| 8,529,588 B2 | 9/2013 | Ahlberg et al. |
| 8,562,646 B2 | 10/2013 | Gellman et al. |
| 8,585,692 B2 | 11/2013 | Shadduck et al. |
| 8,603,106 B2 | 12/2013 | Catanese et al. |
| 8,603,123 B2 | 12/2013 | Todd |
| 8,603,187 B2 | 12/2013 | Kilemnick et al. |
| 8,628,542 B2 | 1/2014 | Merrick et al. |
| 8,663,243 B2 | 3/2014 | Lamson et al. |
| 8,668,705 B2 | 3/2014 | Johnston et al. |
| 8,683,895 B2 | 4/2014 | Nash |
| 8,715,239 B2 | 5/2014 | Lamson et al. |
| 8,715,298 B2 | 5/2014 | Catanese et al. |
| 8,734,469 B2 | 5/2014 | Pribanic et al. |
| 8,790,356 B2 | 7/2014 | Darois et al. |
| 8,801,702 B2 | 8/2014 | Hoey et al. |
| 8,808,363 B2 | 8/2014 | Perry et al. |
| 8,814,856 B2 | 8/2014 | Elmouelhi et al. |
| 8,828,035 B2 | 9/2014 | Kim |
| 8,834,458 B2 | 9/2014 | Neuberger et al. |
| 8,880,195 B2 | 11/2014 | Azure |
| 8,900,293 B2 | 12/2014 | Forbes et al. |
| 8,920,437 B2 | 12/2014 | Harris et al. |
| 8,926,494 B1 | 1/2015 | Cook et al. |
| 8,945,114 B2 | 2/2015 | Elmouelhi et al. |
| 9,034,001 B2 | 5/2015 | Cheng et al. |
| 9,039,740 B2 | 5/2015 | Wales et al. |
| 9,089,320 B2 | 7/2015 | Spivey et al. |
| 9,150,817 B2 | 10/2015 | Furihata et al. |
| 9,179,991 B2 | 11/2015 | Gozzi et al. |
| 9,204,922 B2 | 12/2015 | Hooven |
| 9,211,155 B2 | 12/2015 | Fruland et al. |
| 9,220,874 B2 | 12/2015 | Pillai et al. |
| 9,272,140 B2 | 3/2016 | Gerber |
| 9,277,914 B2 | 3/2016 | Wales et al. |
| 9,345,507 B2 | 5/2016 | Hoey et al. |
| 9,345,867 B2 | 5/2016 | Browning |
| 9,393,007 B2 | 7/2016 | Darois et al. |
| 9,439,643 B2 | 9/2016 | Darois et al. |
| 9,459,751 B2 | 10/2016 | Weaver et al. |
| 9,526,555 B2 | 12/2016 | Hoey et al. |
| 9,561,025 B2 | 2/2017 | Stone et al. |
| 9,592,044 B2 | 3/2017 | Weir et al. |
| 9,597,145 B2 | 3/2017 | Nelson et al. |
| 9,668,803 B2 | 6/2017 | Bhushan et al. |
| 9,675,373 B2 | 6/2017 | Todd |
| 9,750,492 B2 | 9/2017 | Ziniti et al. |
| 2001/0041916 A1 | 11/2001 | Bonutti |
| 2001/0044639 A1 | 11/2001 | Levinson |
| 2002/0049453 A1 | 4/2002 | Nobles et al. |
| 2002/0095064 A1 | 7/2002 | Beyar |
| 2002/0095154 A1 | 7/2002 | Atkinson et al. |
| 2002/0107540 A1 | 8/2002 | Whalen et al. |
| 2002/0128684 A1 | 9/2002 | Foerster |
| 2002/0161382 A1 | 10/2002 | Neisz et al. |
| 2002/0177866 A1 | 11/2002 | Weikel et al. |
| 2002/0183740 A1 | 12/2002 | Edwards et al. |
| 2002/0193809 A1 | 12/2002 | Meade et al. |
| 2003/0023248 A1 | 1/2003 | Parodi |
| 2003/0040803 A1 | 2/2003 | Rioux et al. |
| 2003/0060819 A1 | 3/2003 | McGovern et al. |
| 2003/0078601 A1 | 4/2003 | Shikhman et al. |
| 2003/0109769 A1 | 6/2003 | Lowery et al. |
| 2003/0120309 A1 | 6/2003 | Colleran et al. |
| 2003/0130575 A1 | 7/2003 | Desai |
| 2003/0144570 A1 | 7/2003 | Hunter et al. |
| 2003/0176883 A1 | 9/2003 | Sauer et al. |
| 2003/0191497 A1 | 10/2003 | Cope |
| 2003/0199860 A1 | 10/2003 | Loeb et al. |
| 2003/0204195 A1 | 10/2003 | Keane et al. |
| 2003/0236535 A1 | 12/2003 | Onuki et al. |
| 2004/0010301 A1 | 1/2004 | Kindlein et al. |
| 2004/0030217 A1 | 2/2004 | Yeung et al. |
| 2004/0043052 A1 | 3/2004 | Hunter et al. |
| 2004/0078046 A1 | 4/2004 | Barzell et al. |
| 2004/0122456 A1 | 6/2004 | Saadat et al. |
| 2004/0122474 A1 | 6/2004 | Gellman et al. |
| 2004/0143343 A1 | 7/2004 | Grocela |
| 2004/0147958 A1 | 7/2004 | Lam et al. |
| 2004/0162568 A1 | 8/2004 | Saadat et al. |
| 2004/0167635 A1 | 8/2004 | Yachia et al. |
| 2004/0172046 A1 | 9/2004 | Hlavka et al. |
| 2004/0193191 A1 | 9/2004 | Starksen et al. |
| 2004/0193194 A1 | 9/2004 | Laufer et al. |
| 2004/0194790 A1 | 10/2004 | Laufer et al. |
| 2004/0215181 A1 | 10/2004 | Christopherson et al. |
| 2004/0225305 A1* | 11/2004 | Ewers ............... A61B 17/0401 606/153 |
| 2004/0230316 A1 | 11/2004 | Cioanta et al. |

(56) References Cited

U.S. PATENT DOCUMENTS

| | | |
|---|---|---|
| 2004/0243178 A1 | 12/2004 | Haut et al. |
| 2004/0243179 A1 | 12/2004 | Foerster |
| 2004/0243180 A1 | 12/2004 | Donnelly et al. |
| 2004/0243227 A1 | 12/2004 | Starksen et al. |
| 2004/0260345 A1 | 12/2004 | Foerster |
| 2005/0010203 A1 | 1/2005 | Edwards et al. |
| 2005/0033403 A1 | 2/2005 | Ward et al. |
| 2005/0055087 A1 | 3/2005 | Starksen |
| 2005/0059929 A1 | 3/2005 | Bolmsjo et al. |
| 2005/0065550 A1 | 3/2005 | Starksen et al. |
| 2005/0101982 A1 | 5/2005 | Ravenscroft et al. |
| 2005/0107811 A1 | 5/2005 | Starksen et al. |
| 2005/0107812 A1 | 5/2005 | Starksen et al. |
| 2005/0137716 A1 | 6/2005 | Gross |
| 2005/0154401 A1 | 7/2005 | Weldon et al. |
| 2005/0165272 A1 | 7/2005 | Okada et al. |
| 2005/0171522 A1 | 8/2005 | Christopherson |
| 2005/0177181 A1 | 8/2005 | Kagan et al. |
| 2005/0203344 A1 | 9/2005 | Orban et al. |
| 2005/0203550 A1 | 9/2005 | Laufer et al. |
| 2005/0216040 A1 | 9/2005 | Gertner et al. |
| 2005/0216078 A1 | 9/2005 | Starksen et al. |
| 2005/0222557 A1 | 10/2005 | Baxter et al. |
| 2005/0251157 A1 | 11/2005 | Saadat et al. |
| 2005/0251159 A1 | 11/2005 | Ewers et al. |
| 2005/0251177 A1 | 11/2005 | Saadat et al. |
| 2005/0251206 A1 | 11/2005 | Maahs et al. |
| 2005/0267405 A1 | 12/2005 | Shah |
| 2005/0273138 A1 | 12/2005 | To et al. |
| 2005/0283189 A1 | 12/2005 | Rosenblatt |
| 2005/0288694 A1 | 12/2005 | Solomon |
| 2006/0004410 A1 | 1/2006 | Nobis et al. |
| 2006/0020276 A1 | 1/2006 | Saadat et al. |
| 2006/0025750 A1 | 2/2006 | Starksen et al. |
| 2006/0025784 A1 | 2/2006 | Starksen et al. |
| 2006/0025789 A1 | 2/2006 | Laufer et al. |
| 2006/0025819 A1 | 2/2006 | Nobis et al. |
| 2006/0026750 A1 | 2/2006 | Ballance |
| 2006/0030884 A1 | 2/2006 | Yeung et al. |
| 2006/0058817 A1 | 3/2006 | Starksen et al. |
| 2006/0079880 A1 | 4/2006 | Sage et al. |
| 2006/0079881 A1 | 4/2006 | Christopherson et al. |
| 2006/0089646 A1 | 4/2006 | Bonutti |
| 2006/0095058 A1 | 5/2006 | Sivan et al. |
| 2006/0167477 A1 | 7/2006 | Arcia et al. |
| 2006/0178680 A1 | 8/2006 | Nelson et al. |
| 2006/0199996 A1 | 9/2006 | Caraballo et al. |
| 2006/0241694 A1 | 10/2006 | Cerundolo |
| 2006/0265042 A1 | 11/2006 | Catanese et al. |
| 2006/0271032 A1 | 11/2006 | Chin et al. |
| 2006/0276481 A1 | 12/2006 | Evrard et al. |
| 2006/0276871 A1 | 12/2006 | Lamson et al. |
| 2006/0282081 A1 | 12/2006 | Fanton et al. |
| 2007/0049929 A1 | 3/2007 | Catanese et al. |
| 2007/0049970 A1 | 3/2007 | Belef et al. |
| 2007/0060931 A1 | 3/2007 | Hamilton et al. |
| 2007/0073322 A1 | 3/2007 | Mikkaichi et al. |
| 2007/0073342 A1 | 3/2007 | Stone et al. |
| 2007/0088362 A1 | 4/2007 | Bonutti et al. |
| 2007/0100421 A1 | 5/2007 | Griffin |
| 2007/0112385 A1 | 5/2007 | Conlon |
| 2007/0142846 A1 | 6/2007 | Catanese et al. |
| 2007/0173888 A1 | 7/2007 | Gertner et al. |
| 2007/0179491 A1 | 8/2007 | Kratoska et al. |
| 2007/0179496 A1 | 8/2007 | Swoyer et al. |
| 2007/0198038 A1 | 8/2007 | Cohen et al. |
| 2007/0260259 A1 | 11/2007 | Fanton et al. |
| 2008/0009888 A1 | 1/2008 | Ewers et al. |
| 2008/0021445 A1 | 1/2008 | Elmouelhi et al. |
| 2008/0021485 A1 | 1/2008 | Catanese et al. |
| 2008/0033458 A1 | 2/2008 | McLean et al. |
| 2008/0033488 A1 | 2/2008 | Catanese et al. |
| 2008/0039833 A1 | 2/2008 | Catanese et al. |
| 2008/0039872 A1 | 2/2008 | Catanese et al. |
| 2008/0039874 A1 | 2/2008 | Catanese et al. |
| 2008/0039875 A1 | 2/2008 | Catanese et al. |
| 2008/0039893 A1 | 2/2008 | McLean et al. |
| 2008/0039894 A1 | 2/2008 | Catanese et al. |
| 2008/0039921 A1 | 2/2008 | Wallsten et al. |
| 2008/0045978 A1 | 2/2008 | Kuhns et al. |
| 2008/0051810 A1 | 2/2008 | To et al. |
| 2008/0058710 A1 | 3/2008 | Wilk |
| 2008/0065120 A1 | 3/2008 | Zannis et al. |
| 2008/0082113 A1 | 4/2008 | Bishop et al. |
| 2008/0086172 A1 | 4/2008 | Martin et al. |
| 2008/0091220 A1 | 4/2008 | Chu |
| 2008/0091237 A1 | 4/2008 | Schwartz et al. |
| 2008/0119874 A1 | 5/2008 | Merves |
| 2008/0154378 A1 | 6/2008 | Pelo |
| 2008/0161852 A1 | 7/2008 | Kaiser et al. |
| 2008/0195145 A1 | 8/2008 | Bonutti et al. |
| 2008/0208220 A1 | 8/2008 | Shiono et al. |
| 2008/0228202 A1 | 9/2008 | Cropper et al. |
| 2008/0269737 A1 | 10/2008 | Elmouelhi et al. |
| 2009/0012537 A1 | 1/2009 | Green |
| 2009/0018553 A1 | 1/2009 | McLean et al. |
| 2009/0060977 A1 | 3/2009 | Lamson et al. |
| 2009/0112234 A1 | 4/2009 | Crainich et al. |
| 2009/0112537 A1 | 4/2009 | Okumura |
| 2009/0118762 A1 | 5/2009 | Crainch et al. |
| 2009/0177288 A1 | 7/2009 | Wallsten |
| 2009/0198227 A1 | 8/2009 | Prakash |
| 2010/0010631 A1 | 1/2010 | Otte et al. |
| 2010/0023022 A1 | 1/2010 | Zeiner et al. |
| 2010/0023024 A1 | 1/2010 | Zeiner et al. |
| 2010/0023025 A1 | 1/2010 | Zeiner et al. |
| 2010/0023026 A1 | 1/2010 | Zeiner et al. |
| 2010/0030262 A1 | 2/2010 | McLean et al. |
| 2010/0030263 A1 | 2/2010 | Cheng et al. |
| 2010/0049188 A1 | 2/2010 | Nelson et al. |
| 2010/0063542 A1 | 3/2010 | Burg et al. |
| 2010/0114162 A1 | 5/2010 | Bojarski et al. |
| 2010/0130815 A1 | 5/2010 | Gross et al. |
| 2010/0286106 A1 | 11/2010 | Gat et al. |
| 2010/0286679 A1 | 11/2010 | Hoey et al. |
| 2010/0298948 A1 | 11/2010 | Hoey et al. |
| 2010/0324669 A1 | 12/2010 | Hlavka et al. |
| 2011/0040312 A1 | 2/2011 | Lamson et al. |
| 2011/0046648 A1 | 2/2011 | Johnston et al. |
| 2011/0060349 A1 | 3/2011 | Cheng et al. |
| 2011/0077676 A1 | 3/2011 | Sivan et al. |
| 2011/0144423 A1 | 6/2011 | Tong et al. |
| 2011/0152839 A1 | 6/2011 | Cima et al. |
| 2011/0160747 A1 | 6/2011 | McLean et al. |
| 2011/0166564 A1 | 7/2011 | Merrick et al. |
| 2011/0190758 A1 | 8/2011 | Lamson et al. |
| 2011/0196393 A1 | 8/2011 | Eliachar et al. |
| 2011/0202052 A1 | 8/2011 | Gelbart et al. |
| 2011/0218387 A1 | 9/2011 | Lamson et al. |
| 2011/0245828 A1 | 10/2011 | Baxter et al. |
| 2011/0276081 A1 | 11/2011 | Kilemnik |
| 2011/0276086 A1 | 11/2011 | Al-Qbandi et al. |
| 2012/0010645 A1 | 1/2012 | Feld |
| 2012/0059387 A1 | 3/2012 | Schanz et al. |
| 2012/0165837 A1 | 6/2012 | Belman et al. |
| 2012/0203250 A1 | 8/2012 | Weir et al. |
| 2012/0245600 A1 | 9/2012 | McLean et al. |
| 2012/0265006 A1 | 10/2012 | Makower et al. |
| 2013/0096582 A1 | 4/2013 | Cheng et al. |
| 2013/0178871 A1 | 7/2013 | Koogle et al. |
| 2013/0211431 A1 | 8/2013 | Wei et al. |
| 2013/0253574 A1 | 9/2013 | Catanese et al. |
| 2013/0253662 A1 | 9/2013 | Lamson et al. |
| 2013/0261383 A1 | 10/2013 | Catanese et al. |
| 2013/0261665 A1 | 10/2013 | Yeung et al. |
| 2013/0267772 A1 | 10/2013 | Catanese et al. |
| 2013/0268001 A1 | 10/2013 | Catanese et al. |
| 2013/0274799 A1 | 10/2013 | Catanese et al. |
| 2013/0289342 A1 | 10/2013 | Tong et al. |
| 2013/0296639 A1 | 11/2013 | Lamson et al. |
| 2013/0296889 A1 | 11/2013 | Tong et al. |
| 2013/0296935 A1 | 11/2013 | McLean et al. |
| 2013/0325143 A1 | 12/2013 | Lamson et al. |
| 2014/0005473 A1 | 1/2014 | Catanese et al. |

(56) References Cited

U.S. PATENT DOCUMENTS

| | | |
|---|---|---|
| 2014/0005690 A1 | 1/2014 | Catanese et al. |
| 2014/0012192 A1 | 1/2014 | Bar-On et al. |
| 2014/0088587 A1 | 3/2014 | Merrick et al. |
| 2014/0221981 A1 | 8/2014 | Cima et al. |
| 2014/0236230 A1 | 8/2014 | Johnston et al. |
| 2014/0288637 A1 | 9/2014 | Clerc et al. |
| 2015/0112299 A1 | 4/2015 | Forbes et al. |
| 2015/0157309 A1 | 6/2015 | Bird |
| 2015/0257908 A1 | 9/2015 | Chao et al. |
| 2015/0335393 A1 | 11/2015 | Ciulla et al. |
| 2016/0000455 A1 | 1/2016 | Golan et al. |
| 2016/0038087 A1 | 2/2016 | Hunter |
| 2016/0051735 A1 | 2/2016 | Slepian |
| 2016/0081736 A1 | 3/2016 | Hoey et al. |
| 2016/0089140 A1 | 3/2016 | Kawaura et al. |
| 2016/0096009 A1 | 4/2016 | Feld |
| 2016/0120647 A1 | 5/2016 | Rogers et al. |
| 2016/0206370 A1 | 7/2016 | Fruland et al. |
| 2016/0242894 A1 | 8/2016 | Davis |
| 2016/0302904 A1 | 10/2016 | Ogdahl et al. |
| 2016/0317180 A1 | 11/2016 | Kilemnik |
| 2017/0000598 A1 | 1/2017 | Bachar |
| 2017/0128741 A1 | 5/2017 | Keltner et al. |
| 2017/0135830 A1 | 5/2017 | Harkin et al. |

FOREIGN PATENT DOCUMENTS

| | | |
|---|---|---|
| CN | 101795641 A | 8/2010 |
| CN | 102112064 B | 6/2014 |
| CN | 105919695 A | 9/2016 |
| DE | 10159470 A1 | 6/2003 |
| EP | 0246836 B1 | 12/1991 |
| EP | 0464480 A1 | 1/1992 |
| EP | 0274846 B1 | 2/1994 |
| EP | 0632999 A1 | 1/1995 |
| EP | 0667126 A1 | 8/1995 |
| EP | 1016377 A2 | 7/2000 |
| EP | 1482841 A1 | 12/2004 |
| EP | 1082941 B1 | 3/2005 |
| EP | 1006909 B1 | 1/2007 |
| EP | 1852071 A2 | 11/2007 |
| EP | 1584295 B1 | 2/2008 |
| EP | 1884198 A2 | 2/2008 |
| EP | 1884199 A1 | 2/2008 |
| EP | 1670361 B1 | 4/2008 |
| EP | 1331886 B1 | 12/2008 |
| EP | 1482840 B1 | 12/2008 |
| EP | 2243507 A1 | 10/2010 |
| EP | 1484023 B1 | 5/2011 |
| EP | 2345373 A1 | 7/2011 |
| EP | 2345374 A1 | 7/2011 |
| EP | 2049023 B1 | 12/2014 |
| EP | 3167845 A1 | 5/2017 |
| FR | 2750031 A1 | 12/1997 |
| JP | 5836559 A | 3/1983 |
| JP | 09122134 | 5/1997 |
| JP | 3370300 B2 | 1/2003 |
| JP | 2004344427 A | 12/2004 |
| JP | 2009521278 A | 6/2009 |
| JP | 2011529745 A | 12/2011 |
| JP | 2012143622 A | 8/2012 |
| KR | 20060009698 A | 2/2006 |
| RU | 2062121 C1 | 6/1996 |
| RU | 2112571 C1 | 6/1998 |
| RU | 2128012 C1 | 3/1999 |
| RU | 2221501 C2 | 1/2004 |
| SU | 825094 A1 | 4/1981 |
| WO | 1987001270 A1 | 3/1987 |
| WO | 1992010142 A1 | 6/1992 |
| WO | 1993004727 A1 | 3/1993 |
| WO | 1993015664 A1 | 8/1993 |
| WO | 1995000818 A1 | 1/1995 |
| WO | 2000040159 A1 | 7/2000 |
| WO | 2001026588 A2 | 4/2001 |
| WO | 2001028432 A1 | 4/2001 |
| WO | 2001039671 A1 | 6/2001 |
| WO | 2001049195 A1 | 7/2001 |
| WO | 2001095818 A1 | 12/2001 |
| WO | 2002028289 A1 | 4/2002 |
| WO | 2002030335 A2 | 4/2002 |
| WO | 2002032321 A1 | 4/2002 |
| WO | 2002058577 A1 | 8/2002 |
| WO | 2003039334 A2 | 5/2003 |
| WO | 2003077772 A1 | 9/2003 |
| WO | 2004000159 A2 | 12/2003 |
| WO | 2004017845 A1 | 3/2004 |
| WO | 2004019787 A2 | 3/2004 |
| WO | 2004019788 A2 | 3/2004 |
| WO | 2004030569 A2 | 4/2004 |
| WO | 2004066875 A1 | 8/2004 |
| WO | 2004080529 A2 | 9/2004 |
| WO | 2004103189 A1 | 12/2004 |
| WO | 2005034738 A2 | 4/2005 |
| WO | 2005065412 A2 | 7/2005 |
| WO | 2005094447 A2 | 10/2005 |
| WO | 2006127241 A2 | 11/2006 |
| WO | 2006127431 A2 | 11/2006 |
| WO | 2007048437 A1 | 5/2007 |
| WO | 2007053516 A2 | 5/2007 |
| WO | 2007064906 A2 | 6/2007 |
| WO | 2007075981 A2 | 7/2007 |
| WO | 2008002340 A2 | 1/2008 |
| WO | 2008006084 A2 | 1/2008 |
| WO | 2008014191 A2 | 1/2008 |
| WO | 2008043044 A2 | 4/2008 |
| WO | 2008043917 A2 | 4/2008 |
| WO | 2008097942 A1 | 8/2008 |
| WO | 2008132735 A1 | 11/2008 |
| WO | 2008142677 A2 | 11/2008 |
| WO | 2009009617 A1 | 1/2009 |
| WO | 2009072131 A2 | 6/2009 |
| WO | 2010011832 A1 | 1/2010 |
| WO | 2010014821 A2 | 2/2010 |
| WO | 2010014825 A2 | 2/2010 |
| WO | 2010065214 A2 | 6/2010 |
| WO | 2010086849 A1 | 8/2010 |
| WO | 2010106543 A2 | 9/2010 |
| WO | 2011084712 A1 | 7/2011 |
| WO | 2012018446 A2 | 2/2012 |
| WO | 2012079548 A1 | 6/2012 |
| WO | 2012079549 A2 | 6/2012 |
| WO | 2012091952 A2 | 7/2012 |
| WO | 2012091954 A2 | 7/2012 |
| WO | 2012091955 A2 | 7/2012 |
| WO | 2012091956 A2 | 7/2012 |
| WO | 2012123950 A2 | 9/2012 |
| WO | 2014003987 A1 | 1/2014 |
| WO | 2014035506 A2 | 3/2014 |
| WO | 2014145381 A1 | 9/2014 |
| WO | 2014153219 A1 | 9/2014 |
| WO | 2014200764 A1 | 12/2014 |
| WO | 2015101975 A1 | 7/2015 |
| WO | 2016134166 A1 | 8/2016 |
| WO | 2017017499 A1 | 2/2017 |
| WO | 2017081326 A2 | 5/2017 |
| WO | 2017112856 A1 | 6/2017 |

OTHER PUBLICATIONS

Berges, Richard, et al. "Alternative Minimalinvasive Therapien Beim Benignen Prostatasyndrom", Medizin, Jg. 104, Heft 37, Sep. 14, 2007.

Borzhievski, et al., "Tactics of the Surgical Treatment of Patients With Prostatic Adenoma and Acute Urinary Retention," Urologia Nefrol (Mosk), Jan.-Feb. 1987, (1):39-43.

European Search Report for EP Application No. 06770621.8, dated Sep. 20, 2012.

Search Report for EP Application No. 06845991.6, dated Mar. 22, 2013.

Search Report for EP Application No. 07840462.1, dated May 29, 2012.

Search Report for EP Application No. 08729001.1, dated Feb. 4, 2014.

(56) References Cited

OTHER PUBLICATIONS

Search Report for EP Application No. 08772483.7, dated Feb. 12, 2015.
Search Report for EP Application No. 11154962.2, dated May 19, 2011.
European Search Report for EP Application No. 11154976.2, dated Jun. 6, 2011.
European Search Report for EP Application No. 11814950.9, dated Sep. 8, 2015.
European Search Report for EP Application No. 11852778.7, dated Nov. 19, 2015.
European Search Report for EP Application No. 11854148.1, dated Oct. 20, 2017.
European Search Report for EP Application No. 13810314.8, dated Apr. 6, 2016.
European Search Report for EP Application No. 17150545.6, dated Sep. 11, 2017.
Hartung, Rudolf, et al. "Instrumentelle Therapie der benignen Prostatahyperplasie", Medizin, Deutsches Arzteblatt 97, Heft 15, Apr. 14, 2000.
Hofner, Klaus, et al., "Operative Therapie des benignen Prostatasyndroms", Medizin, Dtsch Arztebl, 2007; 104(36): A 2424-9.
Hubmann, R. "Geschichte der transurethralen Prostataeingriffe", Geschichte der Medizin, Urologe [B], 2000, 40:152-160.
International Search Report for PCT Application No. PCT/US2006/019372, dated May 2, 2008.
International Search Report for PCT Application No. PCT/US2006/048962,dated Dec. 10, 2008.
International Search Report for PCT Application No. PCT/US2007/074019, dated Jul. 25, 2008.
International Search Report for PCT Application No. PCT/US2008/053001, dated Jun. 17, 2008.
International Search Report for PCT Application No. PCT/US2008/069560, dated Sep. 8, 2008.
International Search Report for PCT Application No. PCT/US2009/052271, dated Apr. 7, 2010.
International Search Report for PCT Application No. PCT/US2009/052275, dated Oct. 9, 2009.
International Search Report for PCT Application No. PCT/US2011/041200, dated Feb. 17, 2012.
International Search Report for PCT Application No. PCT/US2011/065348, dated Jun. 21, 2012.
International Search Report for PCT Application No. PCT/US2011/065358, dated Jun. 21, 2012.
International Search Report for PCT Application No. PCT/US2011/065377, dated Aug. 29, 2012.
International Search Report for PCT Application No. PCT/US2011/065386, dated Jun. 28, 2012.
International Search Report for PCT Application No. PCT/US2013/044035, dated Sep. 6, 2013.
Jonas, U., et al., "Benigne Prostatahyperplasie", Der Urologe 2006—[Sonderheft] 45:134-144.
Kruck, S., et al., "Aktuelle Therapiemoglichkeiten des Benignen Prostata-Syndroms", J Urol Urogynakol, 2009; 16(1): 19-22.
Miyake, Osamu. "Medical Examination and Treatment for BPH," Pharma Med, vol. 22, No. 3, 2004, p. 97-103.
Reich, O., et al., "Benignes Prostatasyndrom (BPS)," Der Urologe A Issue vol. 45, No. 6, Jun. 2006, p. 769-782.
Schauer, P., et al. "New applications for endoscopy: the emerging field of endoluminal and transgastric bariatric surgery", Surgical Endoscopy, (Apr. 24, 2006), 10 pgs.
Sharp, Howard T., M.D., et al. "Instruments and Methods—The 4-S Modification of the Roeder Knot: How to Tie It", Obstetrics & Gynecology, p. 1004-1006, vol. 90, No. 6, Dec. 1997.
Takashi, Daito. "Low-Invasive Treatment for BPH", Medico vol. 34, No. 10, p. 366-369, 2000.
Teruhisa, Ohashi. "Urinary Dysfunction by Lower Urinary Tract Obstruction in Male", Pharma Medica, vol. 8, No. 8, p. 35-39, 1990.
Tomohiko, Koyanagi, et al., "Surgery View of 21st Century," Urological Surgery, vol. 84, No. 1, p. 47-53, 2001.
Trapeznikov, et al., "New Technologies in the Treatment of Benign Prostatic Hyperplasia", Urologia Nefrol (Mosk), Jul.-Aug. 1996, (4):41-47.
Yeung, Jeff. "Treating Urinary Stress Incontenance Without Incision with Endoscopic Suture Anchor & Approximating Device," Aleeva Medical, Inc., 2007.

\* cited by examiner

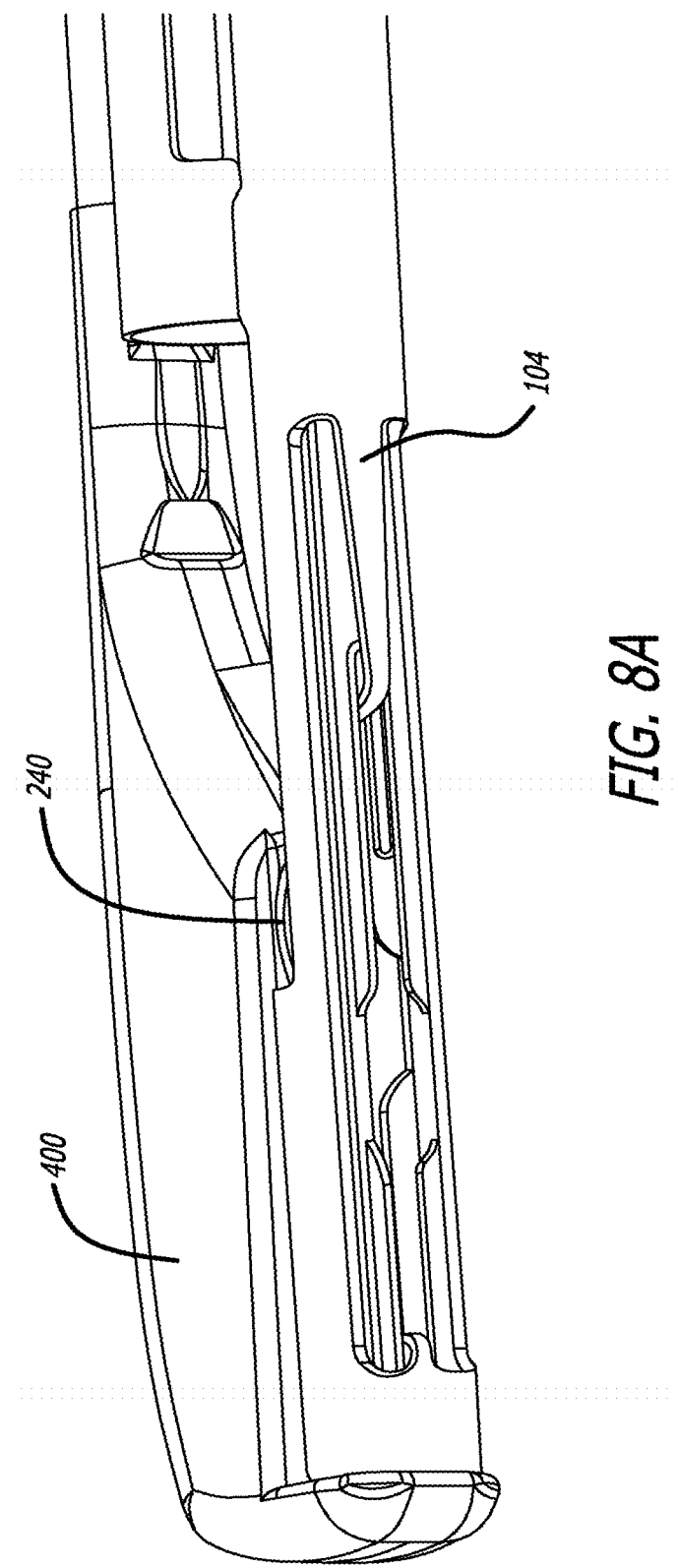

ANCHOR DELIVERY SYSTEM

CROSS-REFERENCE TO RELATED APPLICATIONS

This application is a continuation of U.S. patent application Ser. No. 13/830,684, filed Mar. 14, 2013, which is a continuation-in-part of U.S. patent application Ser. No. 13/692,876, now U.S. Pat. No. 8,939,996, filed Dec. 3, 2012, which is a continuation of U.S. patent application Ser. No. 12/852,243, now U.S. Pat. No. 8,333,776, filed Aug. 6, 2010, which in turn is a continuation-in-part of: 1) U.S. patent application Ser. No. 12/512,674, now U.S. Pat. No. 8,216,254, filed Jul. 30, 2009 which claims the benefit of Provisional Application Ser. No. 61/084,937 filed Jul. 30, 2008; 2) U.S. patent application Ser. No. 11/775,162, now U.S. Pat. No. 8,945,151, filed Jul. 9, 2007; 3) U.S. patent application Ser. No. 11/671,914, now U.S. Pat. No. 8,157,815, filed Feb. 6, 2007; 4) U.S. patent application Ser. No. 11/492,690, now U.S. Pat. No. 7,896,891, filed on Jul. 24, 2006; 5) U.S. patent application Ser. No. 11/833,660, now U.S. Pat. No. 8,940,001, filed on Aug. 3, 2007, which is a continuation of U.S. patent application Ser. No. 11/318,246, now U.S. Pat. No. 7,645,286, filed on Dec. 22, 2005; and 6) U.S. patent application Ser. No. 11/838,036, now U.S. Pat. No. 7,914,542, filed on Aug. 13, 2007, which is a continuation of U.S. patent application Ser. No. 11/134,870, now U.S. Pat. No. 7,758,594, filed on May 20, 2005; the entire disclosures of each of which are expressly incorporated herein by reference.

BACKGROUND

The present disclosure relates generally to medical devices and methods, and more particularly to systems and associated methods for manipulating or retracting tissues and anatomical or other structures within the body of human or animal subjects for the purpose of treating diseases or disorders and/or for cosmetic or reconstructive surgery or other purposes.

There are a wide variety of situations in which it is desirable to lift, compress or otherwise reposition normal or aberrant tissues or anatomical structures (e.g., organs, ligaments, tendons, muscles, tumors, cysts, fat pads, etc.) within the body of a human or animal subject. Such procedures are often carried out for the purpose of treating or palliating the effects of diseases or disorders (e.g., hyperplasic conditions, hypertrophic conditions, neoplasias, prolapses, herniations, stenoses, constrictions, compressions, transpositions, congenital malformations, etc.) and/or for cosmetic purposes (e.g., face lifts, breast lifts, brow lifts, etc.) and/or for research and development purposes (e.g., to create animal models that mimic various pathological conditions). In many of these procedures, surgical incisions are made in the body and laborious surgical dissection is performed to access and expose the affected tissues or anatomical structures. Thereafter, in some cases, the affected tissues or anatomical structures are removed or excised. In other cases, various natural or manmade materials are used to lift, sling, reposition or compress the affected tissues.

One example of a condition where it is desirable to lift, compress, move or otherwise remove a pathologically enlarged tissue is Benign Prostatic Hyperplasia (BPH). BPH is one of the most common medical conditions that affect men, especially elderly men. It has been reported that, in the United States, more than half of all men have histopathologic evidence of BPH by age 60 and, by age 85, approximately 9 out of 10 men suffer from the condition. Moreover, the incidence and prevalence of BPH are expected to increase as the average age of the population in developed countries increases.

The prostate gland enlarges throughout a man's life. In some men, the prostatic capsule around the prostate gland may prevent the prostate gland from enlarging further. This causes the inner region of the prostate gland to squeeze the urethra. This pressure on the urethra increases resistance to urine flow through the region of the urethra enclosed by the prostate. Thus the urinary bladder has to exert more pressure to force urine through the increased resistance of the urethra. Chronic over-exertion causes the muscular walls of the urinary bladder to remodel and become stiffer. This combination of increased urethral resistance to urine flow and stiffness and hypertrophy of urinary bladder walls leads to a variety of lower urinary tract symptoms (LUTS) that may severely reduce the patient's quality of life. These symptoms include weak or intermittent urine flow while urinating, straining when urinating, hesitation before urine flow starts, feeling that the bladder has not emptied completely even after urination, dribbling at the end of urination or leakage afterward, increased frequency of urination particularly at night, urgent need to urinate etc.

In addition to patients with BPH, LUTS may also be present in patients with prostate cancer, prostate infections, and chronic use of certain medications (e.g. ephedrine, pseudoephedrine, phenylpropanolamine, antihistamines such as diphenhydramine, chlorpheniramine etc.) that cause urinary retention especially in men with prostate enlargement.

Although BPH is rarely life threatening, it can lead to numerous clinical conditions including urinary retention, renal insufficiency, recurrent urinary tract infection, incontinence, hematuria, and bladder stones.

In developed countries, a large percentage of the patient population undergoes treatment for BPH symptoms. It has been estimated that by the age of 80 years, approximately 25% of the male population of the United States will have undergone some form of BPH treatment. At present, the available treatment options for BPH include watchful waiting, medications (phytotherapy and prescription medications), surgery and minimally invasive procedures.

For patients who choose the watchful waiting option, no immediate treatment is provided to the patient, but the patient undergoes regular exams to monitor progression of the disease. This is usually done on patients that have minimal symptoms that are not especially bothersome.

Surgical procedures for treating BPH symptoms include Transurethral Resection of Prostate (TURP), Transurethral Electrovaporization of Prostate (TVP), Transurethral Incision of the Prostate (TUIP), Laser Prostatectomy and Open Prostatectomy.

Minimally invasive procedures for treating BPH symptoms include Transurethral Microwave Thermotherapy (TUMT), Transurethral Needle Ablation (TUNA), Interstitial Laser Coagulation (ILC), and Prostatic Stents.

The most effective current methods of treating BPH carry a high risk of adverse effects. These methods and devices either require general or spinal anesthesia or have potential adverse effects that dictate that the procedures be performed in a surgical operating room, followed by a hospital stay for the patient. The methods of treating BPH that carry a lower risk of adverse effects are also associated with a lower reduction in the symptom score. While several of these procedures can be conducted with local analgesia in an office setting, the patient does not experience immediate relief and in fact often experiences worse symptoms for weeks after the procedure until the body begins to heal. Additionally all device approaches require a urethral catheter placed in the bladder, in some cases for weeks. In some cases catheterization is indicated because the therapy actually causes obstruction during a period of time post operatively, and in other cases it is indicated because of post-operative bleeding and potentially occlusive clot formation. While drug therapies are easy to administer, the results are suboptimal, take significant time to take effect, and often entail undesired side effects.

Many women experience loss of bladder control following childbirth or in old age. This condition is broadly referred to as urinary incontinence (UI). The severity of UI varies and, in severe cases, the disorder can be totally debilitating, keeping the patient largely homebound. It is usually associated with a cystocele, which results from sagging of the neck of the urinary bladder into or even outside the vagina The treatments for UI include behavioral therapy, muscle strengthening exercises (e.g., Kegel exercises), drug therapy, electrical stimulation of the pelvic nerves, use of intravaginal devices and surgery.

In severe cases of UI, surgery is generally the best treatment option. In general, the surgical procedures used to treat UI attempt to lift and support the bladder so that the bladder and urethra are returned to their normal positions within the pelvic cavity. The two most common ways of performing these surgeries is through incisions formed in the abdominal wall or through the wall of the vagina.

A number of different surgical procedures have been used to treat UI. The names for these procedures include the Birch Procedure, Marshall-Marchetti Operation, MMK, Pubo-Vaginal Sling, Trans-Vaginal Tape Procedure, Urethral Suspension, Vesicourethral Suspension. These procedures generally fall into two categories, namely a) retropubic suspension procedures and b) sling procedures.

In retropubic suspension procedures, an incision is typically made in the abdominal wall a few inches below the navel and a network of connectors are placed to support the bladder neck. The connectors are anchored to the pubic bone and to other structures within the pelvis, essentially forming a cradle which supports the urinary bladder.

In sling procedures, an incision is typically made in the wall of the vagina and a sling is crafted of either natural tissue or synthetic (man-made) material to support the bladder neck. Both ends of the sling may be attached to the pubic bone or tied in front of the abdomen just above the pubic bone. In some sling procedures a synthetic tape is used to form the sling and the ends of the synthetic tape are not tied but rather pulled up above the pubic bone.

The surgeries used to treat UI are generally associated with significant discomfort as the incisions heal and may require a Foley or supra-pubic urinary catheter to remain in place for at least several days following the surgery. Thus, there exists a need in the art for the development of minimally invasive (e.g., non-incisional) procedures for the treatment of UI with less postoperative discomfort and less requirement for post-surgical urinary catheterization.

Many cosmetic or reconstructive surgical procedures involve lifting, compressing or repositioning of natural tissue, natural tissue or artificial grafts or aberrant tissue. For example, surgical procedures such as face lifts, brow lifts, neck lifts, tummy tucks, etc. have become commonplace. In many cases, these procedures are performed by creating incisions through the skin, dissecting to a plane beneath muscles and fascia, freeing the muscles, fascia and overlying skin from underlying structures (e.g., bone or other muscles), lifting or repositioning the freed muscles, fascia and overlying skin and then attaching the repositioned tissues to underlying or nearby structures (e.g., bone, periostium, other muscles) to hold the repositioned tissues in their new (e.g., lifted) position. In some cases excess skin may also be removed during the procedure.

There have been attempts to develop minimally invasive devices and methods for cosmetic lifting and repositioning of tissues. For example, connector suspension lifts have been developed where one end of a standard or modified connector thread is attached to muscle and the other end is anchored to bone, periostium or another structure to lift and reposition the tissues as desired. Some of these connector suspension techniques have been performed through cannulas or needles inserted through relatively small incisions of puncture wounds.

There remains a need for the development of new devices and methods that can be used for various procedures where it is desired to lift, compress, support or reposition tissues or organs within the body with less intraoperative trauma, less post-operative discomfort and/or shorter recovery times. Further, there is a need for an apparatus and related method which facilitate ensuring precise placement of an anchor assembly. Various refinements in approach have been found beneficial to ensure reliable assembly of tissue anchor components, including approaches to assure a robust engagement of parts. Structures ensuring proper timing of steps in an assembly have also been found to be beneficial as well as the proper alignment of component parts intended for implant.

The present disclosure addresses these and other needs.

SUMMARY

Briefly and in general terms, the present disclosure is directed towards an apparatus and method for deploying an anchor assembly within a patient's body. The apparatus of the present disclosure includes various subassemblies which are mobilized via an actuator or other manually accessible structure. The operation of the subassemblies is coordinated and synchronized to ensure accurate and precise implantation of an anchor assembly.

In particular, the present disclosure is directed towards a system for treatment of body tissue, comprising an anchor assembly, the anchor assembly including a first anchor component attached to a connector and a second anchor component and a delivery device, the delivery device including a handle, an elongate portion extending from the handle, the elongate portion including a leading end, a needle tube, and a scope assembly, a needle assembly extending through the needle tube and configured to be ejected from the leading end, and the connector extending through the needle assembly, wherein the leading end includes a needle targeting structure configured to facilitate targeting the needle through tissue. In an additional or alternative aspect, the system includes connector manipulating structure configured to facilitate presenting the connector to the second anchor component for a robust connection.

In one embodiment, the delivery device is embodied in a tissue approximation assembly. The delivery device includes a case assembly enclosing an anchor delivery and assembly structure, a needle spool assembly and a suture spool assembly. Extending from the case assembly is a shaft assembly. Also, extending through the shaft assembly are a pusher assembly, a needle, and a cutter assembly. An actuator mechanism is operatively associated with the anchor assembly structure. Activation of a needle actuator accomplishes the advancement of a needle assembly and a first anchor component of an anchor assembly attached to a connector member, to an interventional site. Activation of a needle retraction actuator withdraws the needle assembly leaving the first anchor component of the anchor assembly at the interventional site. Thereafter, manipulation of an assembly actuator results in lockingly engaging a second anchor component with the connector member and cutting the connector member at a point between the second anchor component and shaft assembly.

In one particular aspect, the present disclosure is directed towards a delivery device, which accomplishes the delivery of a first or distal anchor assembly component at a first location within a patient's body and the delivery of a second or proximal anchor assembly component at a second location within the patient.

Additionally, in a contemplated embodiment of an anchor delivery system, actuating a needle deploy actuator results in a needle being advanced within a patient to an interventional site. Activating a needle retraction lever accomplishes the withdrawal of the needle and deployment of a first anchor component of an anchor assembly at the interventional site.

The anchor assembly can be configured to accomplish approximating, retracting, lifting, compressing, supporting or repositioning tissue within the body of a human or animal subject. Moreover, the apparatus configured to deploy the anchor assembly as well as the anchor assembly itself are configured to complement and cooperate with body anatomy.

In a specific embodiment, the anchor delivery device includes a generally elongate tubular housing assembly member extending distally from a handle assembly including an actuator. The proximal end of the handle assembly is equipped with mounting structure configured to receive a telescope or other endoscopic viewing instrument. A bore sized to receive the telescope extends distally through a body of the handle assembly and continues through an outer tubular cover member forming the generally elongate member. Housed within the tubular housing assembly are a telescope tube having an interior defining a distal section of the bore sized to receive the telescope, an upper tubular member assembly sized to receive at least one component of the implant assembly inside a needle, and a lower tubular member assembly sized to receive at least one second component of the implant assembly below a cutter member.

Moreover, various alternative methods of use are also contemplated. That is, in some applications of the system, the system is used to improve flow of a body fluid through a body lumen, modify the size or shape of a body lumen or cavity, treat prostate enlargement, treat urinary incontinence, support or maintain positioning of a tissue, close a tissue wound, organ or graft, perform a cosmetic lifting or repositioning procedure, form anastomotic connections, and/or treat various other disorders where a natural or pathologic tissue or organ is pressing on or interfering with an adjacent anatomical structure. Also, the system has a myriad of other potential surgical, therapeutic, cosmetic or reconstructive applications, such as where a tissue, organ, graft or other material requires approximately, retracting, lifting, repositioning, compression or support.

Other features and advantages of the present disclosure will become apparent from the following detailed description, taken in conjunction with the accompanying drawings, which illustrate, by way of example, the principles of the disclosure.

BRIEF DESCRIPTION OF THE DRAWINGS

FIG. 8A is a perspective view depicting a distal terminal end of a delivery device;

FIG. 12 is a view of a first distal end of the delivery device;

FIG. 13 is a view of a second distal end of the delivery device;

FIG. 14 is a view of a third distal end of the delivery device;

FIG. 15 is a view of a fourth distal end of the delivery device;

FIGS. 18 A-B are perspective and exploded views, depicting various components of a shaft assembly of the delivery device;

FIG. 19 is a first view of components of a shaft assembly;

FIG. 20 is a second view of components of a shaft assembly;

FIG. 21 is a third view of components of a shaft assembly;

FIG. 22 is a fourth view of components of a shaft assembly;

FIG. 23B is a view of a first alternative arrangement of a delivery device component;

FIG. 23C is a view of a second alternative arrangement of a delivery device component;

FIG. 23D is a view of a third alternative arrangement of a delivery device component;

FIG. 23E is a view of a fourth alternative arrangement of a delivery device component;

FIG. 25A is a view of a first alternative end of a delivery device;

FIG. 25B is a view of a second alternative end of a delivery device;

FIG. 26 is a view of a first feature of one embodiment of a cutter assembly of the delivery device;

FIG. 27 is a view of a second feature of one embodiment of a cutter assembly of the delivery device;

FIG. 28A is a view of a first alternative approach to a cutter assembly;

FIG. 28B is a view of a second alternative approach to a cutter assembly;

FIG. 28C is a view of third alternative approach to a cutter assembly;

FIG. 29A is a view of a first further alternative approach to a cutter assembly;

FIG. 29B is a view of a second further alternative approach to a cutter assembly;

FIG. 29C is a view of third further alternative approach to a cutter assembly;

FIG. 30A is a view of a first structure for suture guides;

FIG. 30B is a view of a second structure for suture guides;

FIG. 30C is a view of a third structure for suture guides;

FIG. 31A is a view of a first further approach to target indicators;

FIG. 31B is a view of a second further approach to target indicators;

FIG. 31C is a view of a third further approach to target indicators;

FIG. 31D is a view of a fourth further approach to target indicators;

FIG. 32 is a view of a first feature of a suture guide;

FIG. 33 is a view of a second feature of a suture guide;

FIG. 34 is a view of a first guide structure for a suture;

FIG. 35 is a view of a second guide structure for a suture;

FIG. 36 is a view of a third guide structure for a suture;

FIG. 37 is a view of a fourth guide structure for a suture;

FIG. 38 is a first view of an approach to a suture guide;

FIG. 39 is a second view of an approach to a suture guide;

FIG. 40 is a third view of an approach to a suture guide;

FIG. 41 is a view of a first further approach to suture control;

FIG. 42 is a view of a second further approach to suture control;

FIG. 43 is a view of a third further approach to suture control;

FIG. 44 is a view of a fourth further approach to suture control;

FIG. 45 is a view of a first feature of a pusher assembly;

FIG. 46 is a view of a second feature of a pusher assembly;

FIG. 47 is a view of a third feature of a pusher assembly;

FIG. 48 is a view of a first structure facilitating anchor assembly;

FIG. 49 is a view of a second structure facilitating anchor assembly;

FIG. 51 is a view of a first alternative approach to structure for assembling an anchor;

FIG. 52 is a view of a second alternative approach to structure for assembling an anchor;

FIG. 53 is a view of a third alternative approach to structure for assembling an anchor;

FIG. 54 is a view of a fourth alternative approach to structure for assembling an anchor;

FIG. 55 is a view of a fifth alternative approach to structure for assembling an anchor;

FIG. 56 is a view of a sixth alternative approach to structure for assembling an anchor;

FIG. 60 is a view of a first alternative approach to anchor structure;

FIG. 61 is a view of a second alternative approach to anchor structure;

DETAILED DESCRIPTION OF THE PREFERRED EMBODIMENTS

Turning now to the figures, which are provided by way of example and not limitation, the present disclosure is directed to a device configured to deliver an anchor assembly within a patient's body. As stated, the disclosed apparatus can be employed for various medical purposes including but not limited to retracting, lifting, compressing, approximating, supporting or repositioning tissues, organs, anatomical structures, grafts or other material found within a patient's body. Such tissue manipulation is intended to facilitate the treatment of diseases or disorders. Moreover, the disclosure has applications in cosmetic or reconstruction purposes or in areas relating the development or research of medical treatments. The present disclosure relates to U.S. Pat. No. 8,333,776, the contents of which are incorporated by reference.

In an aspect of the present disclosure, one portion of an anchor assembly or implant is positioned and implanted against a first section of anatomy. A second portion of the anchor assembly or implant is then positioned and implanted adjacent a second section of anatomy for the purpose of retracting, lifting, compressing, approximating, supporting or repositioning the second section of anatomy with respect to the first section of anatomy as well as for the purpose of retracting, lifting, compressing, approximating, supporting or repositioning the first section of anatomy with respect to the second section of anatomy. In some embodiments, both a first and second portion of the anchor assembly can be configured to accomplish the desired retracting, lifting, compressing, approximating, supporting or repositioning of anatomy due to tension supplied during delivery via a connector assembly affixed to the first and second components of the anchor assembly or implant. In some embodiments, both a first and second portion of the anchor assembly can be configured to maintain the desired retracting, lifting, compressing, approximating, supporting or repositioning of anatomy that has been accomplished using another device, such as the delivery device.

Figure 1:
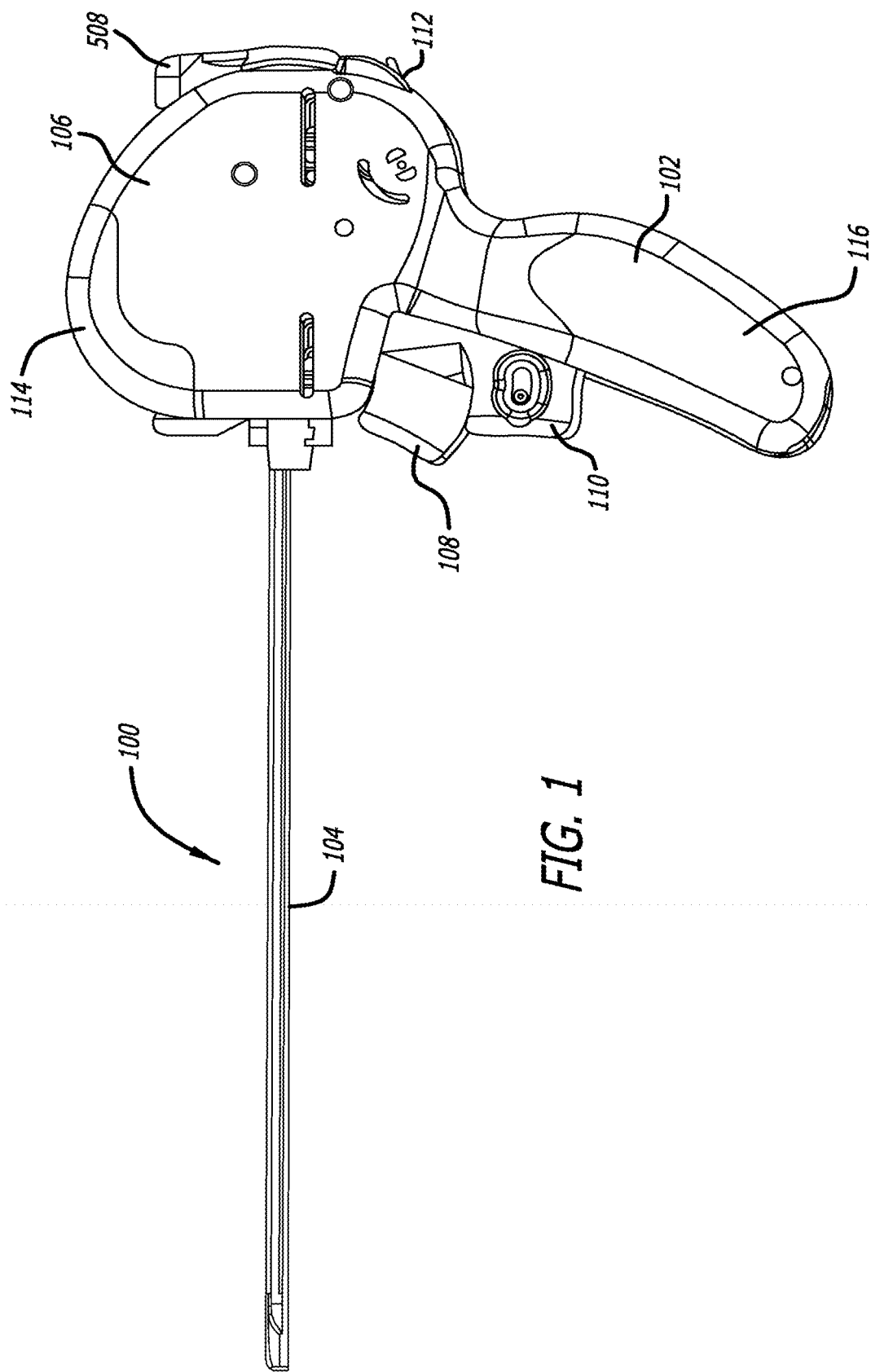
FIG. 1 is a left side view, depicting one embodiment of an anchor delivery system.
Figure 2:
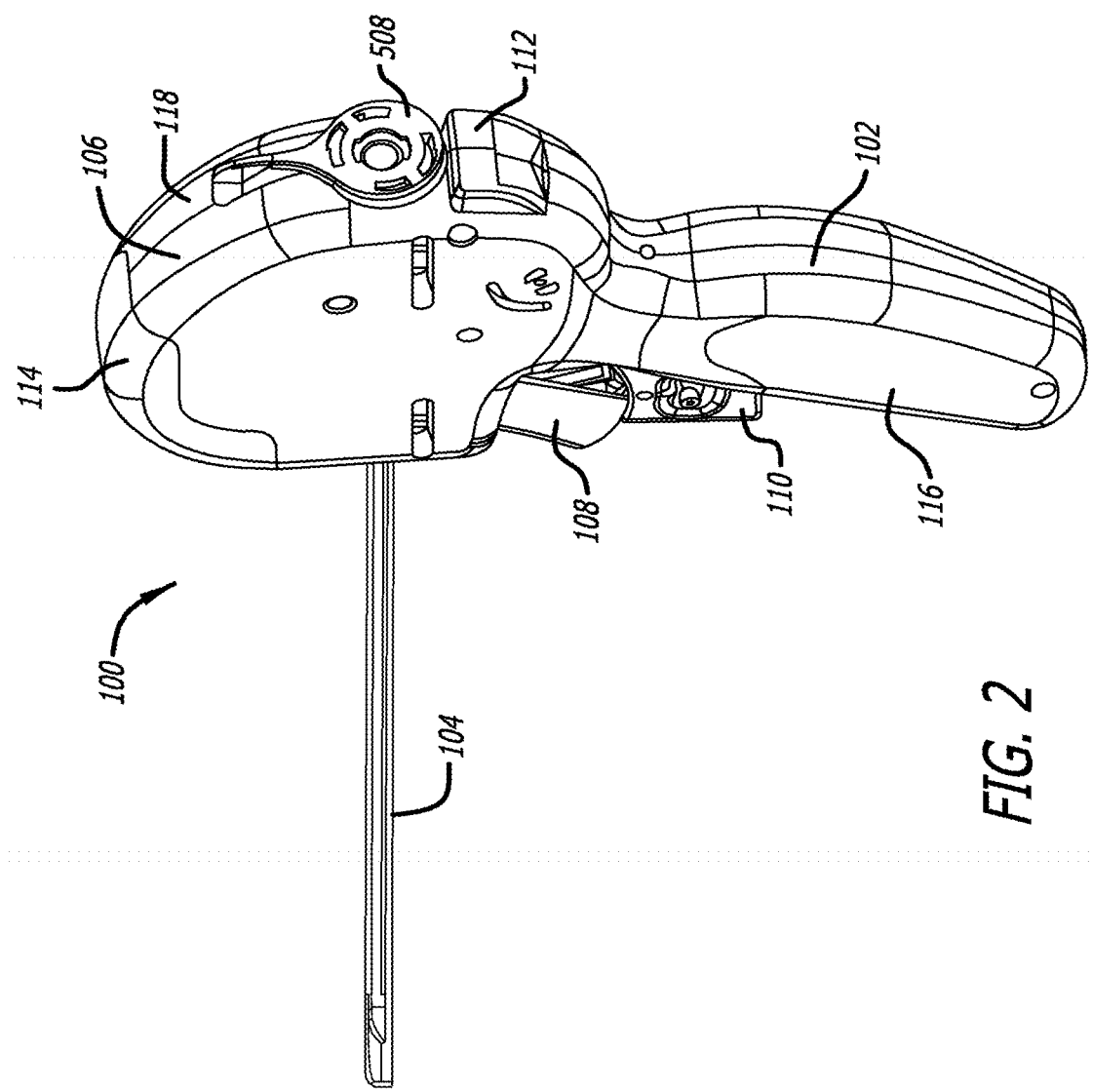
FIG. 2 is a perspective view, depicting the anchor delivery system of FIG. 1.
Figure 3:
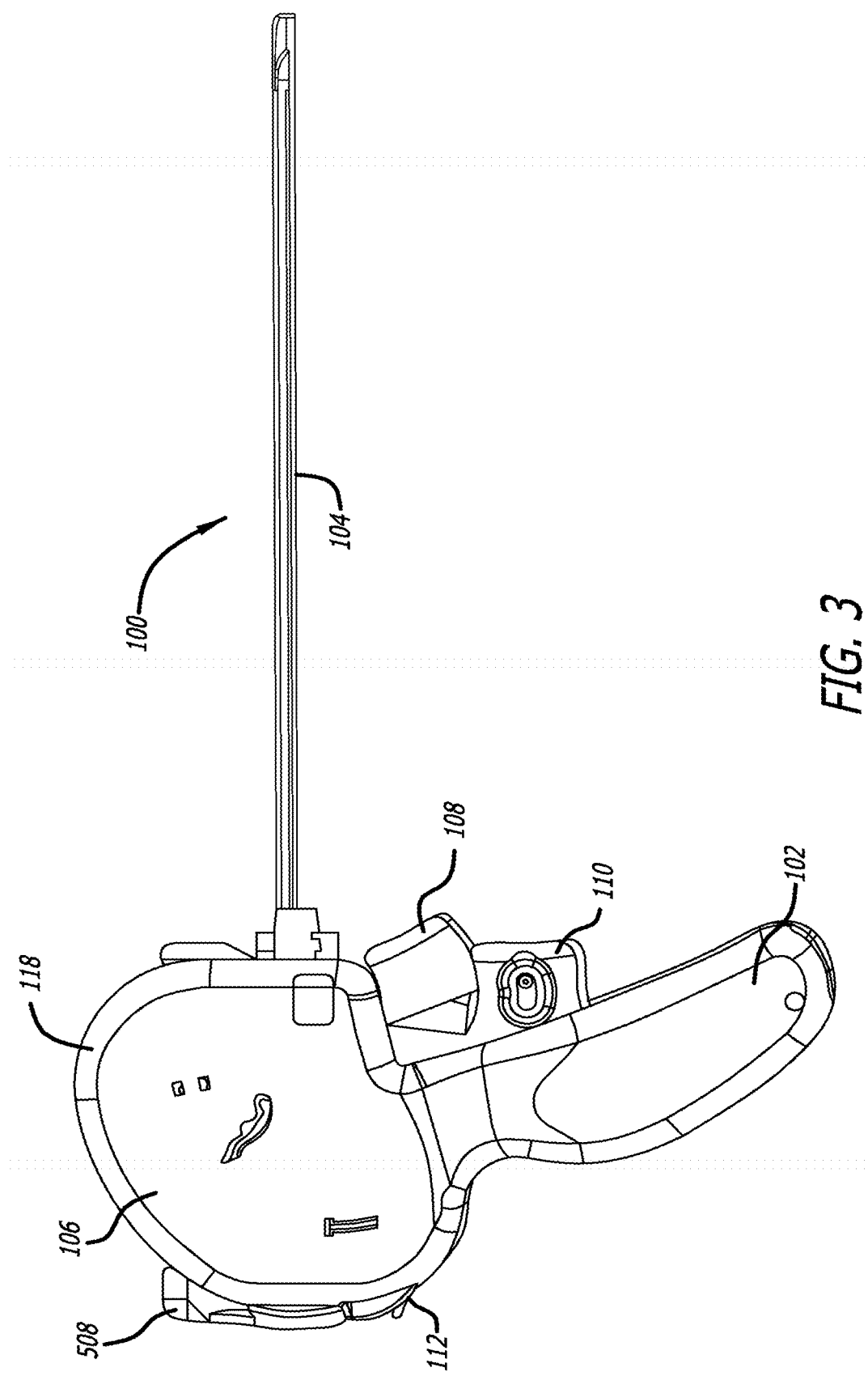
FIG. 3 is a right side view, depicting the anchor delivery system of FIG. 1.

Referring now to FIGS. 1-3, there is shown one embodiment of a delivery device 100. This device is configured to include structure that is capable of both gaining access to an interventional site as well as assembling and implanting one or more anchor assemblies or implants within a patient's body. In one embodiment, the device 100 is configured to assemble and implant a single anchor assembly or implant, but the device can be configured to implant a plurality of anchor assemblies. The device is further contemplated to be compatible for use with a 19 F or 20 F sheath. The device additionally includes structure configured to receive a conventional remote viewing device (e.g., an endoscope) so that the steps being performed at the interventional site can be observed.

Prior to use of the present device 100, a patient typically undergoes a five day regiment of antibiotics. A local anesthesia can be employed for the interventional procedure. A combination of an oral analgesic with a sedative or hypnotic component can be ingested by the patient. Moreover, topical anesthesia such as lidocaine liquids or gel can be applied to the bladder and urethra.

The anchor delivery device 100 includes a handle assembly 102 connected to an elongate tissue access assembly 104. The elongate tissue access assembly 104 houses components employed to construct an anchor assembly and is sized to fit into a 19 F or 20 F cystoscopic sheath for patient tolerance during a procedure in which the patient is awake rather than under general anesthesia. The tissue access assembly is stiff to allow manual compression of tissue at an interventional site by leveraging or pushing the handle assembly 102.

The anchor delivery device 100 further includes a number of subassemblies. A handle case assembly 106 including mating handle parts which form part of the handle assembly 102. The handle assembly 102 is sized and shaped to fit comfortably within an operator's hand and can be formed from conventional materials. Windows can be formed in the handle case assembly 106 to provide access to internal mechanisms of the device so that a manual override is available to the operator in the event the interventional procedure needs to be abandoned.

In one embodiment, the delivery device 100 is equipped with various activatable members which facilitate assembly and delivery of an anchor assembly at an interventional site. A needle actuator 108 is provided and as described in detail below, effectuates the advancement of a needle assembly (loaded with a first component of an anchor assembly) to an interventional site. In a preferred embodiment, the needle assembly has a needle that moves through a curved trajectory and exits the needle housing in alignment with a handle element, and in particular embodiments, in alignment with the grip. In various other embodiments, the needle housing is oriented such that the needles exits the housing at either the two o'clock or ten o'clock positions relative to a handle grip that is vertical. A needle retraction lever assembly 110 is also provided and when actuated causes the needle assembly to be withdrawn and expose the first anchor component. This action and the structure involved is also described in detail below. Finally, the delivery device 100 is equipped with a rear or proximal anchor actuator assembly 112 which as fully described below, upon actuation, accomplishes assembly of a second component to the anchor assembly and release of the anchor assembly at the interventional site.

Figure 4:
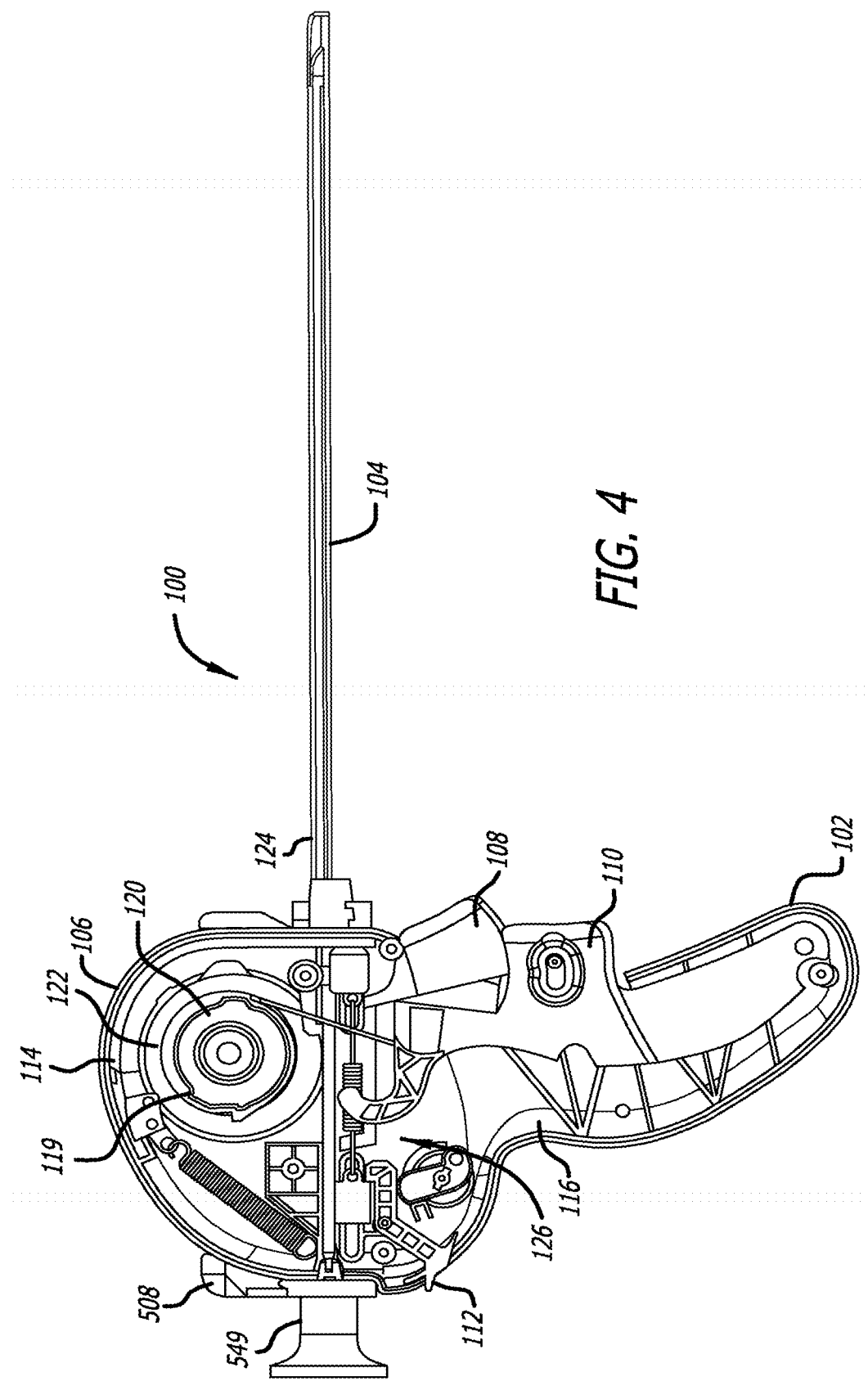
FIG. 4 is a side view, depicting the anchor delivery system of FIG. 3 with a portion of the casing removed and including a scope.
Figure 5:
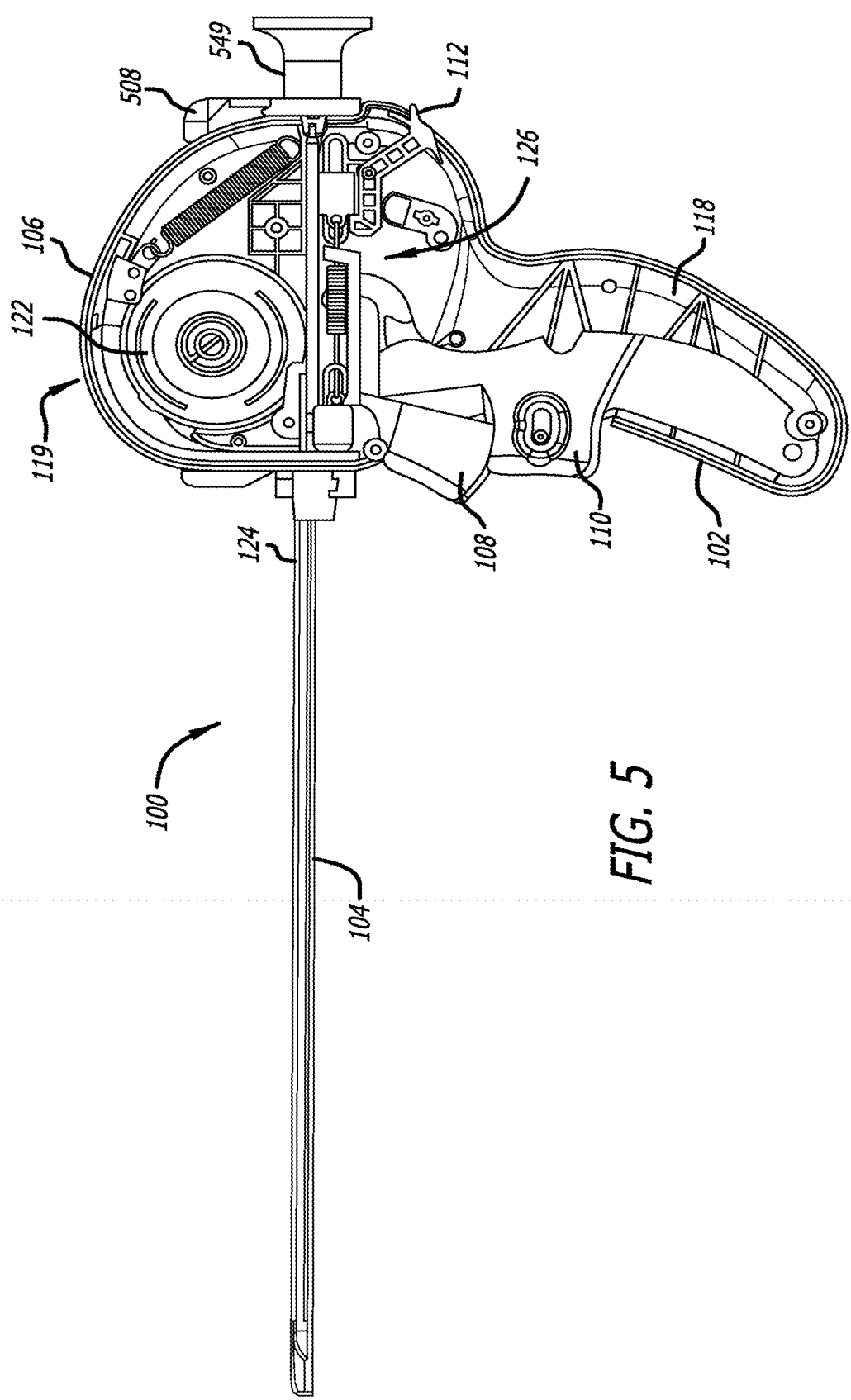
FIG. 5 is a left side view, depicting the anchor delivery device of FIG. 1 with a portion of the casing removed and including a scope.

Turning now to FIGS. 4-5 in addition to FIGS. 1-3, a number of the subassemblies of the delivery device 100 are introduced. In the embodiment depicted, the case assembly 106 has three mating parts, a left top case 114, a left bottom case 116, and a right case 118. It is within the scope of the present disclosure that the case assembly be made of a variety of numbers of parts. In addition to mating to enclose subassemblies, the case parts also include structural features for providing rigidity and support for the enclosed components.

Housed within the case assembly 106 are a distal anchor delivery mechanism 119 including a needle spool assembly 120 and a suture spool assembly 122 (referred to interchangeably herein as connector spool assembly 122). The rotational axes of the needle spool assembly and suture spool assembly are the same. A shaft assembly 124 includes a portion residing within the case assembly 106 and a portion extending from a forward end of the case assembly. Attached to and operatively associated with the shaft assembly 124 is a proximal anchor drive assembly 126. The drive assembly 126 is also housed within the case assembly 106. FIGS. 4 and 5 illustrate the juxtapositional relationships of the various subassemblies.

Figure 6:
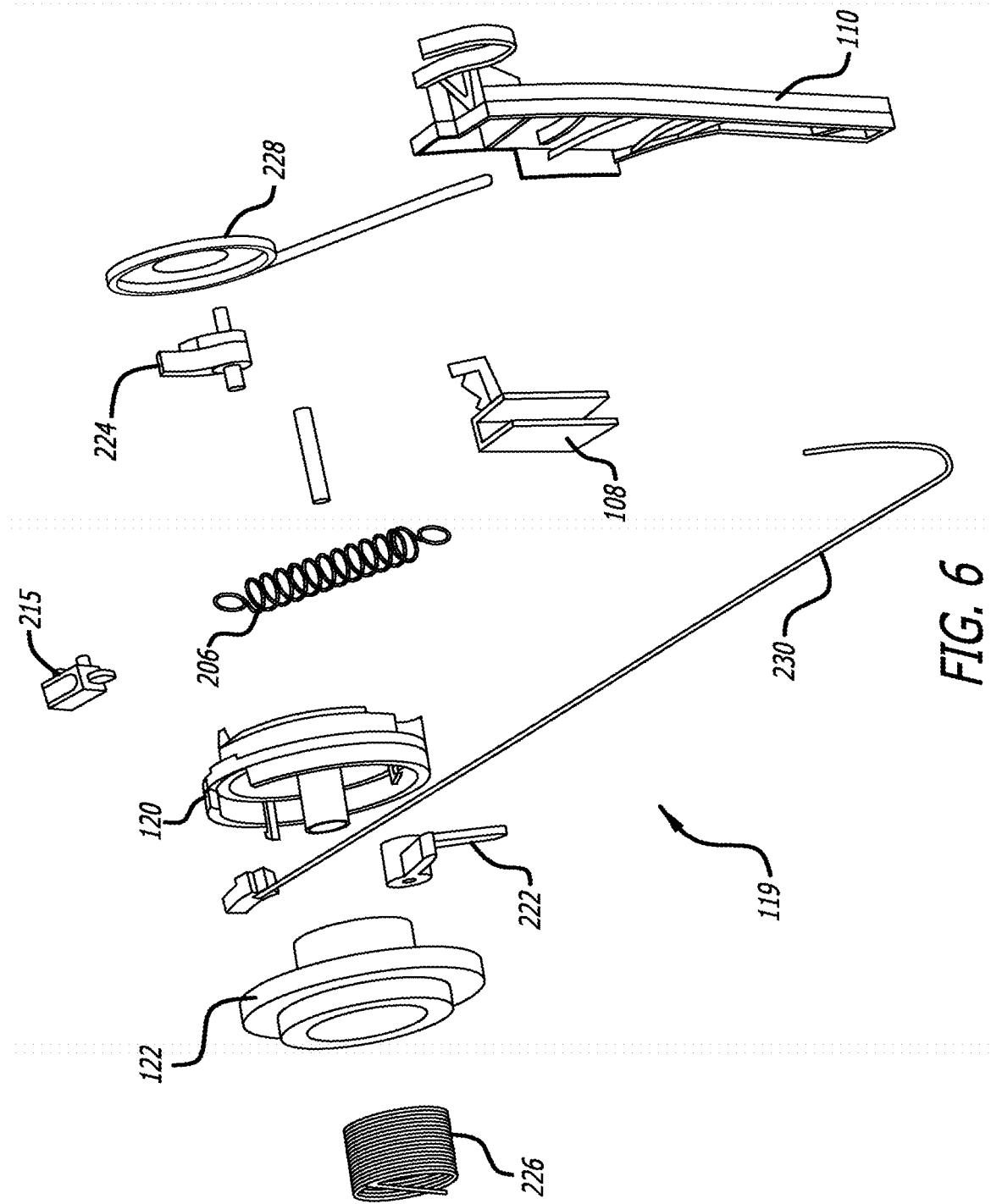
FIG. 6 is an exploded view, depicting components of a distal anchor delivery assembly.

With reference to FIG. 6, details concerning an embodiment of the structure of a distal anchor delivery mechanism 119 are presented. As described further below, the needle spool assembly 120 cooperates with the needle actuator 108 and needle retraction lever 110 to advance and then withdraw a needle assembly at an interventional site.

The needle spool assembly 120 is a generally disc-shaped structure having a number of landings and projections for engaging and receiving various structures of the distal anchor delivery mechanism 119.

A needle deploy spring 206 functions to rotate the needle spool 120 (referred to interchangeable herein as connector spool 120) and to project a tip of the needle through tissue with force and speed. One end of the deploy spring 206 is attached to the device casing and the opposite end is engaged with a shuttle 215. The shuttle 215, in turn, is operatively and releasably associated with the needle spool assembly 120. In one approach, it is contemplated that the device 100 be configured so that the needle is deployed to a single depth to pierce through a predominant population of urethral-prostatic distances in patients having an enlarged prostate.

The assembly further includes a needle deploy pawl 222 which is operatively associated with the needle actuator 108. As shown and described below, the needle actuator pivots the needle deploy pawl 222 away from engagement with the needle spool assembly 120, thereby permitting rotation of the same. The rotation of the needle spool assembly 120 is accomplished by forces generated by the deploy spring 206.

An unsheathing pawl 224 is also provided and configured at one end to engage the needle spool 120. At another end of the unsheathing pawl 224 there is structure configured to engage the suture spool assembly 122 (described below) to thereby fix its rotational position while the needle spool assembly 120 rotates. A tension spring 226 is positioned within a center bore of the suture spool 122 to provide tension to a connector or suture projecting from the suture spool 122. A lever lock and tape 228 is also provided to lock the lever 110 until after actuation of the needle actuator 108. The lever lock and tape 228 has a central axis or rotating point which is common with that of the needle spool 120 and suture spool 122 assemblies and also functions to retract a needle assembly upon depression of the lever 110. Also shown in FIG. 6 is the needle assembly 230.

Figure 7:
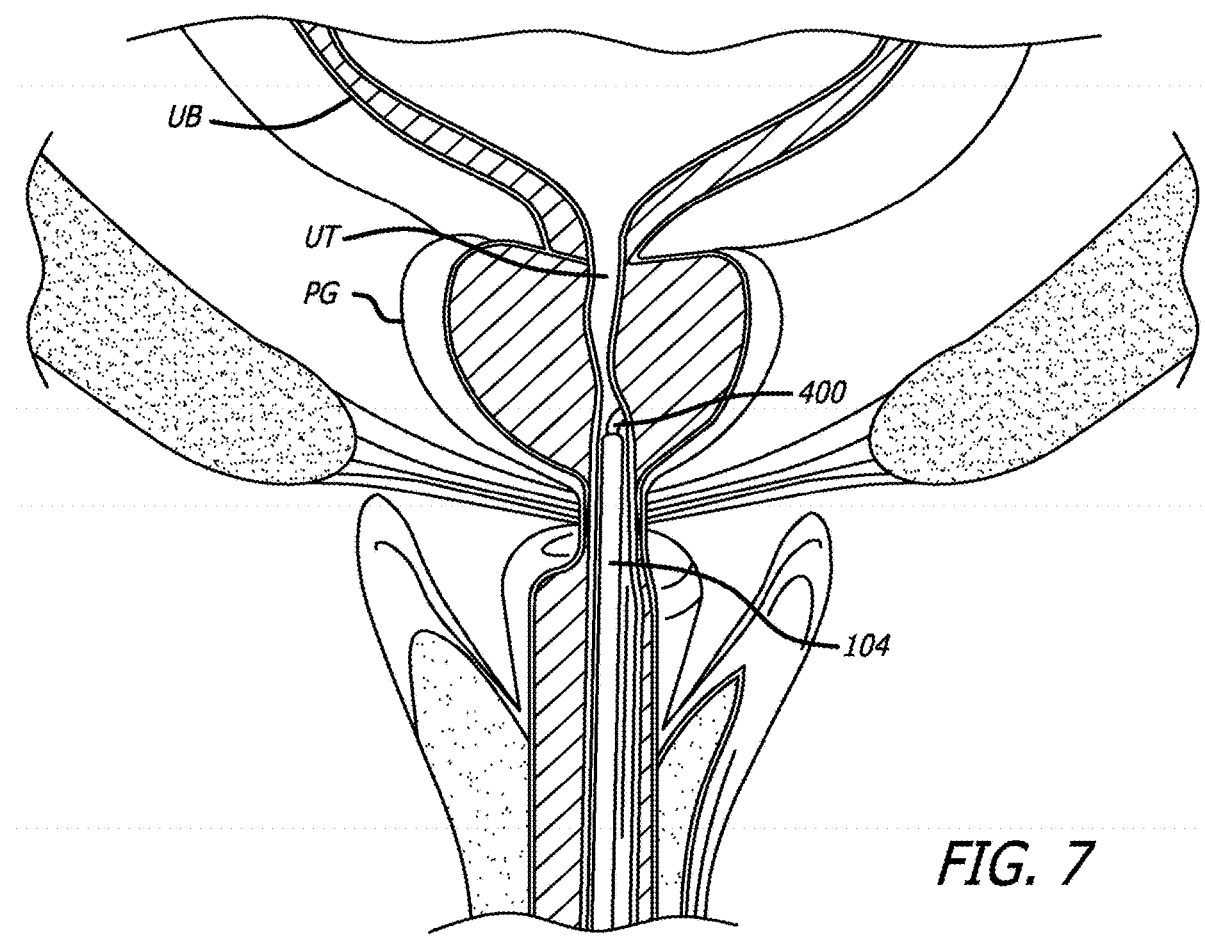
FIG. 7 is a cross-sectional view, depicting a first step involving an interventional procedure.
Figure 8B:
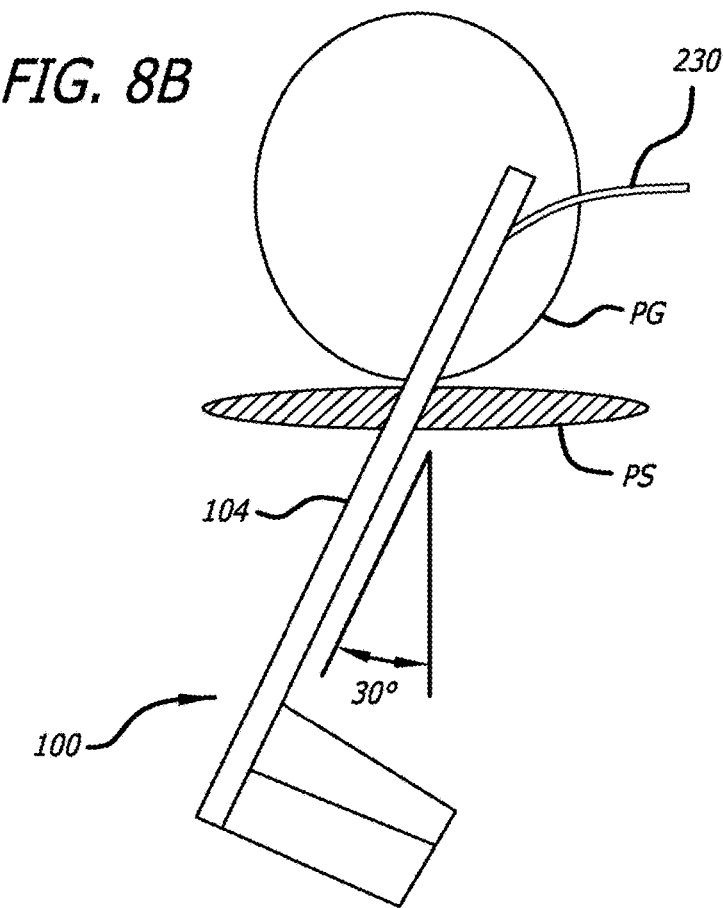
FIG. 8B is a schematic representation approximately in coronel plane, illustrating the angling of the anchor delivery tool within anatomy.
Figure 8C:
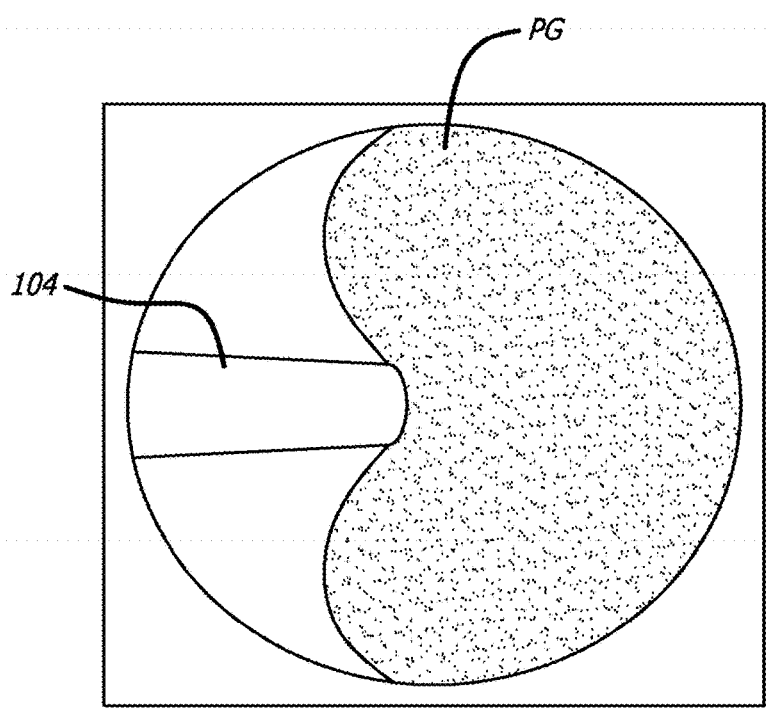
FIG. 8C is an enlarged view, depicting proper placement of treatment structure against tissue anatomy.

In one particular, non-limiting use in treating a prostate (See FIG. 7), the elongate tissue access portion 104 of a delivery device is placed within a urethra (UT) leading to a urinary bladder (UB) of a patient. In one approach, the delivery device can be placed within an introducer sheath (not shown) previously positioned in the urethra or alternatively, the delivery device can be inserted directly within the urethra. When employing an introducer sheath, the sheath can be attached to a sheath mount assembly (described below). The patient is positioned in lithotomy. The elongate portion 104 is advanced within the patient until a leading end 400 thereof reaches a prostate gland (PG). In a specific approach, the side(s) (i.e., lobe(s)) of the prostate to be treated is chosen while the device extends through the bladder and the device is turned accordingly. The device is first positioned at the bladder neck and then refracted approximately 1 cm while keeping the device parallel to the prostatic fossa and preserving mucosa. As shown in FIG. 8A, when so placed, the distal end 240 of the needle assembly is withdrawn within the leading end 400 of the device. The distal end of the elongate portion can be used to push the urethra into the prostate gland. The inside of the prostate gland (i.e., adenoma) is spongy and compressible and the outer surface (i.e., capsule) of the prostate gland is firm. By the physician viewing with the endoscope, he/she can push the urethra into the prostate gland compressing the adenoma and creating the desired opening through the urethra. To accomplish this, the physician rotates the tool anterior between 9 and 10 o'clock for the patient's side left lobe and between 2 and 3 o'clock for the patient's side left lobe. The physician then pivots the tool laterally about the pubic symphysis PS, generally about 20 to 30 degrees relative to the patient's midline (See FIG. 8B which depicts an image approximately in coronal plane). Viewing through the endoscope, the physician wants to have about the same amount of tissue protruding on both sides of the elongate shaft (See FIG. 8C).

Figure 9:
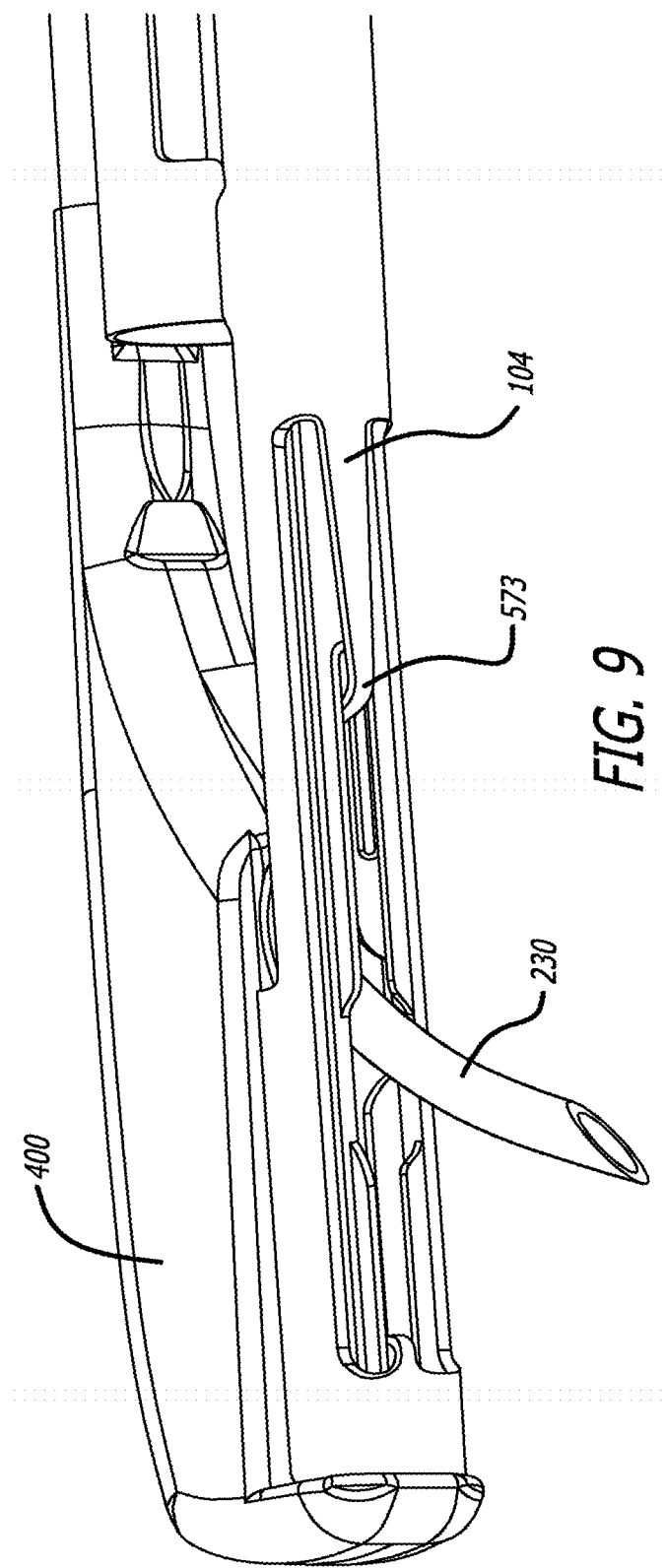
FIG. 9 is a perspective view in partial cross-section, depicting advancement of a needle assembly.
Figure 10:
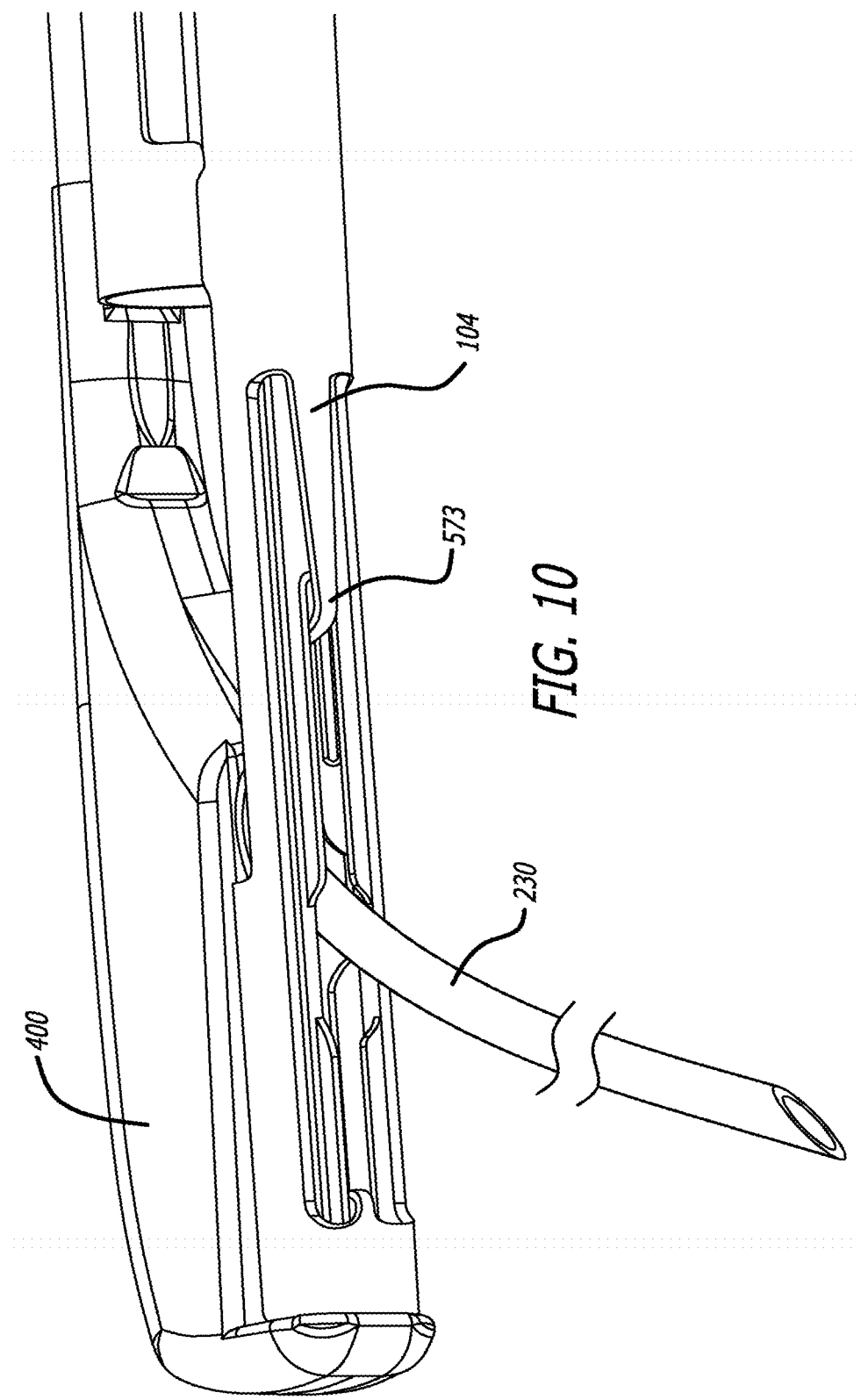
FIG. 10 is a perspective view in partial cross-section, depicting advancement of a needle assembly.
Figure 11:
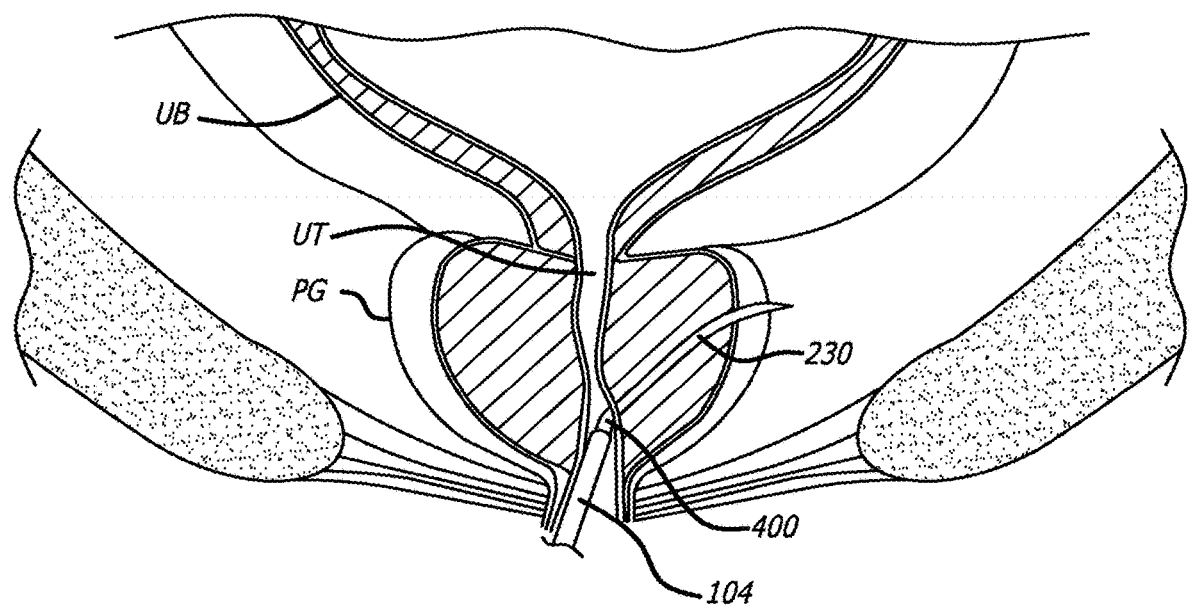
FIG. 11 is a cross-sectional view, depicting advancement of a needle assembly at an interventional site.

At the leading end 400 of the delivery device, as shown in FIGS. 9 and 10, the needle assembly is intended to be advanced from within the elongate member 104. As is to be appreciated, the needle is ejected in a direction commensurate with the direction the handle assembly extends. Moreover, the needle assembly can be configured so that it curves back toward the handle as it is ejected. In use in a prostate intervention (See FIG. 11), the needle assembly 230 is advanced through and beyond a prostate gland (PG). To facilitate the same, the device can be pivoted 20° to 30° laterally (pivoting about pubic symphisis). Alternatively, or additionally, the leading end 400 of the delivery device can be configured to articulate to thereby provide angles from which the needle can be ejected. In one approach, the elongate portion could be held in a straight configuration during advancement to within the prostatic capsule, and then articulated to direct the ejection of the needle for a particular application. Additionally, the device can be rotated anteriorly to lift a prostatic lobe (as described previously). The spring deployment helps to ensure the needle tip passes swiftly through the tough outer capsule of the prostate without "tenting" the capsule or failing to pierce the capsule. In an alternate embodiment, the needle could be manually deployed by the user. In one approach, the needle 230 is made from Nitinol tubing and can be coated with Parylene N. Such a coating helps compensate for frictional or environmental losses (i.e. wetness) which may degrade effectiveness of needle penetration.

Further, it is contemplated that the delivery device can be configured to include structure (trigger or lever) which advances the needle a fixed distance, stopping before it contacts the urethra wall. This will allow the physician to see exactly where the needle will exit the device and help with implant placement. An additional pull of the trigger, for example, could then deploy the needle through tissue. Various alternative energy sources can be employed to advance the needle, such as pneumatic or electrical based systems.

Figure 12:
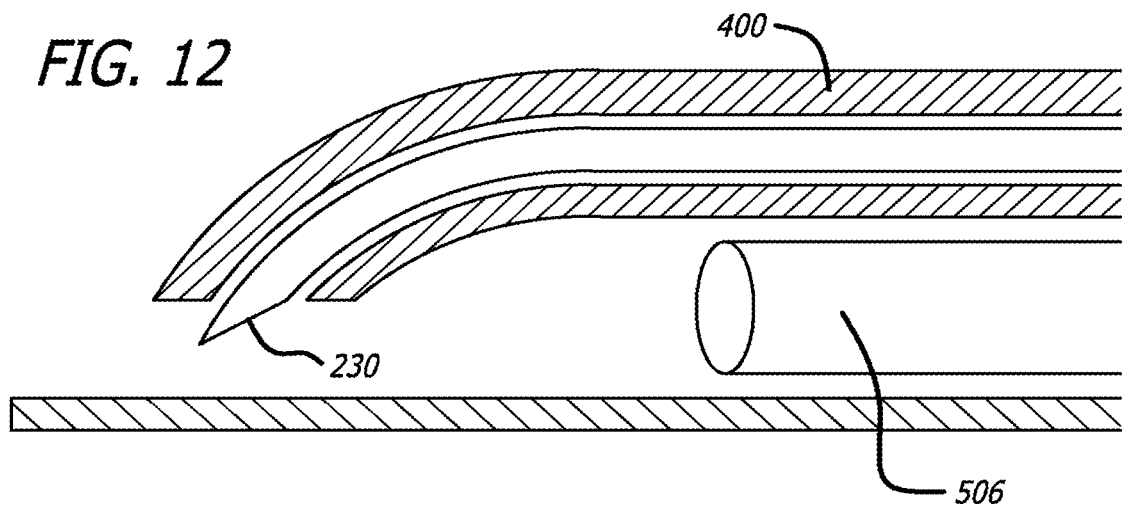
FIGS. 12-15 are cross-sectional views, depicting a distal end of the delivery device.
Figure 13:
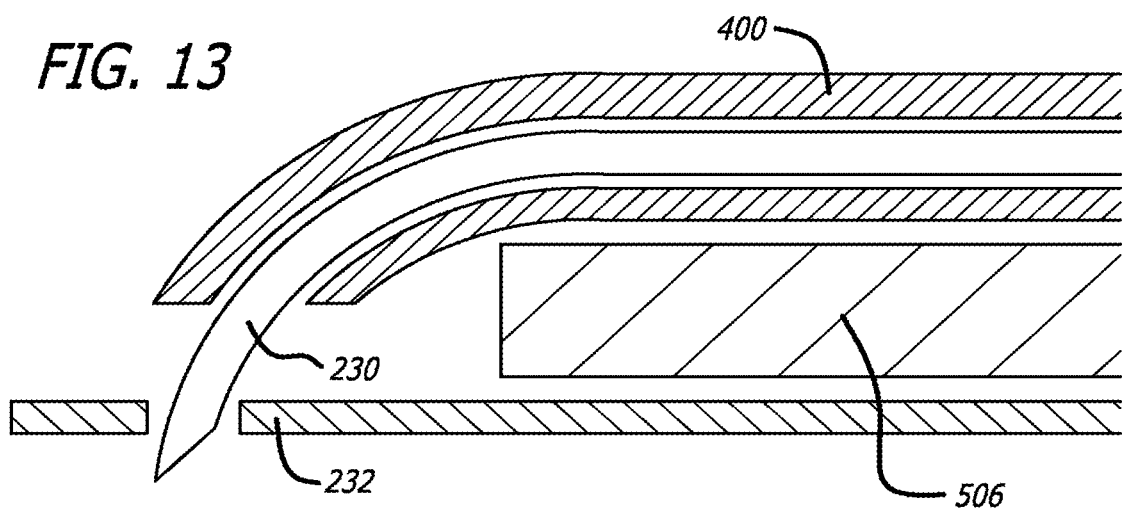

Further, as shown in FIGS. 12 and 13, the delivery system can be configured to include visual or geometric clues to aid in targeting needle trajectory. One approach (FIG. 12) is to change a start position of the needle 230. Rather than being completely housed within the needle enveloping structures of the leading end 400, a start position of the needle 230 can be such that a tip of the needle is visible through a scope lumen 506 prior to activation of the trigger or handle assembly. Another approach (FIG. 13) could involve changing leading end 400 geometry to facilitate direct viewing of the needle 230 by the user. A guide 232 can be added to the leading end 400 to constrain the needle to exit the leading end 400 in a generally perpendicular manner. With needle so traveling, its trajectory could be more intuitive to the user.

Figure 14:
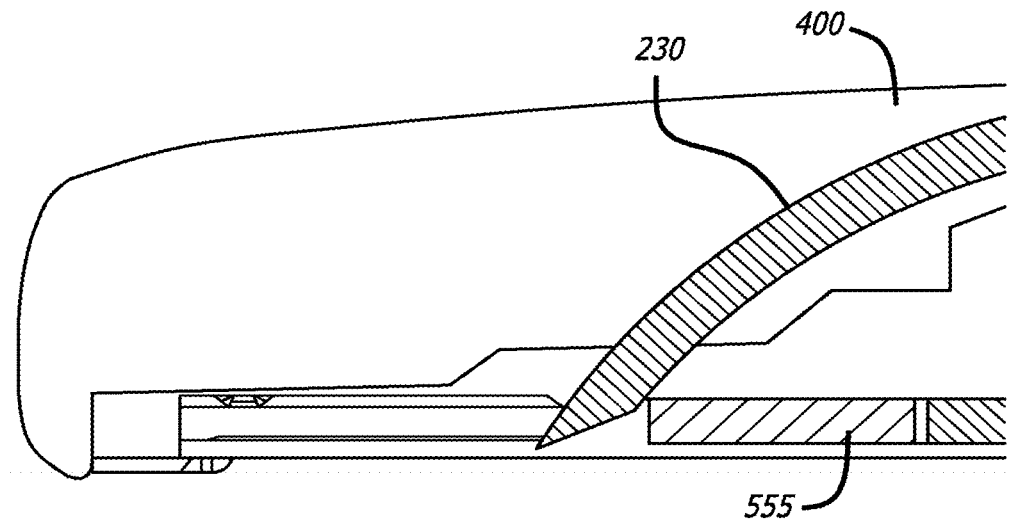
Figure 15:
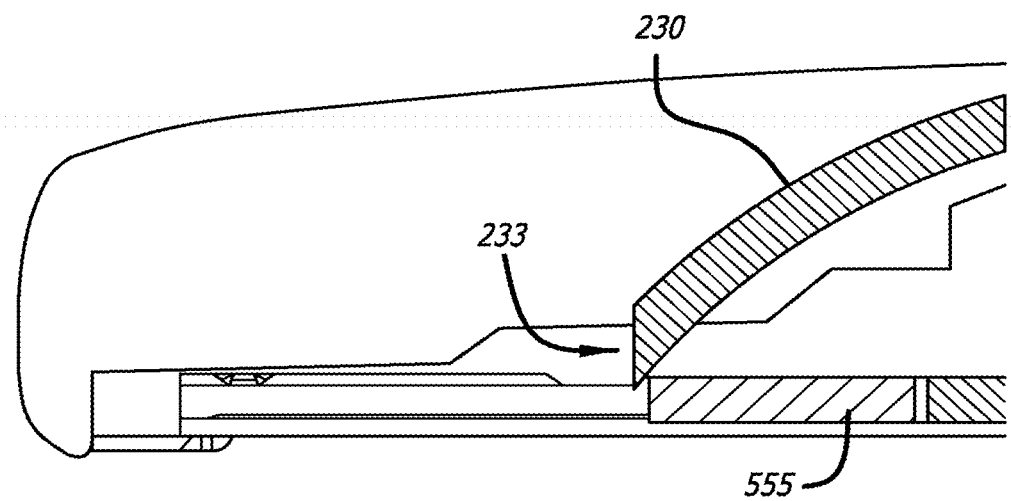

With reference to FIGS. 14 and 15, additional features can be incorporated into the delivery device to advance unwanted interference to proper device function. The start position of the needle 230 can be modified such as by adding a feature to the needle spool so that the needle tip starts in the path of a proximal anchor 555, thus removing a concern that the anchor 555 might strike the needle 230 during needle deployment (FIG. 14). In this approach, a finger projection 573 (See FIGS. 9 and 10) can be removed from the delivery device. Here, the proximal anchor 555 start position can be moved closer to the needle exit window which removes a tendency for the anchor to float when it is advanced for assembly. The stroking action to move the anchor 555 into place can be reduced. Furthermore, the needle orientation can be rotated 180° so that the needle tip is on an inside radius of the curve directing the ejection of the needle (FIG. 15). This approach may be desirable where there is a concern that the needle bevel 233 might not pass through the anchor path within the cover of the elongate portion 104, and still allows the anchor 555 to block the needle exit when sliding forward.

Figure 16:
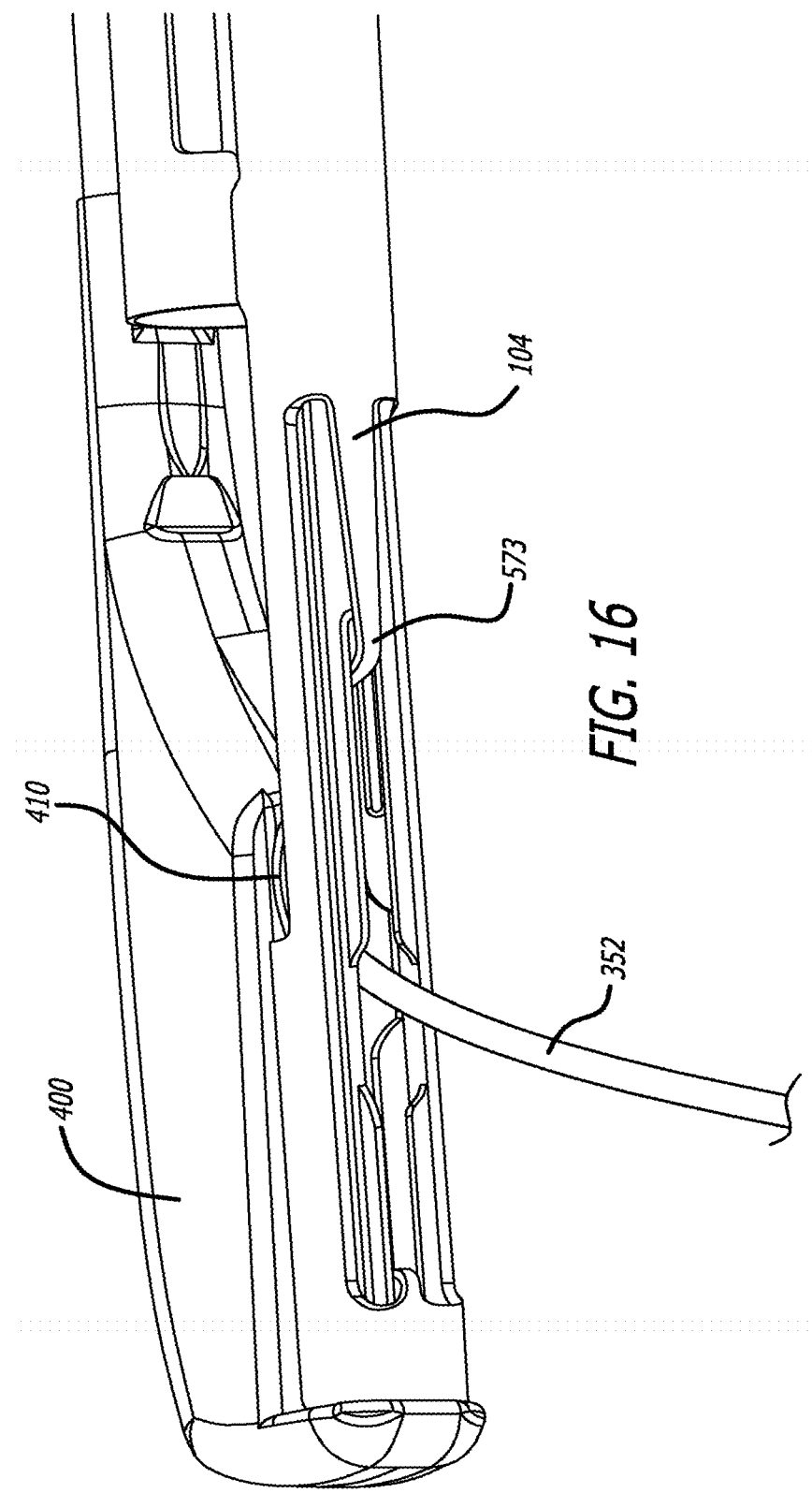
FIG. 16 is a perspective view, depicting withdrawal of a needle assembly leaving a connector element.
Figure 17:
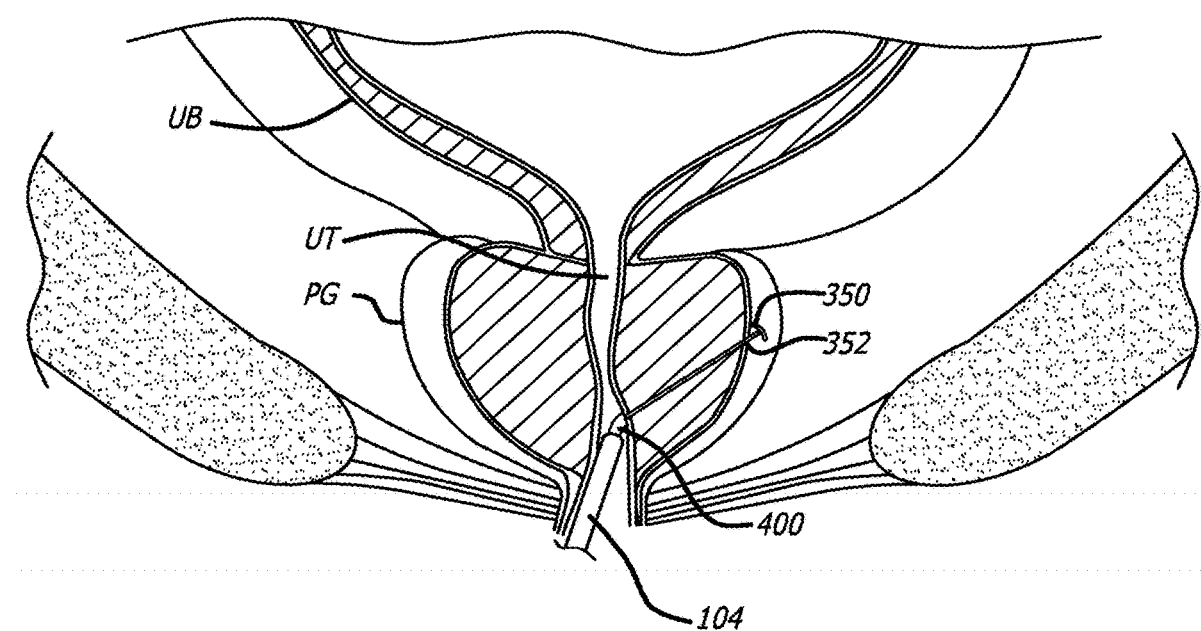
FIG. 17 is a cross-sectional view, depicting delivery of a first component of an anchor assembly at an interventional site.

After complete depression of the needle actuator 108 and the unlocking of the needle retraction lever 110, the needle retraction lever 110 can be actuated. When so actuated, there is a withdrawal of the needle assembly 230, leaving the connector 352 of an anchor assembly in an extended position (See FIG. 16). In one particular approach, it is contemplated that the connector 352 can be a suture or other elongate structure sized to be slidably received in the needle 230. Further, the diameter or profile of the connector can be made to be supported by the needle 230 lumen inside diameter rather than other device structure (i.e. hollow tip of device). This arrangement can facilitate more connector control when it is presented to a proximal anchor. Further it is contemplated that the connector 352 can include an over jacket (not shown) to reduce elasticity of the connector along a proximal section thereof. In one embodiment, the needle 230 is withdrawn further than its original position within the device pre-deployment. When extended, the connector 352 extends through the needle window and is centered by suture guide structure. As shown in FIG. 17, in a prostatic interventional procedure, the same results in delivering a first or distal anchor component attached to the connector 352 beyond an outer surface of a prostate gland (PG) with the connector 352 within a penetration tract in the prostate gland extending toward the terminal end 400 of a delivery device.

A tensioning spring provides the tension forces which helps to ensure the distal anchor is pulled back into firm contact with a desired tissue plane such as, for example, the outer capsular surface of the prostate gland. Notably, the spring in a preferred embodiment provides a force such as up to 1-2 pounds or more of tension. In another embodiment, a spring can be used to automatically retract the needle assembly.

The timing of the needle retraction and tensioning can be accomplished through the interaction of an unsheathing pawl and a suture spool. The tensioning spring is then left to automatically provide a consistent tensioning force on a connector of an anchor assembly. Such tensioning results in seating a distal or first anchor component 350 as desired within an interventional site such as shown in FIG. 17 as well as to minimize a distance between two anchor members of an implanted anchor assembly. The tension generated after seating the anchor component 350 can be different from that during delivery of the connector of the anchor assembly.

A more detailed description of the shaft assembly now follows as does a description of the operation of the structure achieving assembly of a second or proximal anchor component to a connector of an anchor assembly and release of a complete anchor assembly at the interventional site.

Figure 18A:
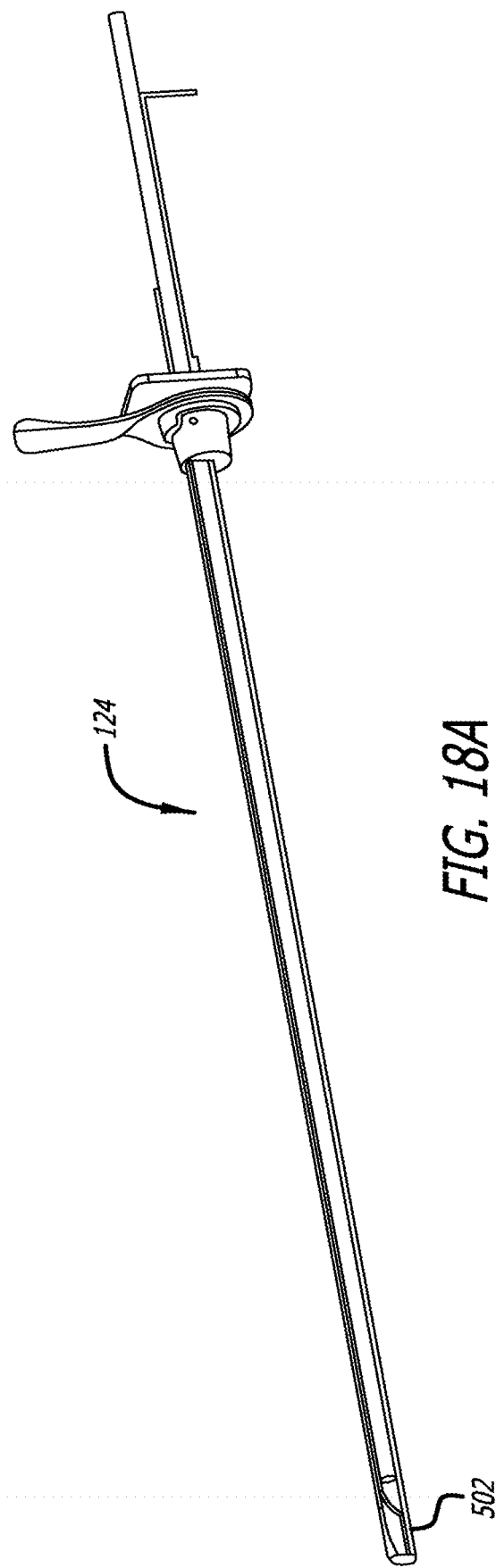
FIG. 18A is a view depicting first components of a shaft assembly of the delivery device.
Figure 18B:
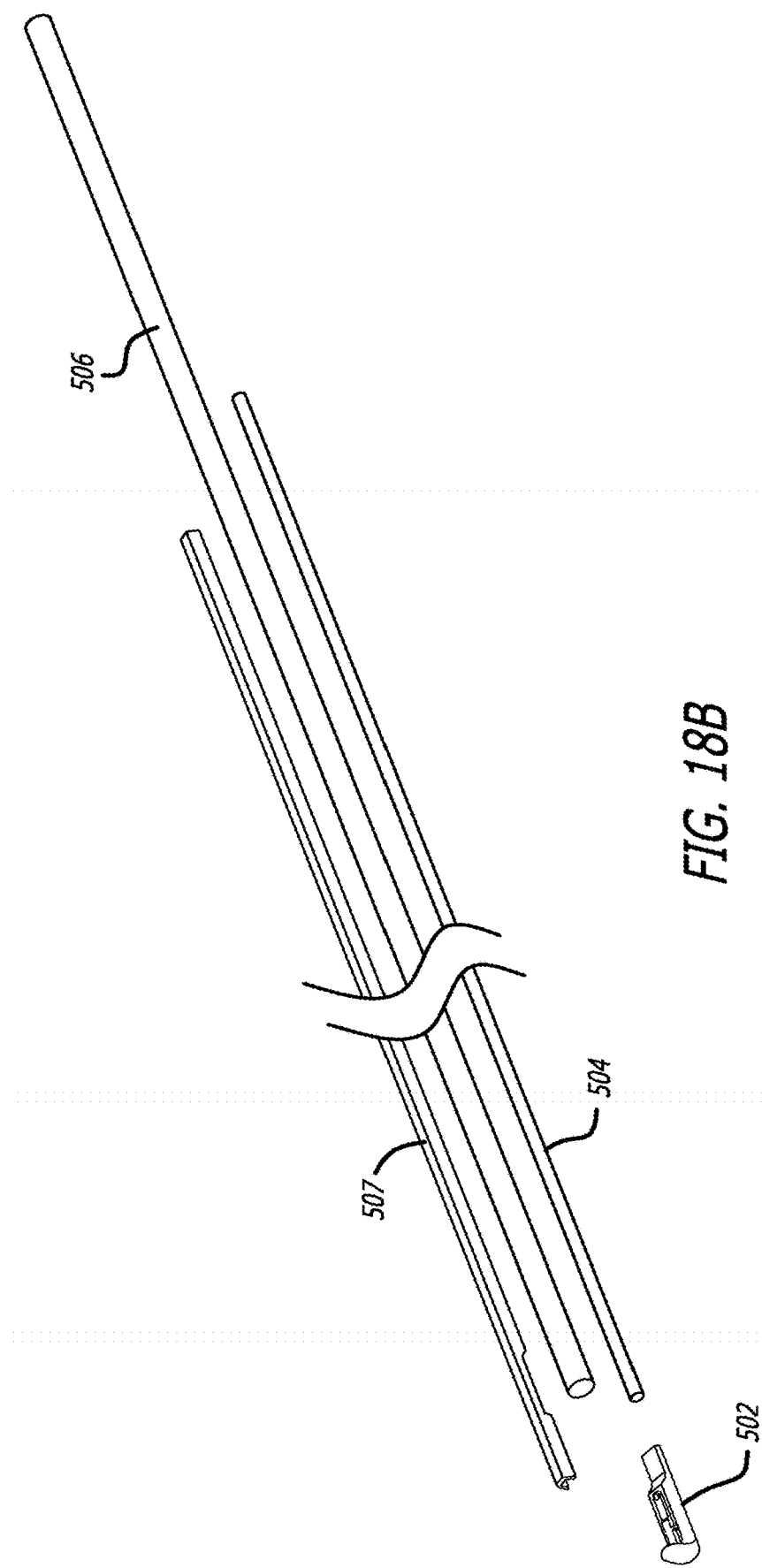
FIG. 18B is a view depicting second components of a shaft assembly of the delivery device.
Figure 19:
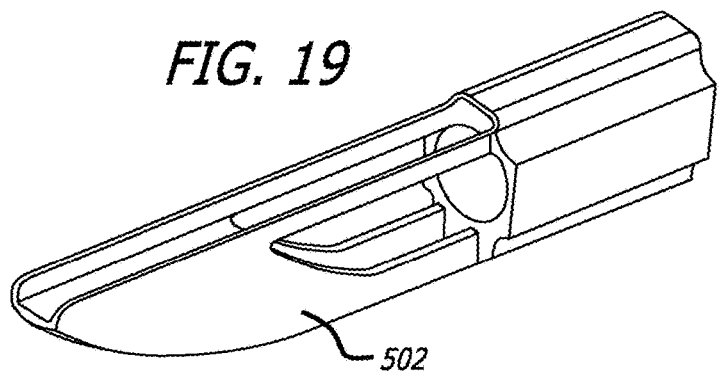
FIGS. 19-22 are perspective views, depicting components of one embodiment of a shaft assembly.
Figure 20:
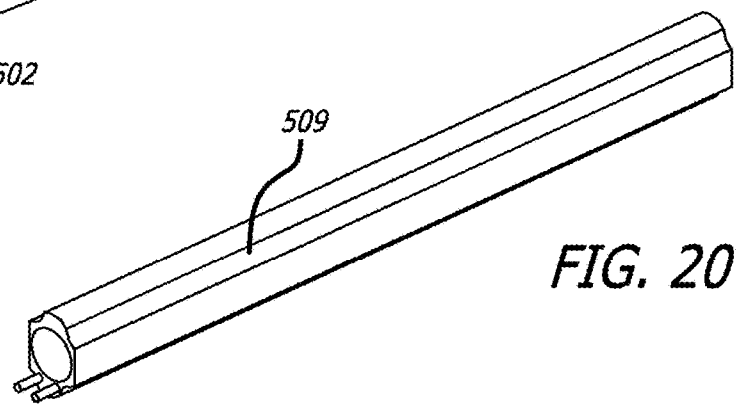
Figure 21:
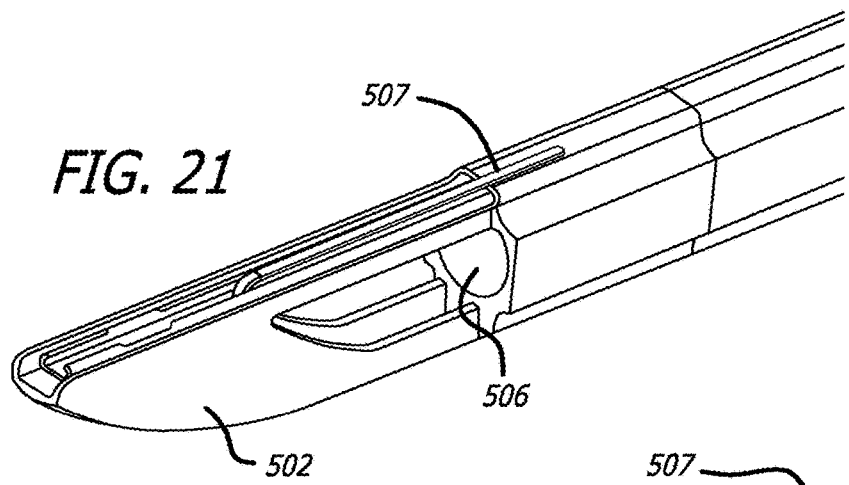
Figure 22:
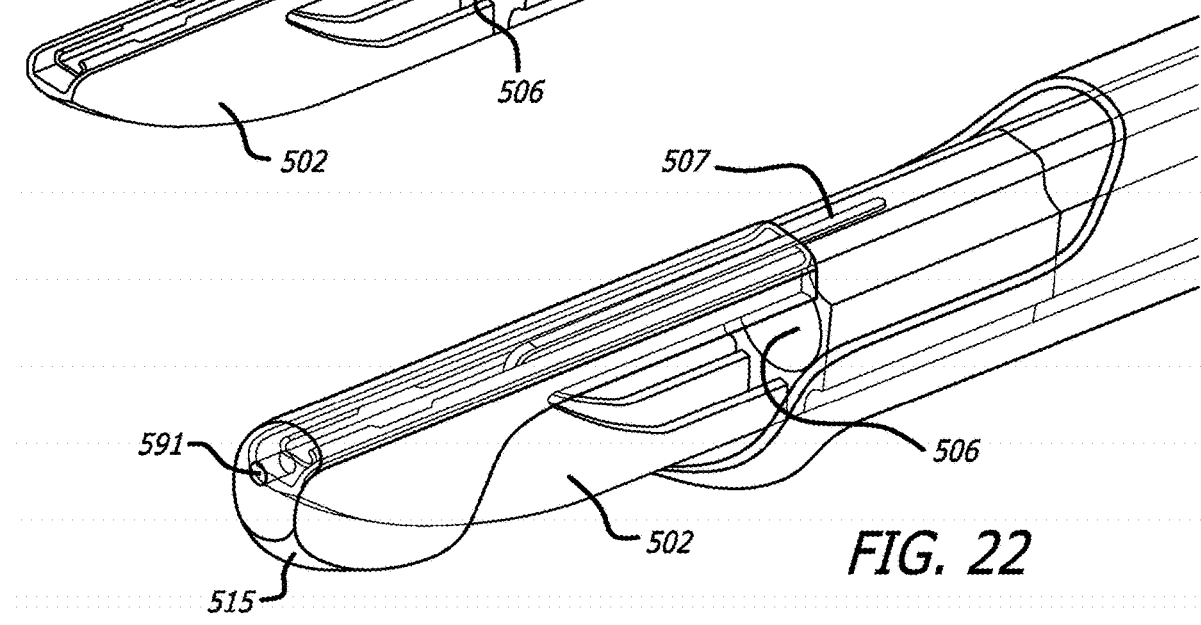

With reference to FIGS. 18A-B, there is shown an embodiment of a shaft assembly 124. Components of the shaft reside within the device case assembly 106 and include structure attached to and cooperating with proximal anchor delivery and assembly structure. A terminal end portion 400 of the shaft assembly 124 includes an atraumatic distal tip 502. Proximally located to the tip 502 is a tubular shaft assembly 504 which is sized and shaped to slidably receive the needle assembly. An internal portion of the tip 502 is curved so that a needle projecting therefrom extends in a direction generally corresponding to that of a handle element of the delivery device. Configured longitudinally adjacent the tubular shaft assembly is a scope tube 506 which is sized and shaped to receive a scope as described previously. Configured below and longitudinally adjacent the scope tube 506 is an elongate cover 507 which is sized to receive elongate portions of the cutter and pusher assemblies.

As shown in FIGS. 19-22, the shaft assembly 124 can alternatively be formed from modular pieces. For example, a telescope tube 506 can be employed as a backbone about which a molded tip 502 and a shaft extension 509 are configured. An atraumatic tip sleeve 591 can be placed over the tip 502 and an elongate cover 507 can be placed longitudinally along the shaft extension 509. This modular shaft assembly permits the use of injection molded components to form the shaft. Injection molded components are less expensive and can lead themselves to easy and quick assembly. Moreover, different materials can be chosen for the various shaft components to thereby provide desired shaft stiffness. Further, in one contemplated approach, a clear sheath hood 515 can be configured about the distal tip 502 so that a matching of a sheath and a distal portion of the device can be better accomplished.

Figure 23A:
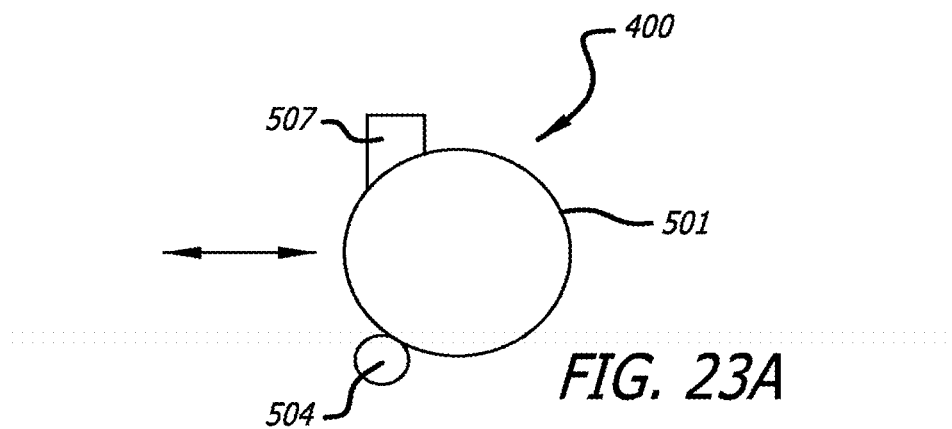
FIG. 23A is a cross-sectional view, depicting positional relationships of components of a delivery device.

Various other juxtapositional relationships between the needle tube 504, telescope tube 506 and cover 507 are contemplated. As shown in FIG. 23A, the scope 506 can be laterally offset from a centerline of the cover 502 and needle tube 504. Separate devices with opposite offsets may in fact be useful for treating patient right and patient left. This approach can be implemented in a static design or a translating mechanism could be incorporated into the delivery system to move the scope tube 506 laterally.

Figure 23B:
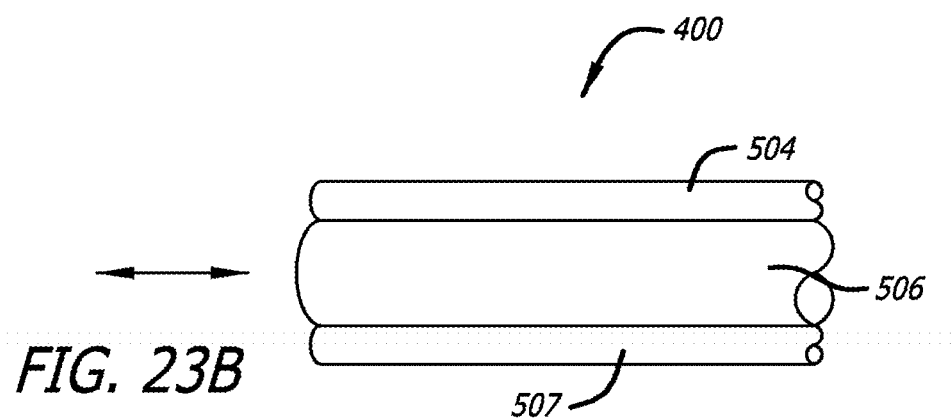
FIGS. 23B-E are side views, depicting various alternative arrangements of delivery device components.
Figure 23C:
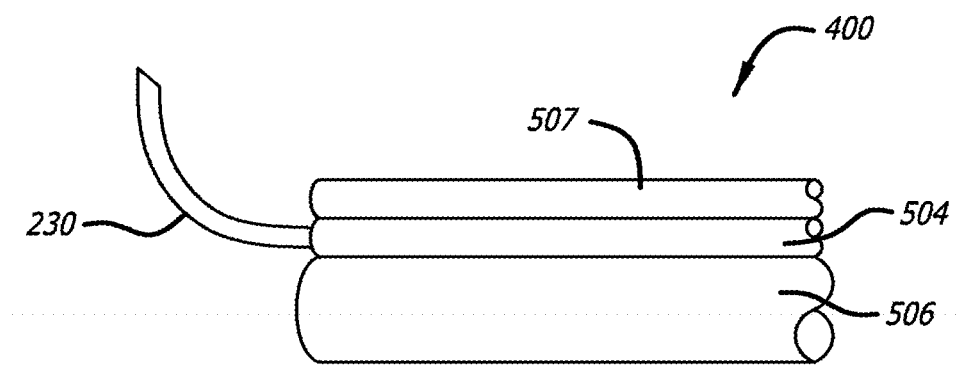
Figure 23D:
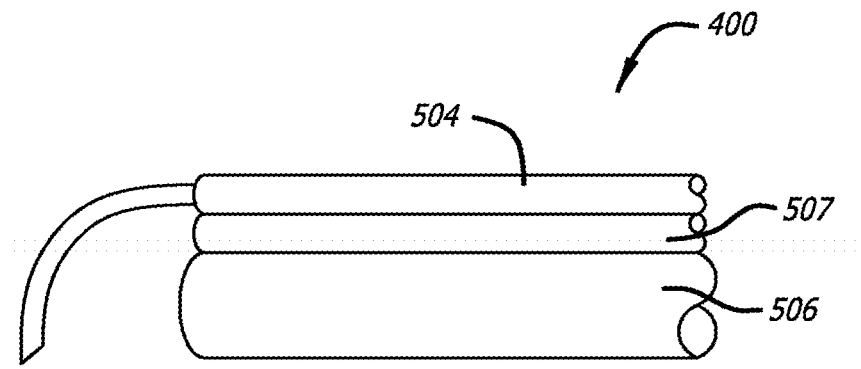
Figure 23E:
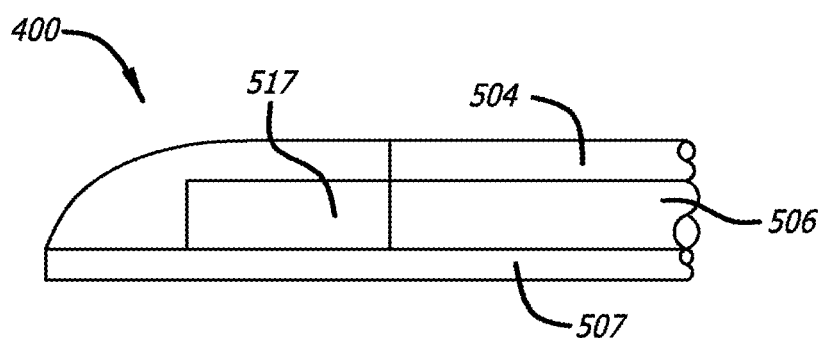

Further, as shown in FIG. 23B, a nominal position of the scope 506 relative to a needle exit could be increased to provide additional viewable area along the sides of the device shaft. Again, a translating mechanism which moves the scope axially could be employed to locate the scope as needed. Moreover, the positions of the scope tube 506 and needle tube 504 (FIG. 23C) or that of the cover 502 and scope tube 506 (FIG. 23D) could be swapped to create additional viewing areas. To make these modifications, a tighter radius needle may be required as well as changes to the terminal end 502 of the leading end 400, such as removing the curved lumen. As shown in FIG. 23E, removing the curved lumen of the top 502 could open up additional space 517 and scope visibility along a side of the device. Here also, a tighter radius needle shape set might be required to direct the needle orthogonally.

Figure 24:
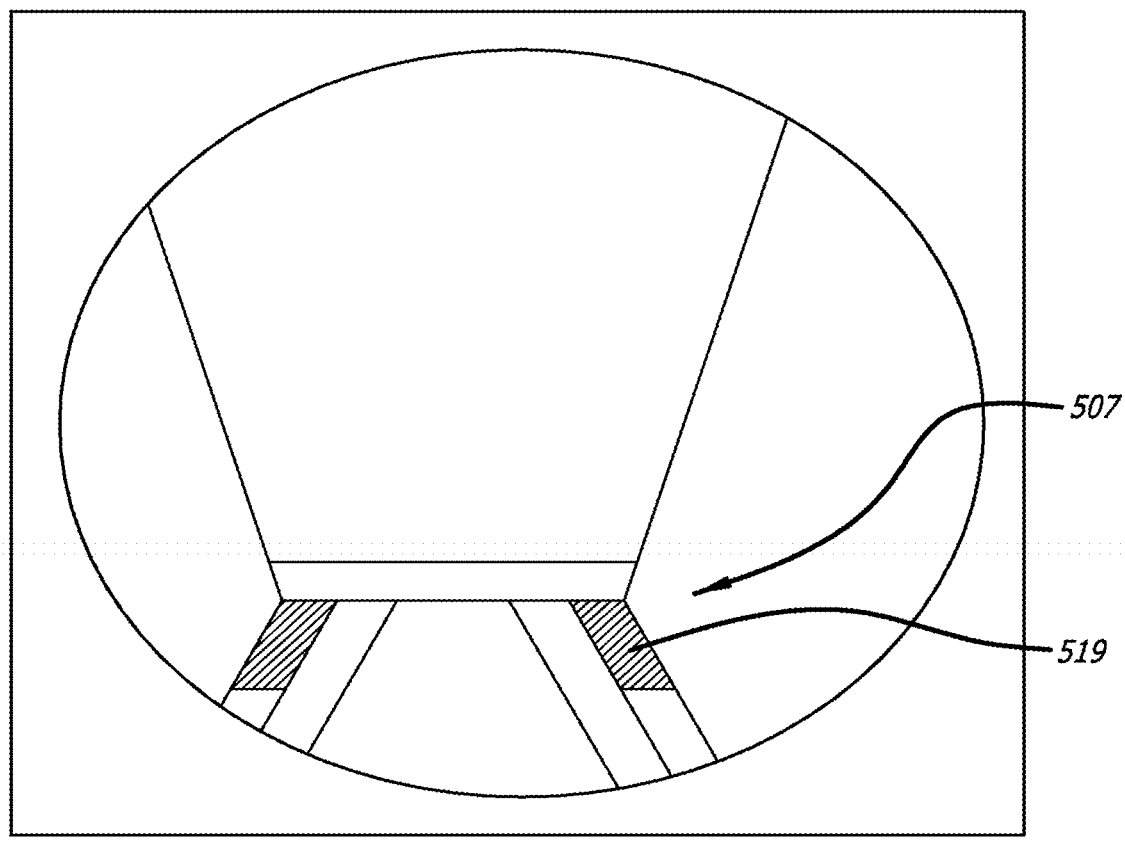
FIG. 24 is an enlarged view, depicting a visual aid for a delivery device.

As shown in FIG. 24, an atraumatic protrusion 519 can be added to the cover 507 to act as a visual indicator to where the needle will exit the leading end of the delivery device. Such protrusions 519 can be employed to displace tissue in order to produce an indentation or landmark on prostate lobes. A visual landmark is also provided in determining a location of suture deployment. The protrusions could also be formed by atraumatic tape or can be formed into a molded component and attached to or formed part of the cover 507.

Figure 25A:
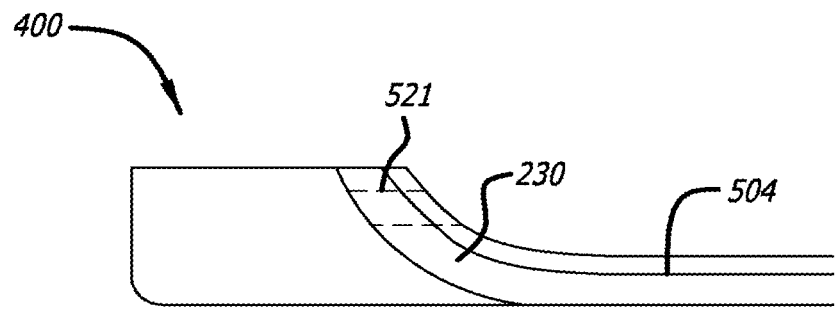
FIGS. 25A-B are side views, depicting alternative ends of a delivery device.
Figure 25B:
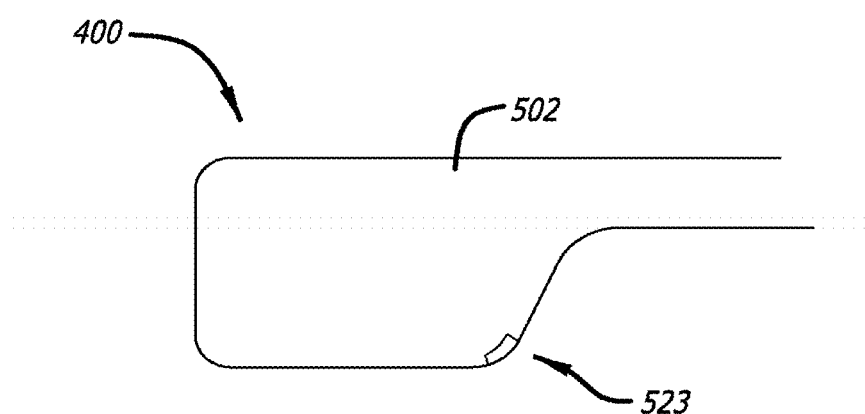

Other approaches to locate the needle upon deployment are addressed in FIGS. 25A and 25B, and to facilitate precise needle targeting. Edges can be beveled along the path where the needle is deployed to reflect light thereby highlighting the area. The suture connector could be used as a light pipe by shining light through the needle lumen or tube 504. The light would be amplified and scattered by the suture (which would be translucent) facilitating lighting up the area before and after the needle is deployed or retracted. A hole 521 can further be cut through the top of the needle lumen so that light shines through indicating the location of the needle. Further (FIG. 25B), the tip 502 can be formed from translucent material and include a nontransparent or reflective surface 523 defining a target area. It is also contemplated that a laser (not shown) or other light sources could be incorporated into the device, in combination with such reflective surface or other mirrored surfaces to direct light in a direction in which the needle is to travel.

During use of the present device, viewing of the interventional site is accomplished through a telescope which can involve a foreshortening effect in the field of view. In addition, because of the speed of the needle and the end of the tool being pressed into the tissue and the lobes protruding on each side, the operator may not know or see where the needle assembly will exit the device and/or engage tissue.

Other reflections are also contemplated so that light can be reflected back onto the connector to thus light up the area and improve visualization of the connector when the area is dark. A circular, elliptical, parabolic or straight cut can be made and provided with a reflective surface. These features can alternatively be incorporated into a cover assembly as a separate part or adhered to the cover with atraumatic tape or be part of the tape itself. The features in some embodiments take advantage of a light source associated with the viewing apparatus being employed and reflect light back providing a bright appearance. The relatively perpendicular angle of the indicators with respect to the light source results in significant contrast. In one embodiment, a small fiber optic resides in the shaft assembly, such as parallel to the cover on the outside or inside the cover parallel to the cutter, using the same light source as the endoscope/telescope. The fiber can have a right angle output so that the light shines onto the tissue. Thus, the cover can also include indicators on faces generally perpendicular to the viewing orientation. It is to be noted that such indicators can assume various shapes such as rectangles and arrows.

Figure 26:
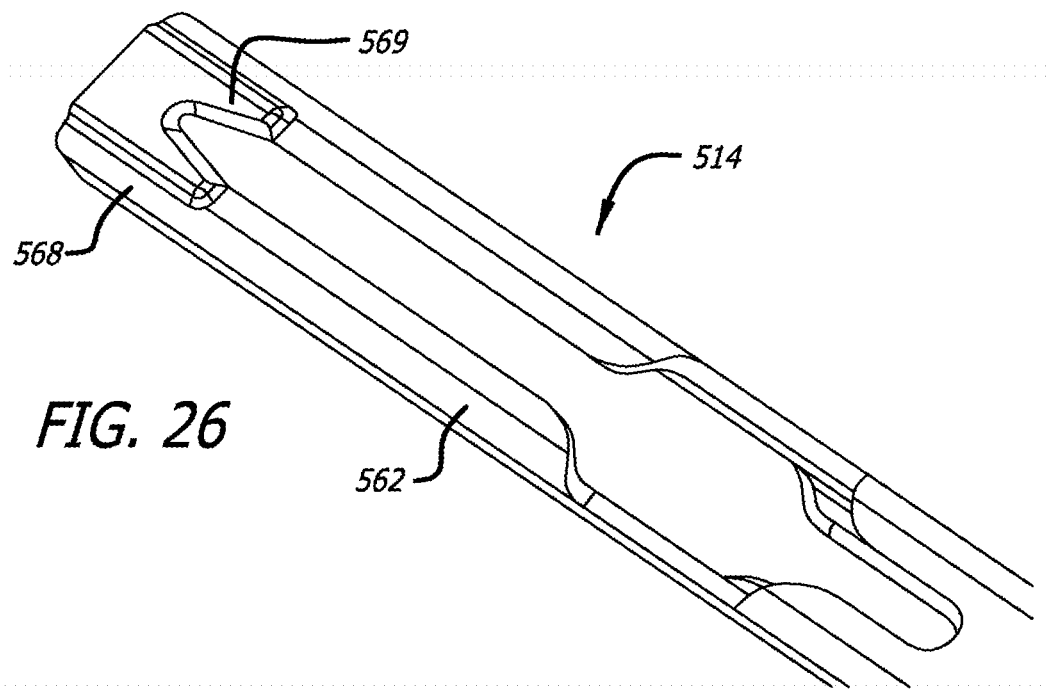
FIGS. 26-27 are perspective views, depicting features of one embodiment of a cutter assembly of the delivery device.
Figure 27:
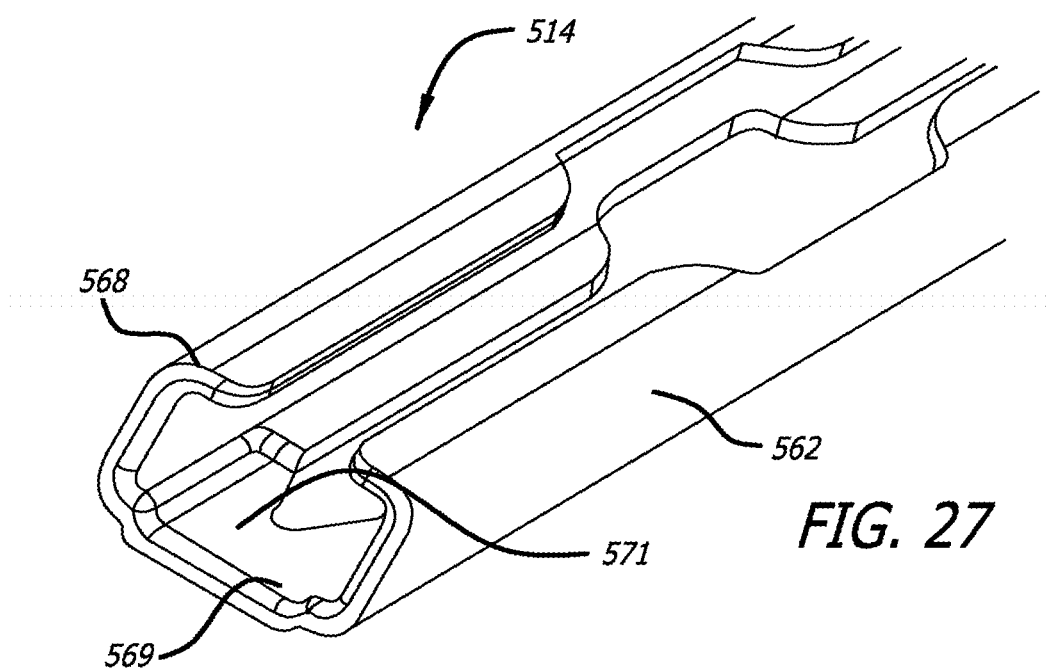
Figure 45:
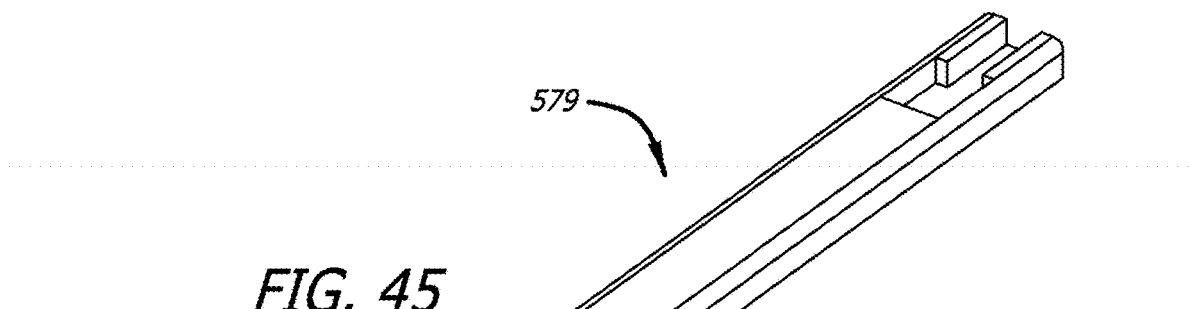
FIGS. 45-47 are perspective views, depicting features of a pusher assembly.

As best shown in FIGS. 26 and 27, an embodiment of the cutter assembly 514 includes elongate cutter tube 562. A distal end 568 of the cutter tube 562 is configured with a blade 569 so that once the cutter assembly 514 is withdrawn, the blade can sever as desired a connector of an anchor assembly. In one particular embodiment, the cutter 514 can be formed from ground 17-4PH stainless steel blank. Various structures are contemplated for incorporation into the cutter assembly to facilitate a clean severing of a connector as well as to aid in assembling a proximal component of an anchor assembly to the connector. For example, as best seen in FIG. 45, the cutter blade 569 includes a coined out underside that is intended to be offset from a bottom side of a proximal anchor by about 0.0035+0.0010 inches to cut a nominal 0.015 inch diameter connector. In this way, the proximal anchor can exit a cutter without deforming or compressing a suture or connector tag, and the strength of the connector to anchor connection is maintained.

The cutter 514 can define a generally rectangular elongate single body that can be formed by stamping and bending. An interior of the body is sized and shaped to receive a proximal anchor component 550. A proximal end portion of the cutter 564 can further include anti-buckling tabs and extensions intended to snap fit to a cutter block (not shown).

Figure 28A:
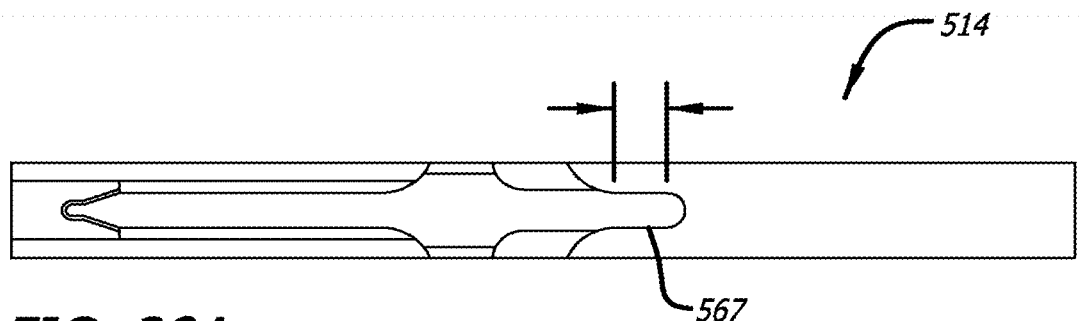
FIGS. 28A-C are top views, depicting alternative approaches to a cutter assembly.
Figure 28B:
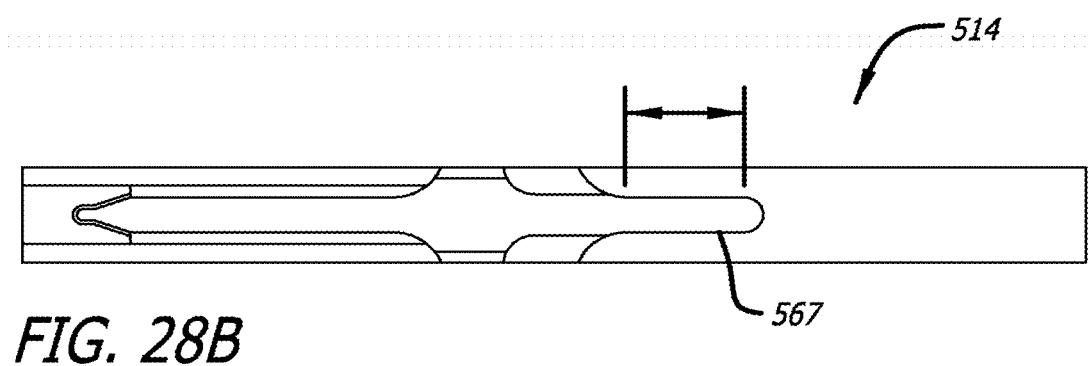
Figure 28C:
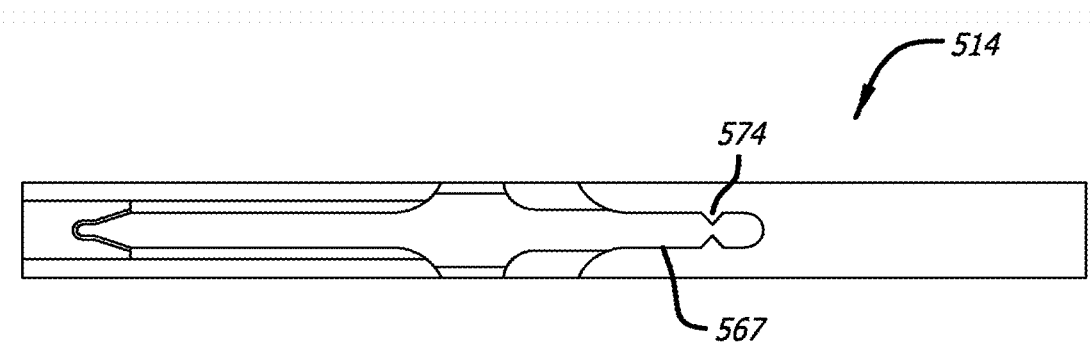

Alternative approaches to the cutter 514 are addressed in FIGS. 28A-C in order to ensure that the proximal anchor captures suture with a high tensile strength. In one approach a suture keyhole 567 can be increased in length from 0.030 inches to 0.060 inches, for example to assist clinicians with proper suture position for successful proximal anchor deployment. With the suture positioned at the inception of the keyhole site 567, the proximal anchor will capture the suture once the anchor is deployed. A suture indicating feature 574 can further be added to the keyhole 567 to indicate when the suture is in the correct, pre-urethral activation position.

Figure 29A:
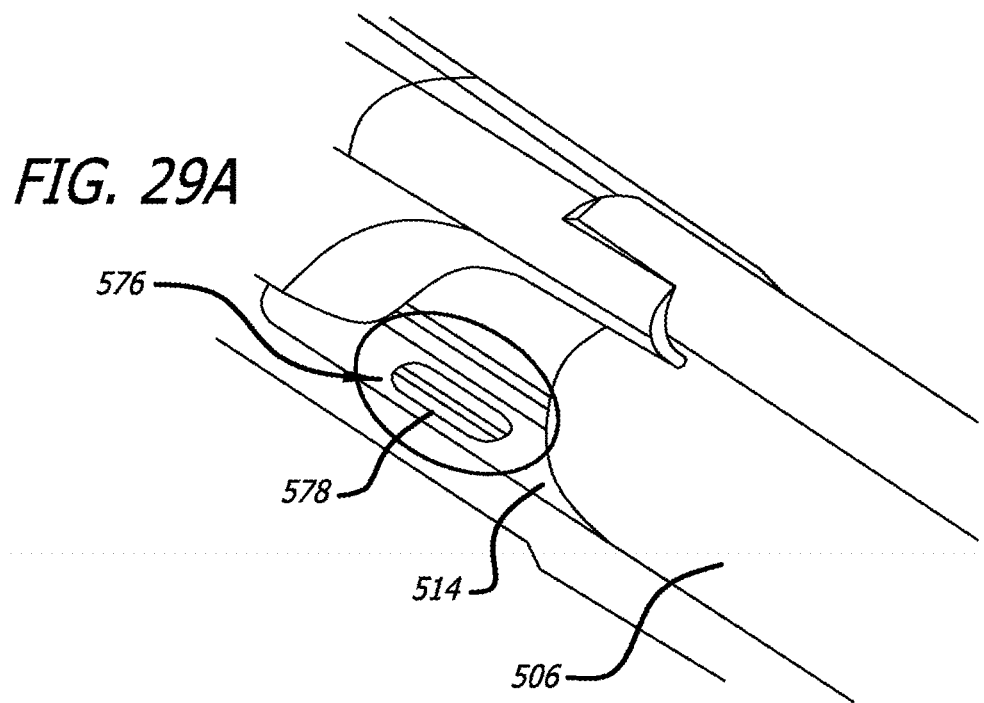
FIGS. 29A-C are perspective and top views, depicting further alternatives to cutter assemblies.
Figure 29B:
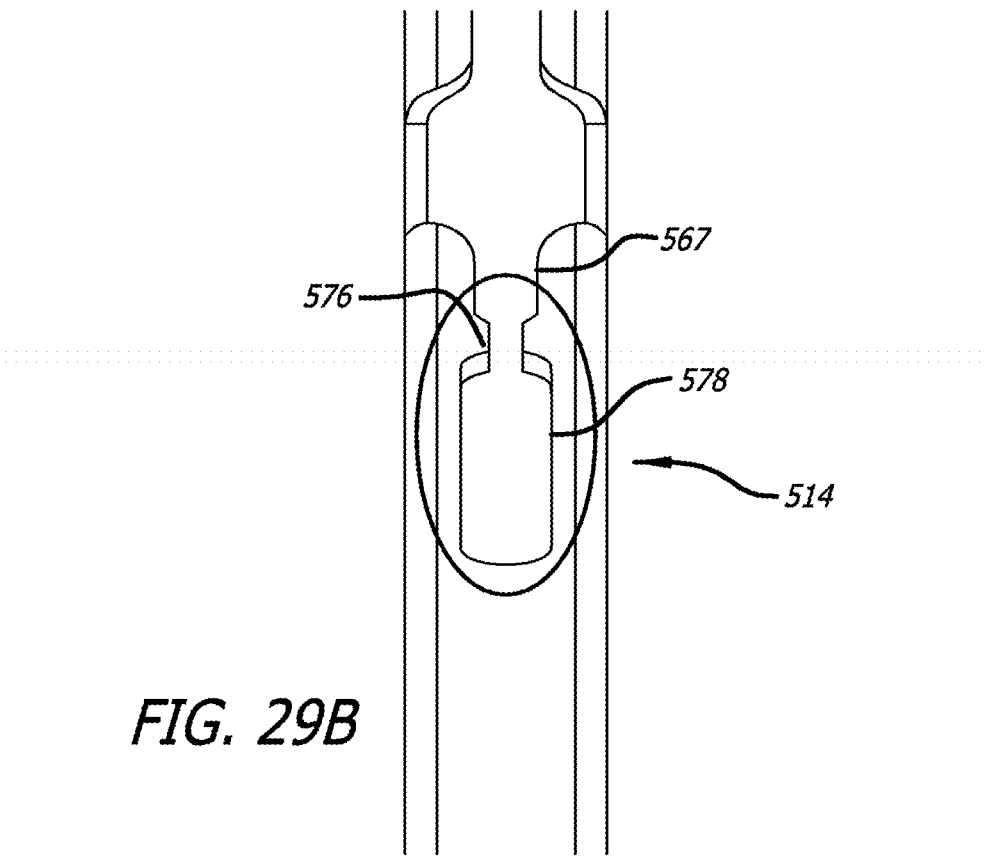
Figure 29C:
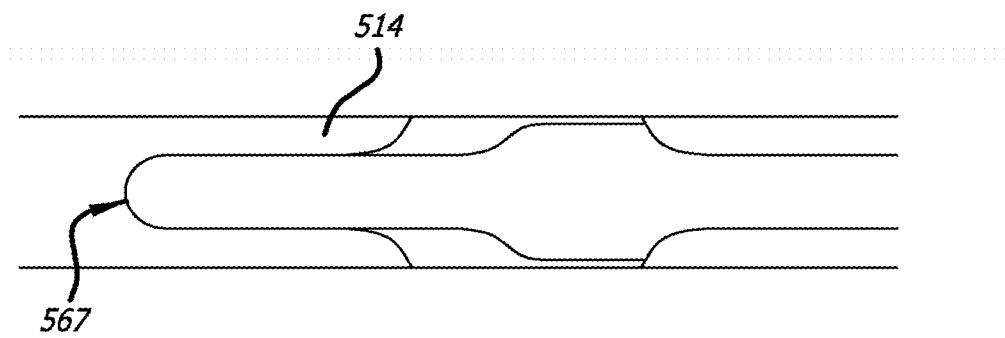

Turning to FIGS. 29A-C, there is shown a cutter 514 design incorporating additional structure for aiding in needle targeting. A reflective edge 576 can be added to a pill-shaped window 578 formed in the cutter 514 (See FIG. 29A). The edge 576 lies in line of site with the scope tube 506 to the needle penetration location. Operators can use this to target the needle by moving the tool anatomically proximal of the desired targeting location until the target is visible in the window 578. At that point, the operator can slowly slide the tool distally until the target just disappears below the reflective edge 576. The window 578 also provides direct visualization of more tissue adjacent the cutter. As shown in FIG. 29B, the window 578 can be extended to the suture guiding slot 567. A break in the reflection surface 576 creates an area which can be used for targeting by lining the target within the spaced reflective surfaces. Further, as shown in FIG. 29C, the suture centering slot 567 could be extended to allow direct visualization of a distal edge of the needle edge furthest from the scope. Here, beveled edges of the slot can provide useful reflective surfaces.

Figure 30A:
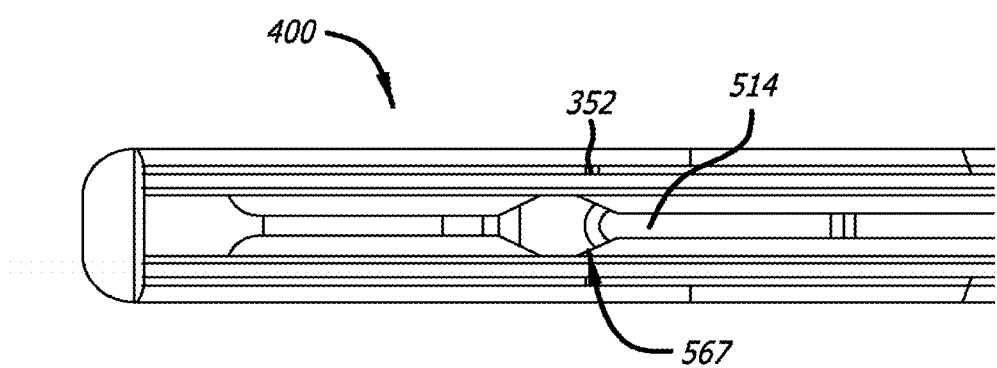
FIGS. 30A-C are top views, depicting structure for suture guides.
Figure 30B:
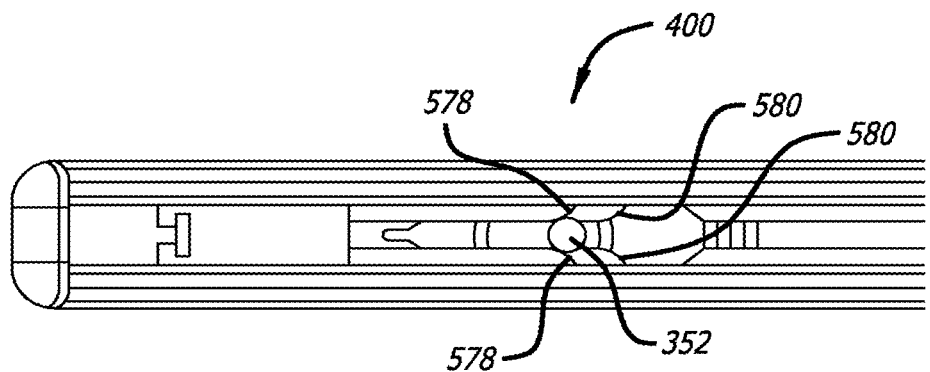
Figure 30C:
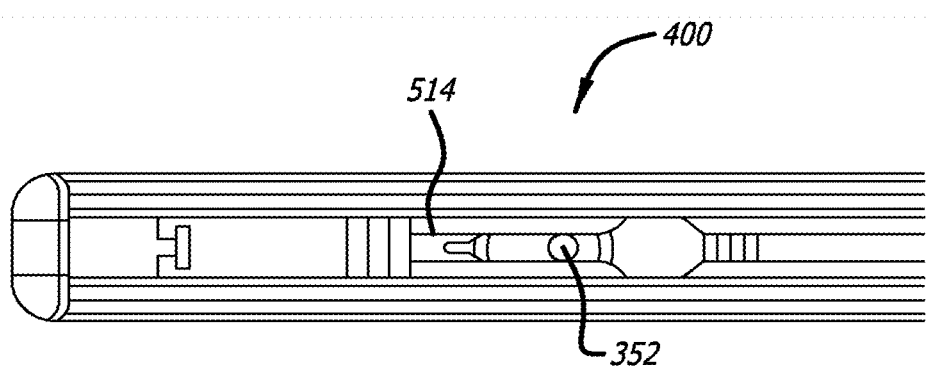

It is also contemplated that the delivery device can be configured so that the cutter 514 moves part-way and stop prior to engaging the connector and deployment of a proximal anchor (See FIGS. 30A-C). Top portions 578 of the cutter 514 can be configured to guide the suture or connector 352 to a position which ensures capture by the proximal anchor upon deployment (See FIG. 30B). Lead-in structure 580 can further be provided to guide the connector to center and tool proximal. Alternatively, the cutter 514 could also be positioned such that the proximal anchor motion would allow the connector 352 to cut on path and release the anchor assembly (FIG. 30C). It is further contemplated that flexible guide features (not shown) could additionally be added to a surface of the cutter, such features moving out of the way of the needle on needle deployment and then flexing back to contain the connector laterally and perhaps into a proximal portion.

Figure 31A:
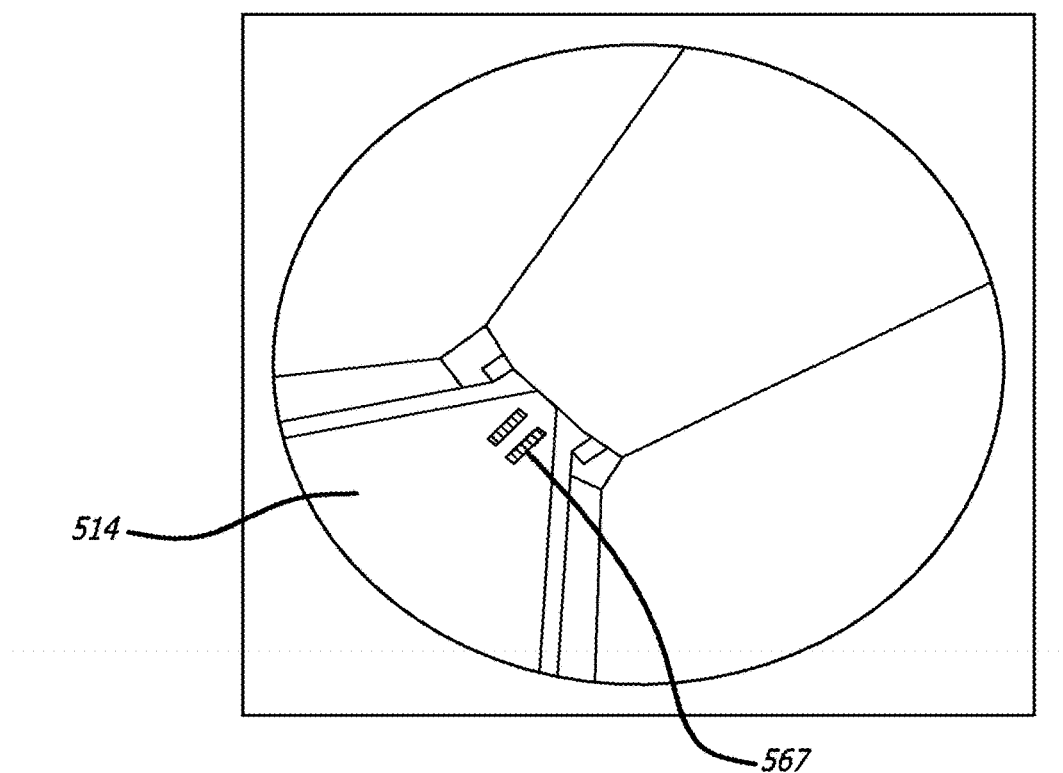
FIGS. 31A-D are enlarged views, depicting further approaches to target indicators.
Figure 31B:
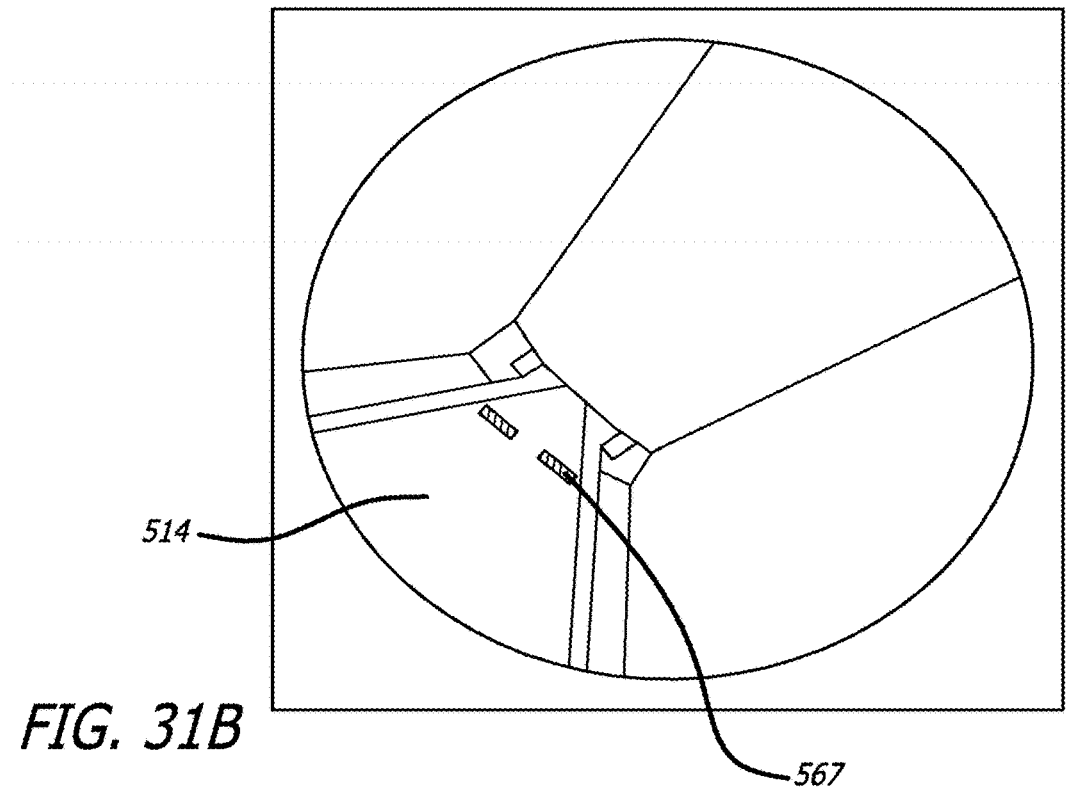
Figure 31C:
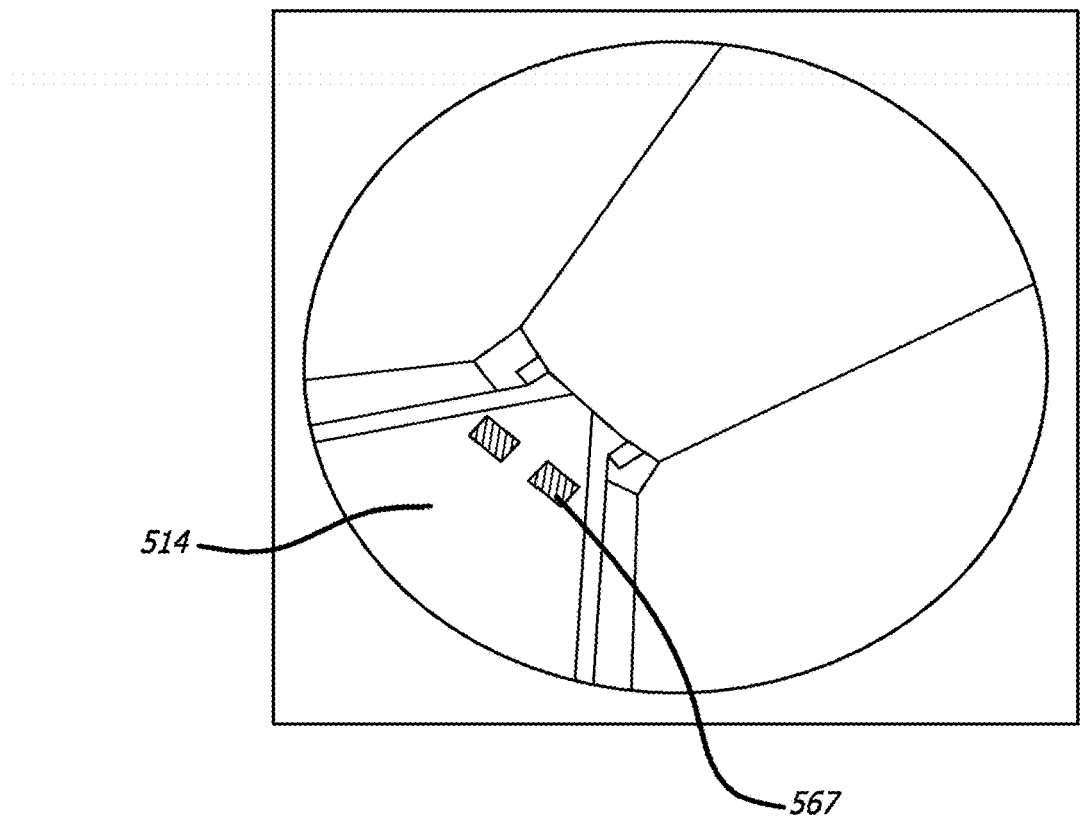
Figure 31D:
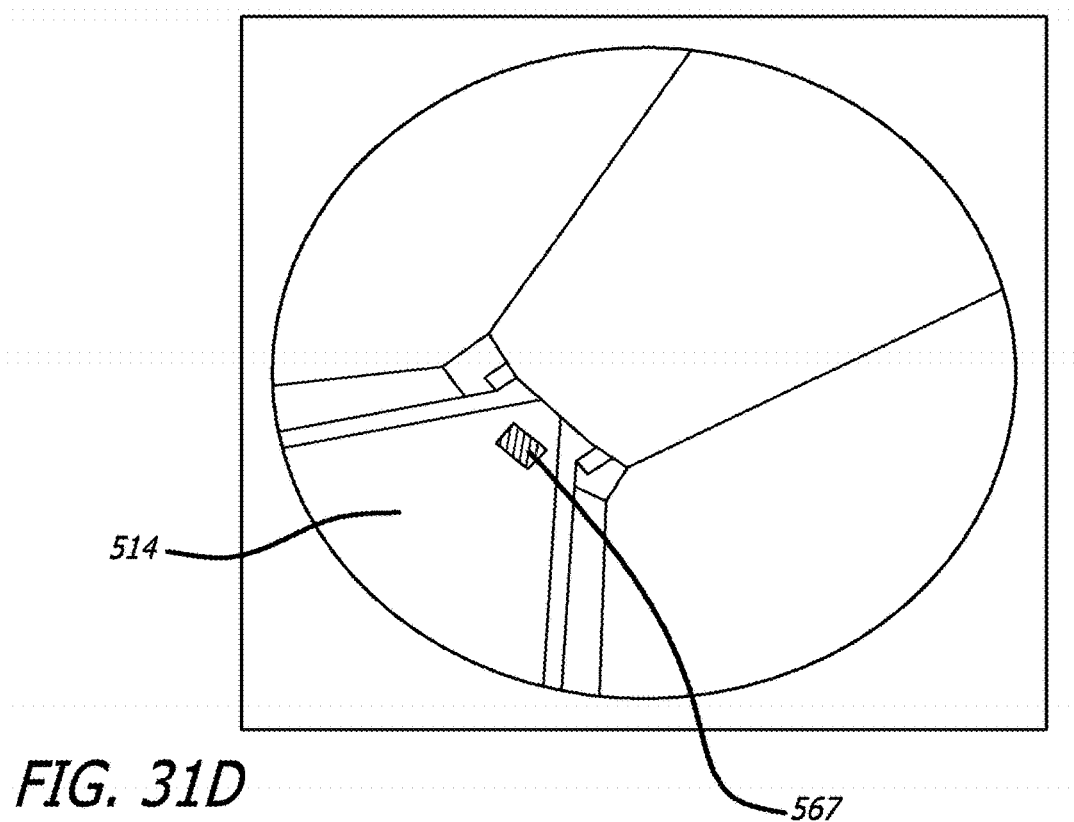

As shown in FIGS. 31A-D, the keyhole 567 formed in a cutter can have other various different reflective surfaces. There can be vertical polished edges (FIG. 31A), edged horizontal lines (FIG. 31B), polished rectangular areas (FIG. 31C), or an arrow (FIG. 31D). Again, such features can provide indicators of a needle exit point without adding components to the delivery system.

Figure 32:
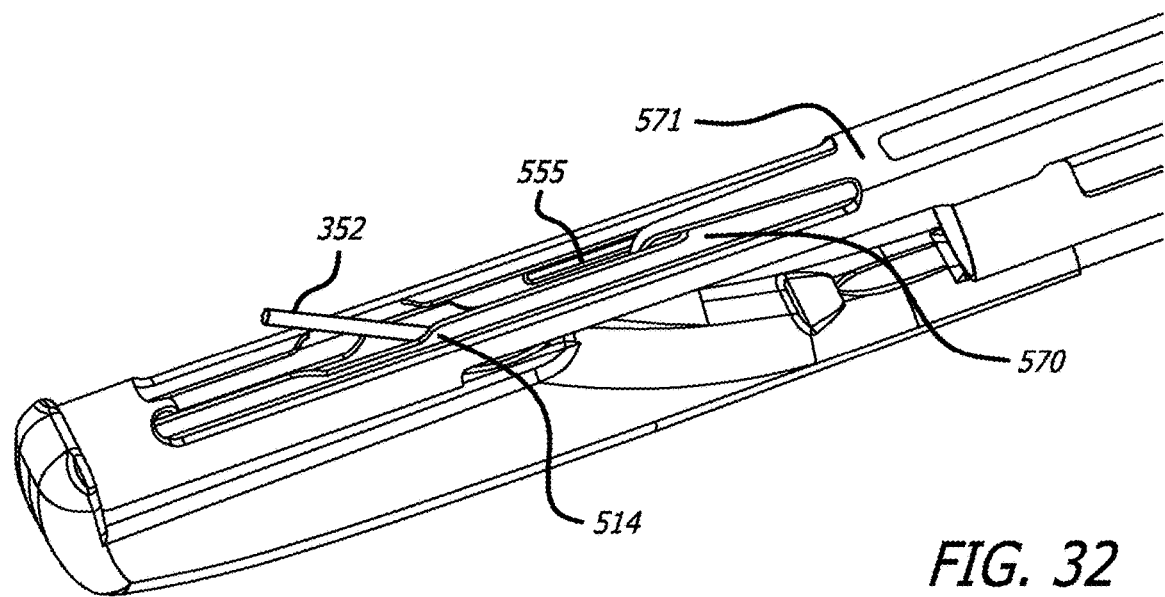
FIGS. 32-33 are perspective views, depicting features of a suture guide.
Figure 33:
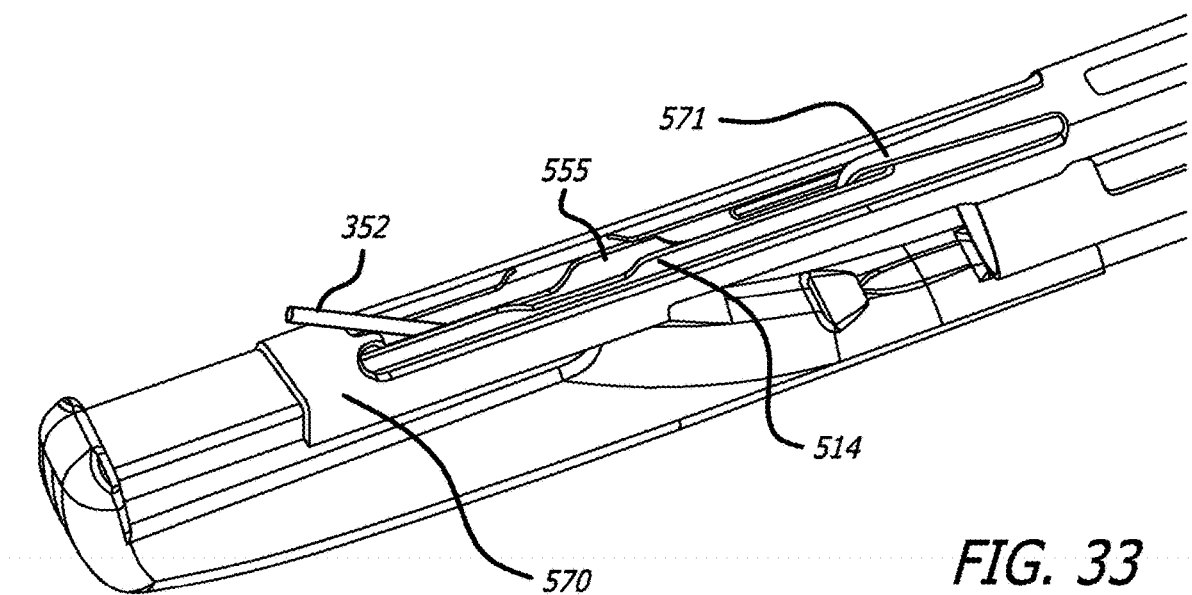

In a further aspect (FIGS. 32-33), the present device can include a suture alignment guide 570 configured to slide under a cover 571 and over the cutter 514. The cover 571, in turn, includes the finger projection 573 which is sized and shaped to control and guide the movement of a proximal anchor 555. The alignment slide 570 indexes the connector 352 to a centerline of the cutter 514. It also operates to pull the connector 352 proximally for indexing within the proximal anchor component 555 to thus enhance connector capture by the anchor component 555. In other embodiments, a distal end of the needle housing itself can alternatively or additionally include a slot or notch for properly registering or orienting the connectors during device use and particularly when tension is being applied to the connector.

Figure 34:
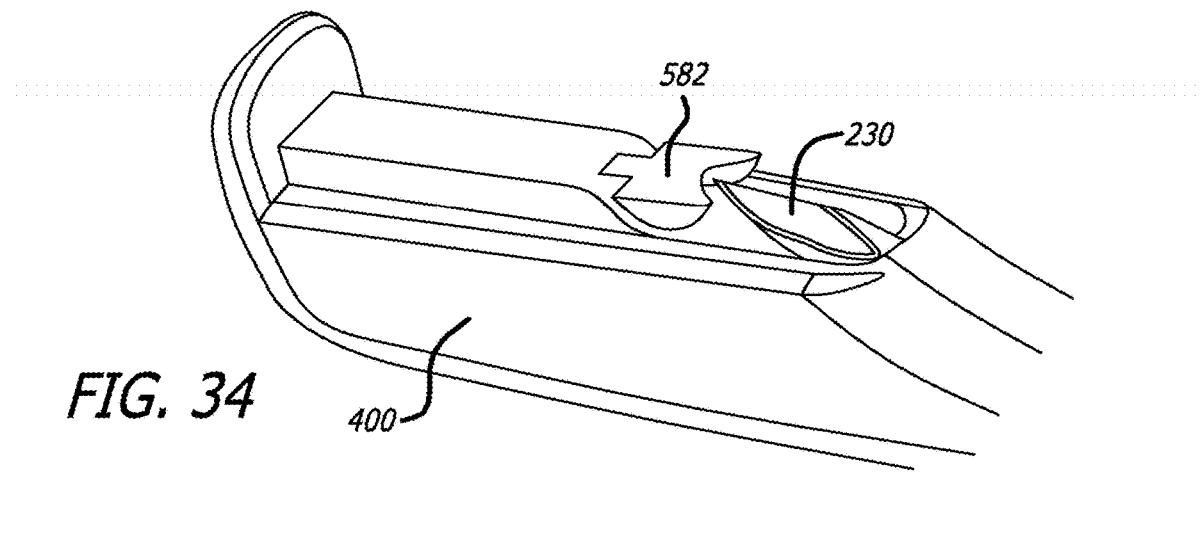
FIGS. 34-37 are various views, depicting guide structure for a suture.
Figure 35:
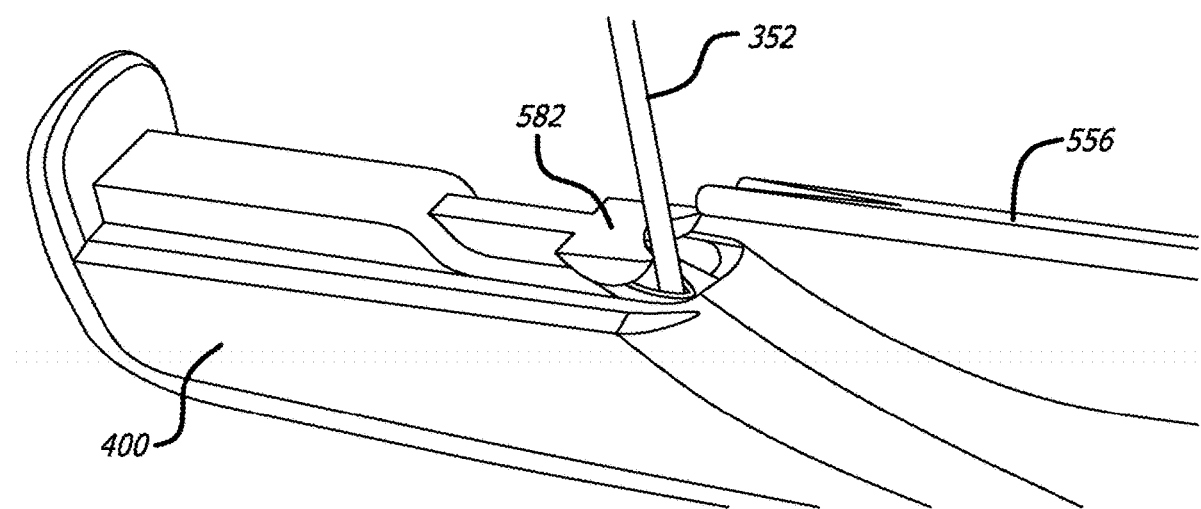
Figure 36:
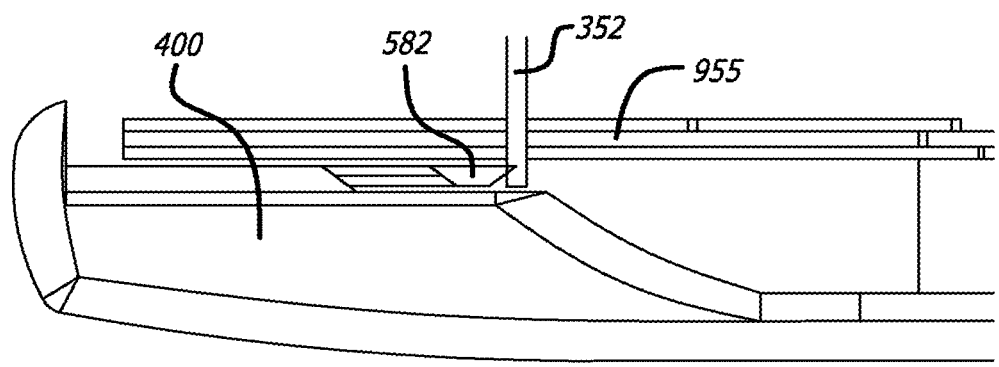
Figure 37:
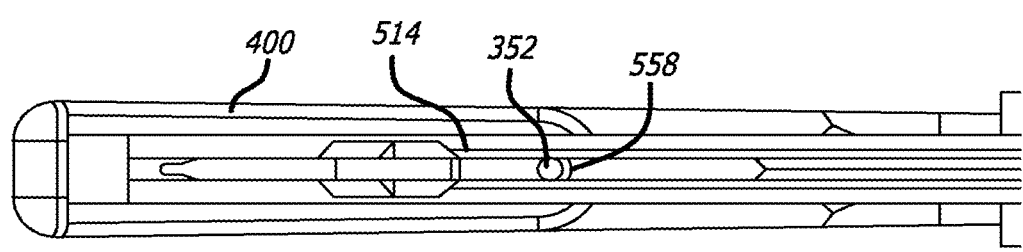

With reference to FIGS. 35-37, a suture indexing component 582 can be added to the leading end 400 of the delivery device. The suture indexing component can be spring loaded to assume distal (FIG. 34) and proximal (FIG. 35) positions. Further, as shown in FIG. 34, the indexing component 582 rests against the needle 230 prior to needle deployment. Once the needle is retracted to expose the connector 352, the indexing component 582 drives the connector 352 proximally and vertically into cutter keyhole structure (FIGS. 36-37). In this way, a desired connector orientation is presented to an anchor component 555.

Figure 38:
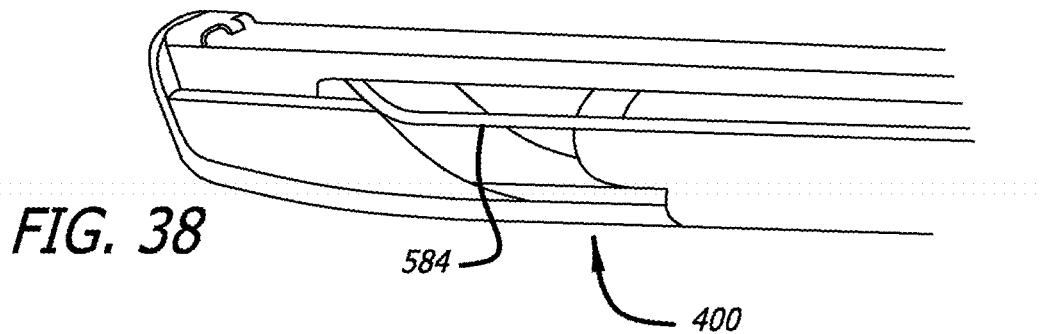
FIGS. 38-40 are various views, depicting another approach to a suture guide.
Figure 39:
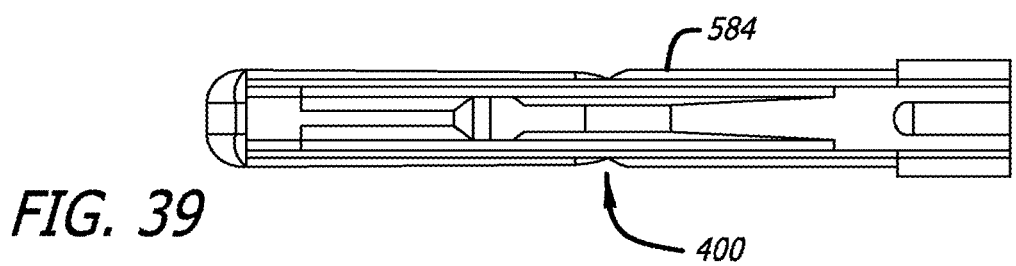
Figure 40:
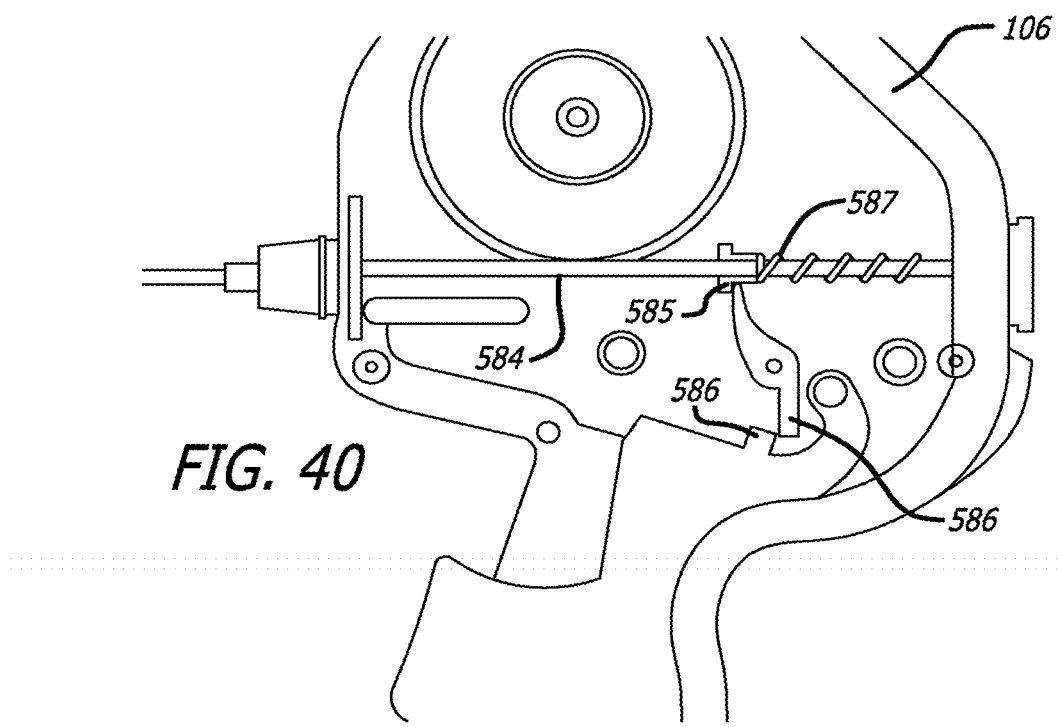
Figure 41:
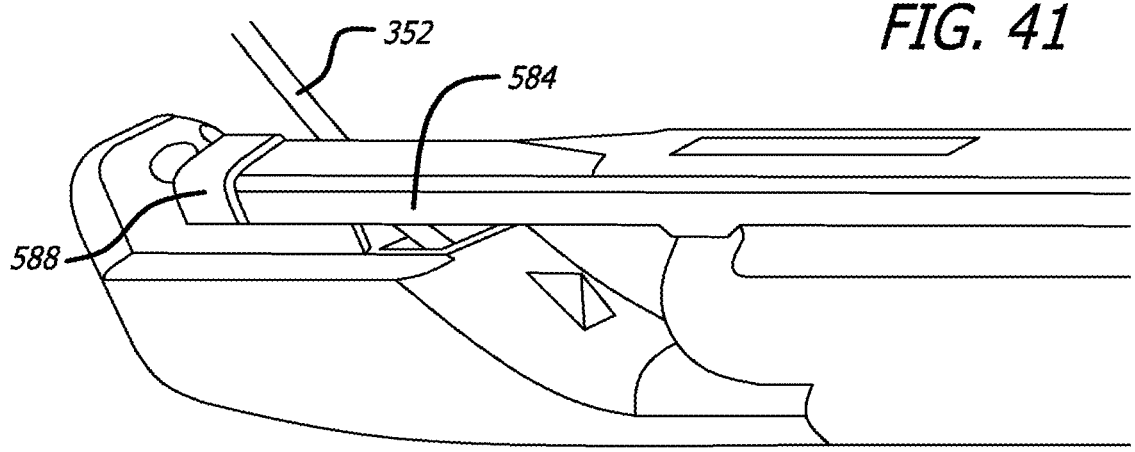
FIGS. 41-44 are various views, depicting further approaches to suture control.

Another approach to vertically orienting a connector is shown in FIGS. 38-40. Here, a flat wire element 584 can be routed from a delivery device case assembly 106 to the leading end 400 of the device. The wire element 584 is looped about a distal end of the connector exit and includes a proximal end portion connection to a block 585 of activating structures housed in the case assembly 106. Pawl and trip structure 586 are configured to interact with the block 585 to accomplish control of the wire element 584, each of which can be made to be responsive to handle lever activation. The block 585 in turn can be biased by a spring 587 to effect necessary control. Thus, when activated, the wire element 584 is positioned to effect the angle to which the connector exiting the delivery device is placed. In an alternative approach, the wire element 584 can be further equipped with a stamped element 588 configured to slide into contact with a connector 352. The stamped element 588 can be slid distally just prior to ejection of the proximal anchor.

Figure 42:
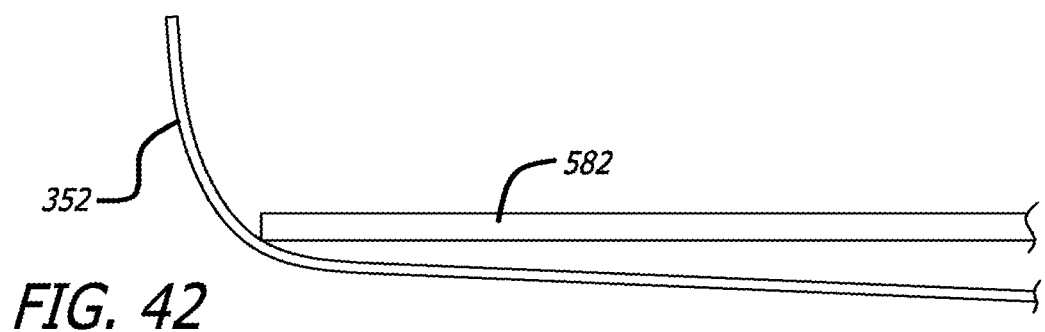
Figure 43:
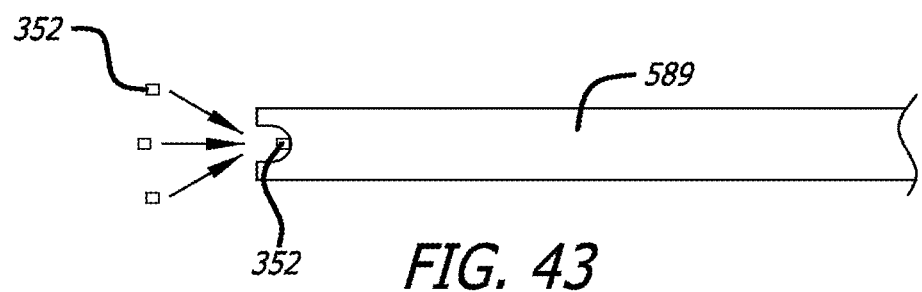
Figure 44:
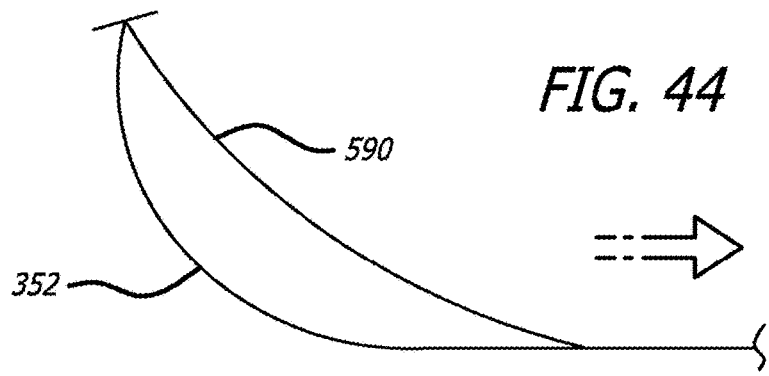

Another approach to suture angle control is shown in FIGS. 42 and 43. Rather than the wire element, a suture pusher 582 can be provided to engage and control the positioning of a connector 342. Moreover, a suture tensioner 590 can be included to provide tension to a connector 352 to thus orient the connector 352 as desired (See FIG. 44).

Figure 46:
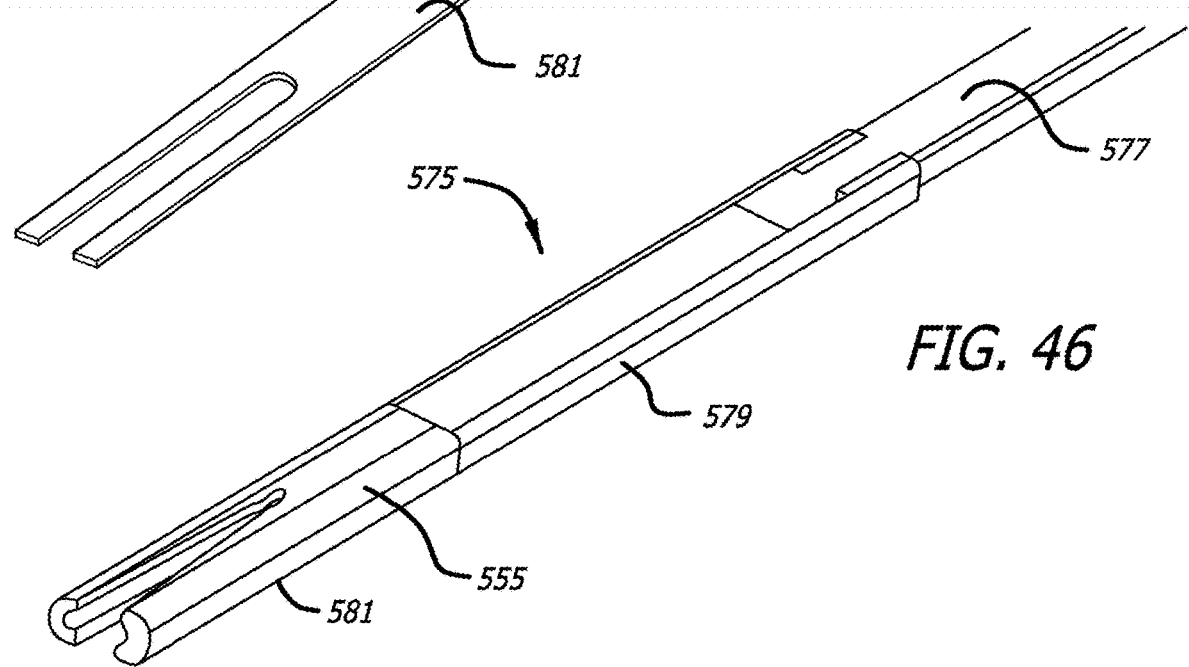
Figure 47:
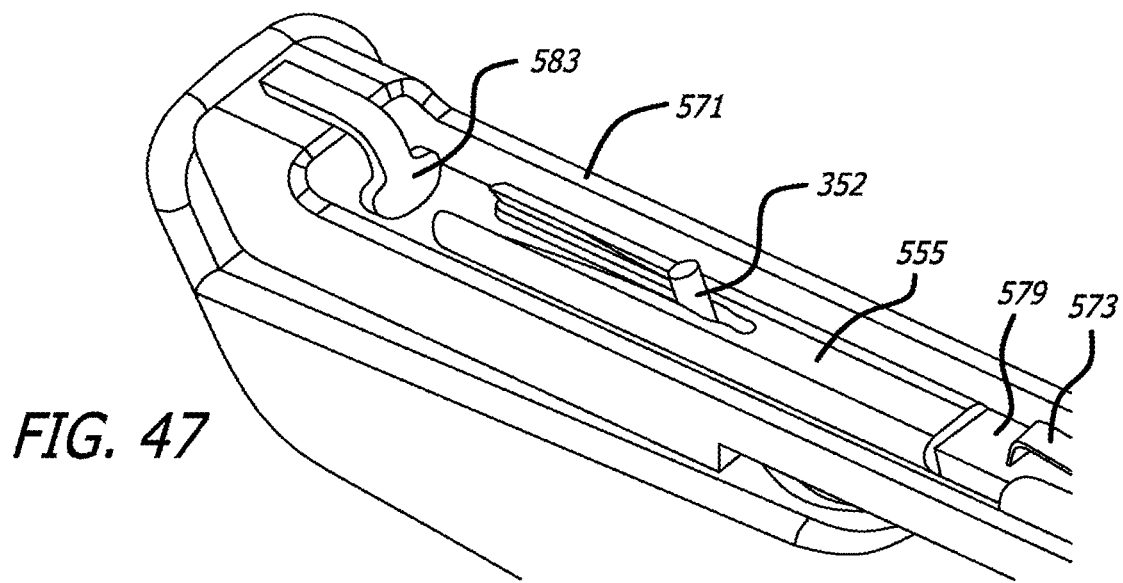

In order to accomplish the attachment of the proximal anchor 555 to the connector 352, a pusher assembly 575 is configured to extend within the cover 571 (See FIGS. 45-47). The pusher assembly 525 can include a proximal portion 577 which extends to the handle of the device (connected to pusher block as described below) and a distal portion 579 which attaches to the proximal portion 577. The distal portion 579 can further include an extension 581 sized to receive the length of a proximal anchor 555. The thickness of the extension 581 is chosen to ensure a 0.004 inch gap between a cutter and a bottom portion of the proximal anchor 555 so that a connector tag remains after its severing by the cutter. The cover 571 can further include an anchor stop 583 which is configured at a distal end of the cover 571. The anchor stop 583 is sized and shaped to protect the proximal anchor 555 from becoming trapped within the cover 571 after its engagement with the proximal anchor 555. Through its connection to the pusher of the pusher block 604, the pusher assembly 575 is advanced distally which, in turn, results in the proximal anchor component 555 engaging the connector 352 (See also FIG. 47). As the cutter block 565 moves proximally, the cutter 214 is withdrawn.

Figure 48:
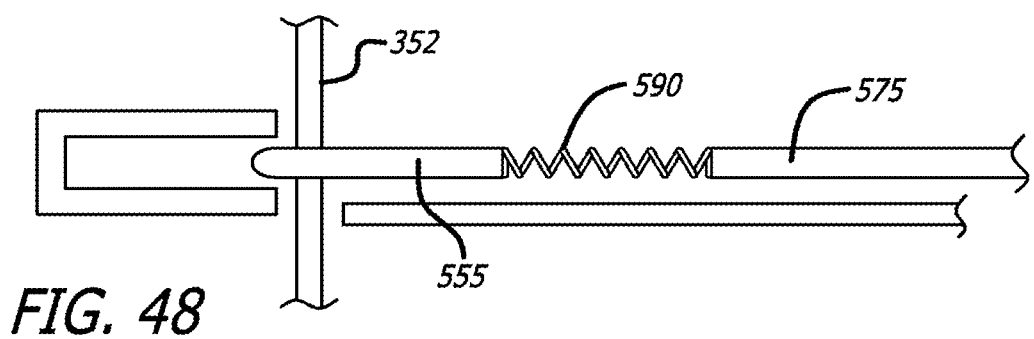
FIGS. 48-49 are side and top views, depicting structure facilitating anchor assembly.
Figure 49:
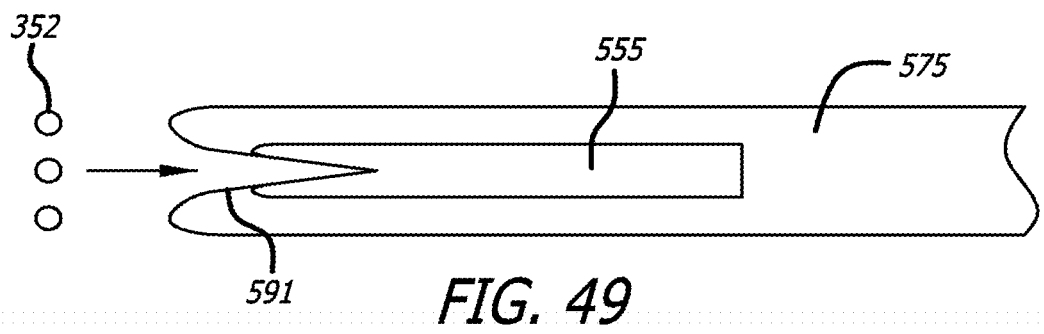

Alternative features of a pusher assembly 575 are shown in FIGS. 48 and 49. A distal portion of the pusher 575 can include a spring 590 (FIG. 48) for controlling the advancement of a proximal anchor 555 into engagement with a connector 352. Moreover, as shown in FIG. 49, the pusher 575 can be slotted to receive a proximal anchor 555 and can include a distal end with angled guide walls 591 configured to facilitate proper placement of the connector 352 within the anchor 355.

Figure 50:
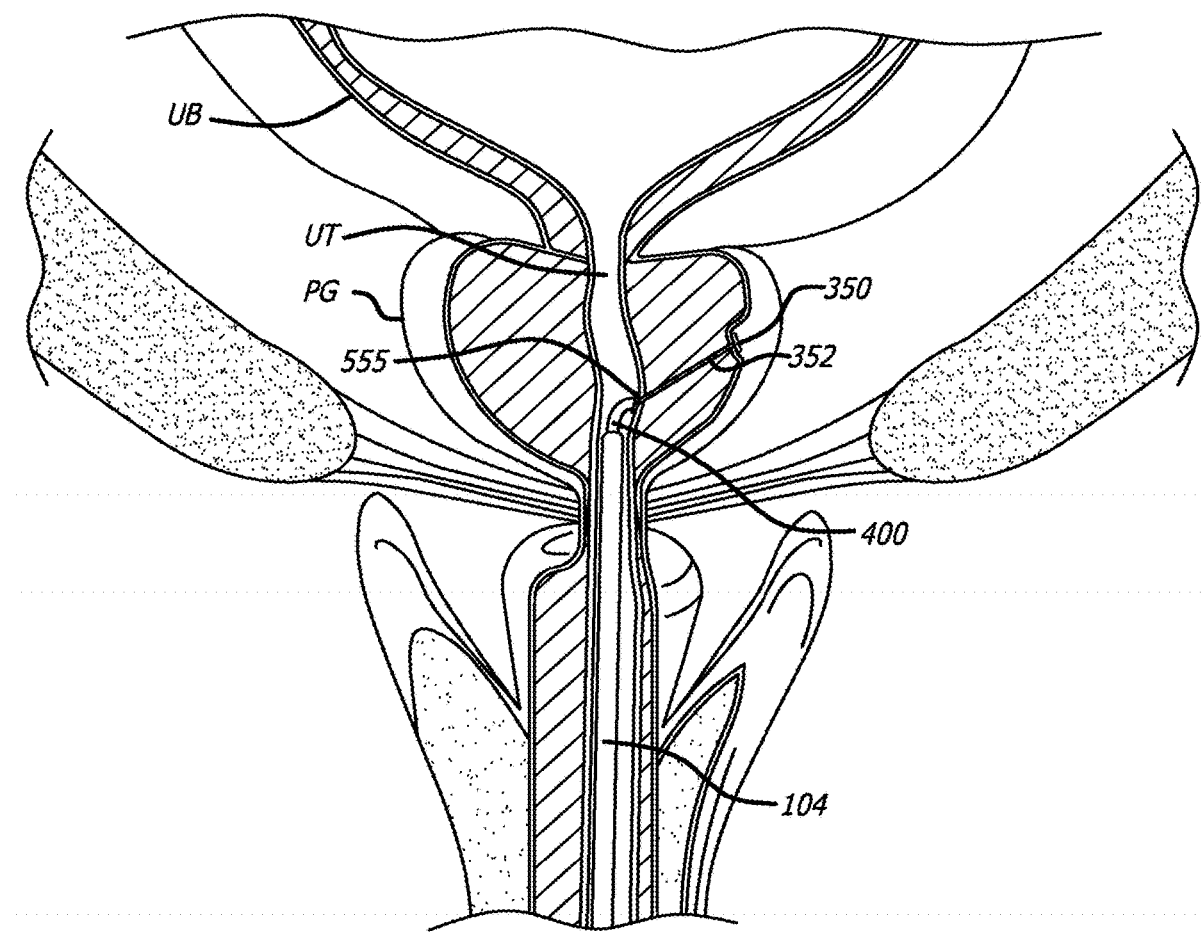
FIG. 50 is a cross-sectional view, depicting release of a second anchor component within an interventional site.

Release of the pusher assembly advances the second component 555 of an anchor assembly into locking engagement with a connector of an anchor assembly. Such action causes the pusher 575 to advance the anchor component 555 onto a connector (e.g., a suture) while the connector is being held by the tool with sufficient force and the anchor is advanced with sufficient speed and force to seat the anchor 555 with reliable retention force. Within a patient's body, as shown in FIG. 50, the anchor assembly is configured across anatomy within the interventional site. Upon withdrawal of the cutter assembly, the blade portion thereof is brought across the connector 352 thereby severing it close to the second anchor component 555 leaving a short tag.

Figure 51:
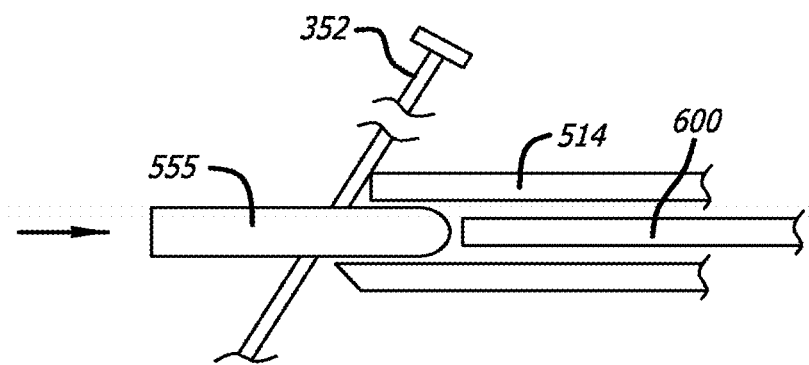
FIGS. 51-56 are cross-sectional views, depicting alternatives to approaches to structure for assembling an anchor.
Figure 52:
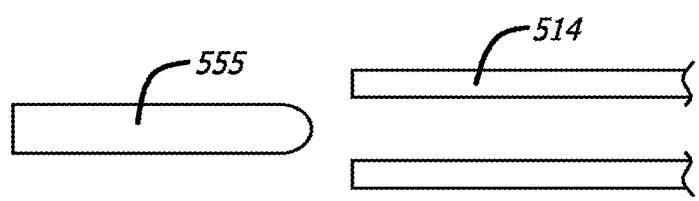

Various other approaches to control the engagement of a proximal anchor with a connector are shown in FIGS. 51-58. With reference to FIGS. 51 and 52, a back stop 600 can be configured within a stationary cutter 514 and the anchor 555 is advanced to first engage a connector 352 then present the connector 352 to the cutter 514 for severing. Here, the back stop is positioned, sized and shaped to control when the connector 352 is cut and to control the advancement of the anchor 555. The cutter 514 is then moved from engagement with the anchor 555, and the assembly is permitted to be ejected.

Figure 53:
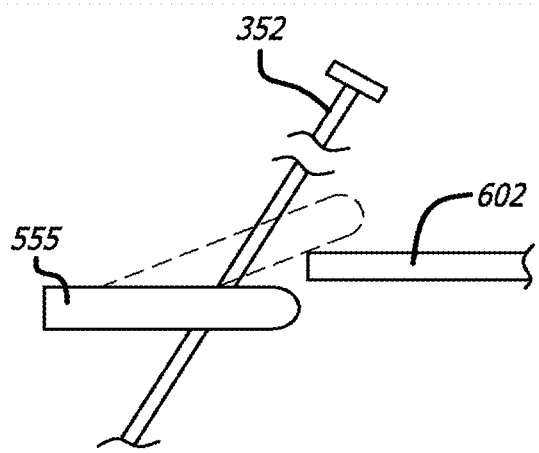
Figure 54:
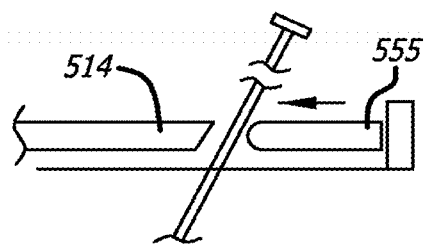
Figure 55:
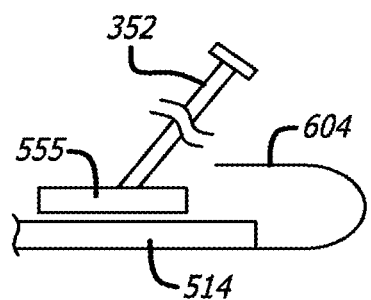
Figure 56:
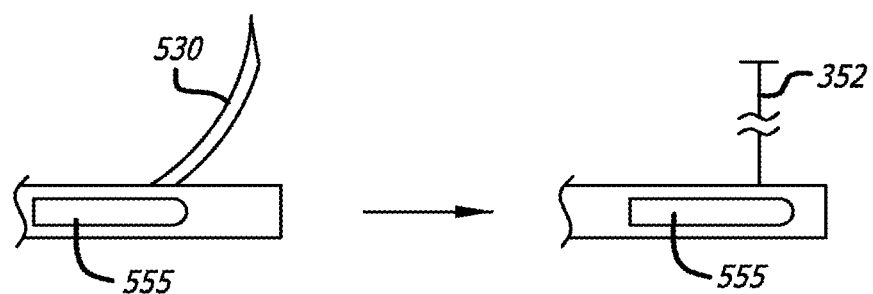
Figure 57:
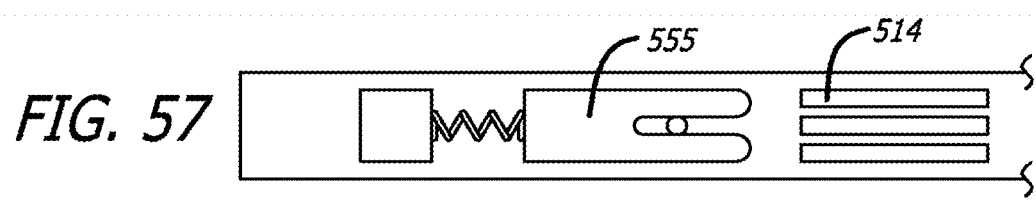
FIG. 57 is a cross-sectional view, depicting an alternative approach to structure for anchor assembly.
Figure 58:
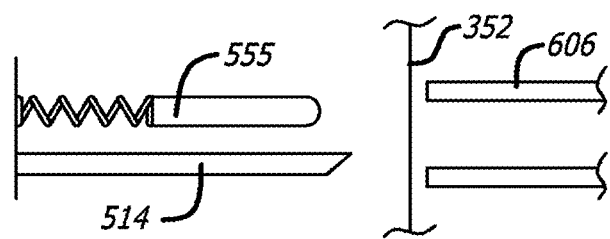
FIG. 58 is a cross-sectional view, depicting yet another alternative approach to structure for anchor assembly.

As shown in FIG. 53, a temporary constraint 602 can be configured within an end portion of a delivery catheter to keep a proximal anchor 352 within the window of capture. The constraint 602 can further facilitate launching the anchor 555 outward and into a robust engagement with the connector 352. In another approach (FIG. 54), there can be provided a stationary cutter 514 against which an anchor 558 and connector 352 can be proximally drawn to cut the connector 352. A cutter tail 604 (See FIG. 55) can be additionally provided on a cutter 514 to provide a useful backstop for a connector, as well as an advancing tip arrangement 606 depicted In FIG. 56. Moreover, a cutting element can be presented in an opposing direction to a spring biased anchor 555 as shown in FIG. 57 or alternatively, the cutter 514 and a spring biased anchor 555 can be configured to engage a connector 352 advanced by a tubular pusher 606 as shown in FIG. 58.

Figure 59:
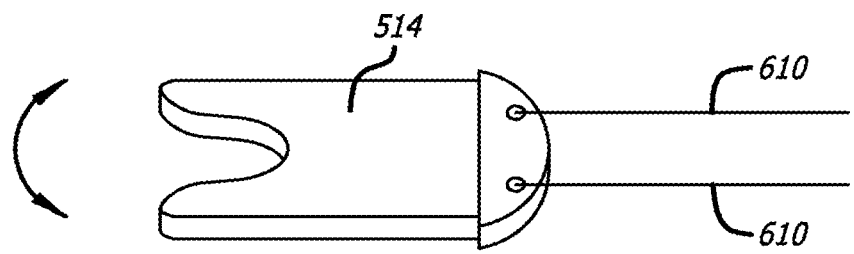
FIG. 59 is a perspective view, depicting an alternative approach to a cutter assembly.

Furthermore, as shown in FIG. 59, it is contemplated that a cutter 514 can be configured to articulate or otherwise rotate to accomplish a cutting function. In one approach, a pair of wires 610 can be mounted to a proximal side of the cutter to controllably rotate the cutter 514 against a connector. Such an approach would eliminate the need for moving parts longitudinally (cutter, anchor) to achieve anchor assembly.

Figure 67:
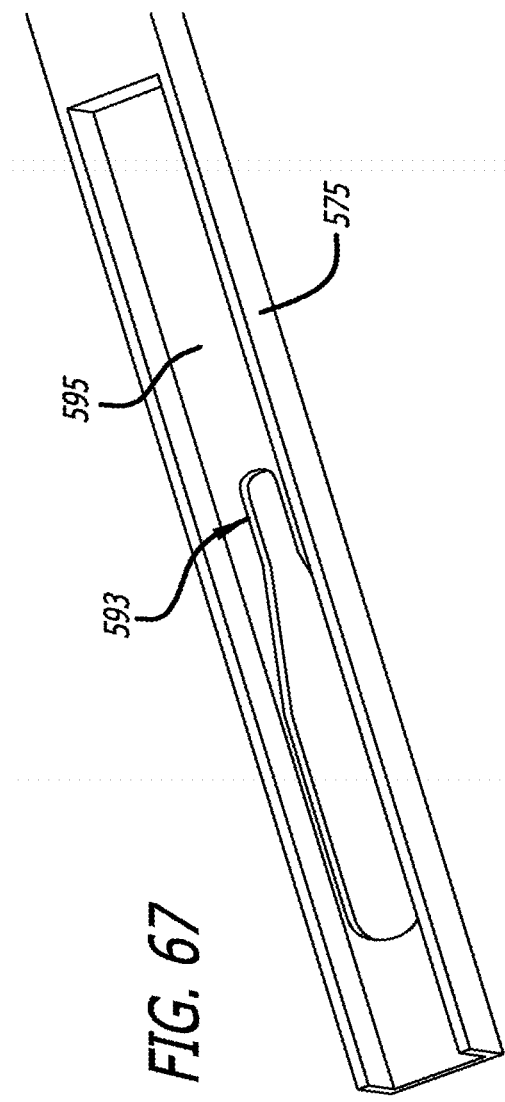
FIG. 67 is a perspective view, depicting one approach to a pusher.
Figure 68:
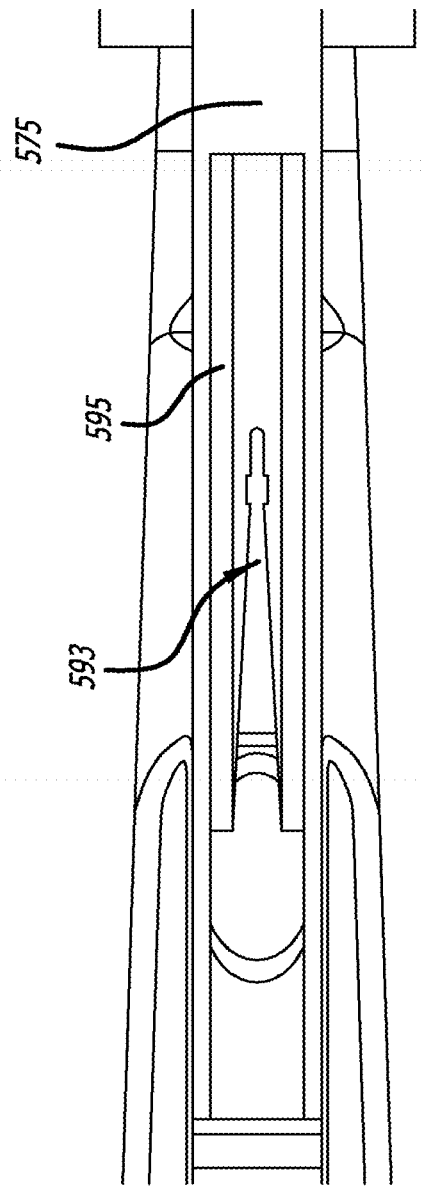
FIG. 68 is a top view, depicting the position of FIG. 67.
Figure 69:
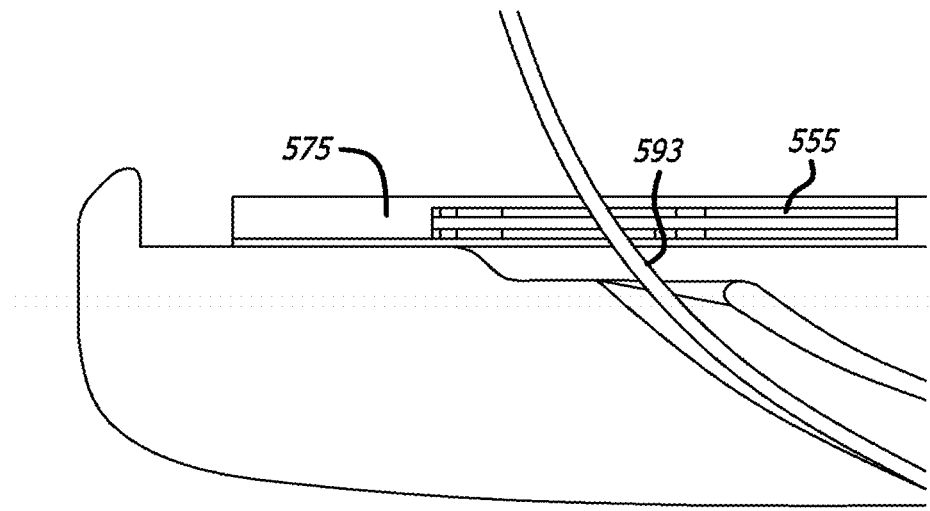
FIG. 69 is a side view, depicting the pusher of FIG. 67.
Figure 70A:
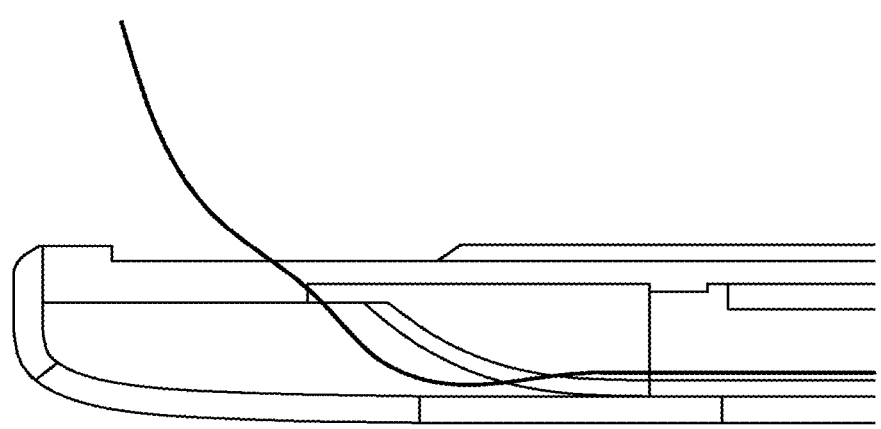
FIG. 70A is a side view, depicting a suture oriented at an oblique angle.
Figure 70B:
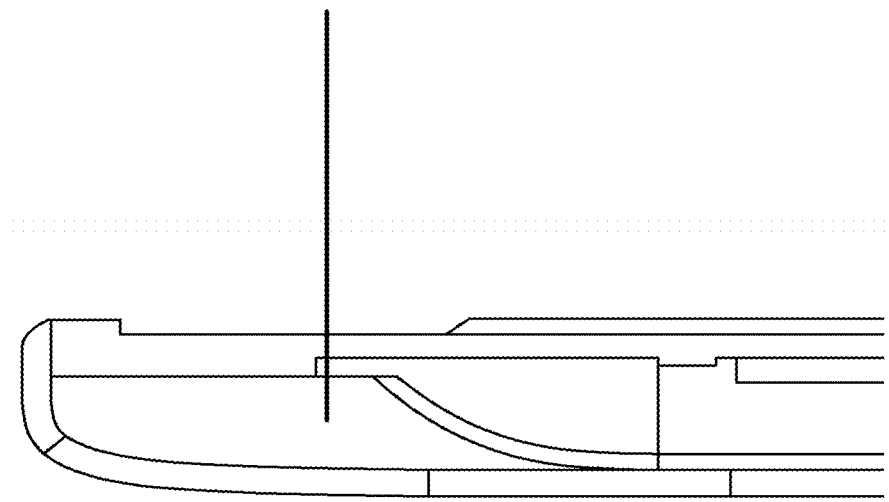
FIG. 70B is a side view, depicting a suture oriented at a perpendicular angle.
Figure 70C:
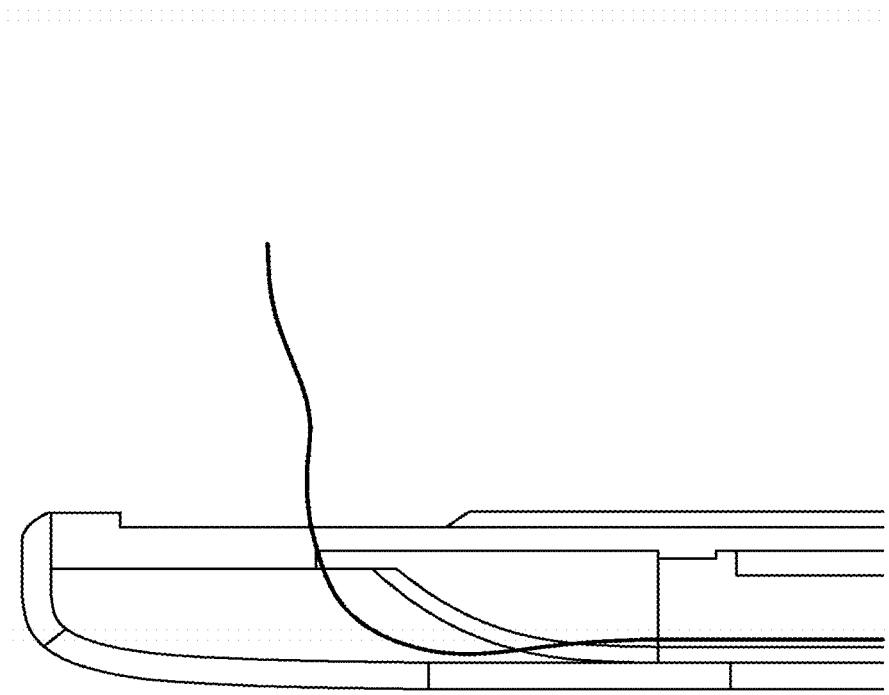
FIG. 70C is a side view, depicting a suture oriented at an outer angle.

Referring now to FIGS. 67, 68, and 69 in some embodiments a pusher 575 includes a proximal slot edge 593 that contacts the suture prior to the suture (or other connector) contacting the proximal portion of the slot in proximal anchor 555. The pusher 575 includes a tray feature 595 in which proximal anchor 555 is carried while proximal anchor 555 is being pushed to engage the suture. The proximal slot edge 593 extends further distally than the section of the proximal anchor 555 that ultimately connects to the suture. FIG. 70A depicts a situation where the suture is oriented at an oblique angle to the push direction of the proximal anchor 555. When proximal slot edge 593 contacts the suture prior to the proximal anchor 555 being firmly connected to the suture, the suture can be oriented at a more orthogonal angle (FIG. 70B) or acute angle (70C). In such orthogonal or acute orientations, the suture is more likely to firmly engage the proximal anchor 555.

Figure 60:
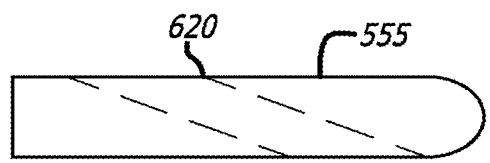
FIGS. 60-61 are side and top views, depicting alternative approaches to anchor structure.
Figure 61:
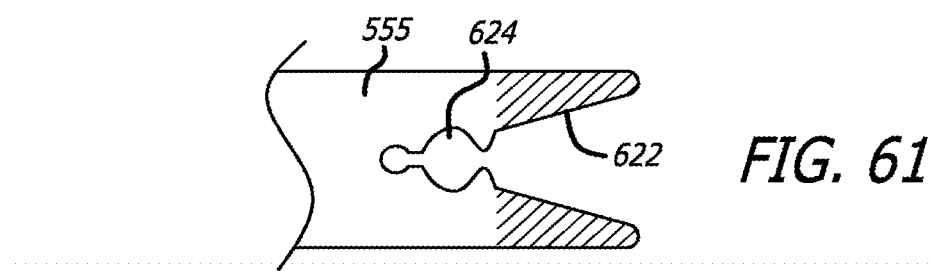

Also, variations to structures of a proximal anchor are also contemplated. For example, surfaces of anchor structure presented for locking engagement with a connector can be angled (non-perpendicular) 620 (FIG. 60) to accommodate connector orientation and to provide for secure engagement. Knurled surfaces 622 are also contemplated for facilitating desired engagement of parts, as is the location of the connector capture area 624 of an anchor 555. Finally, it is further contemplated that arms of an anchor can be held open for receiving a connector and permitted to close about the connector to provide a robust lock between parts.

Figure 62:
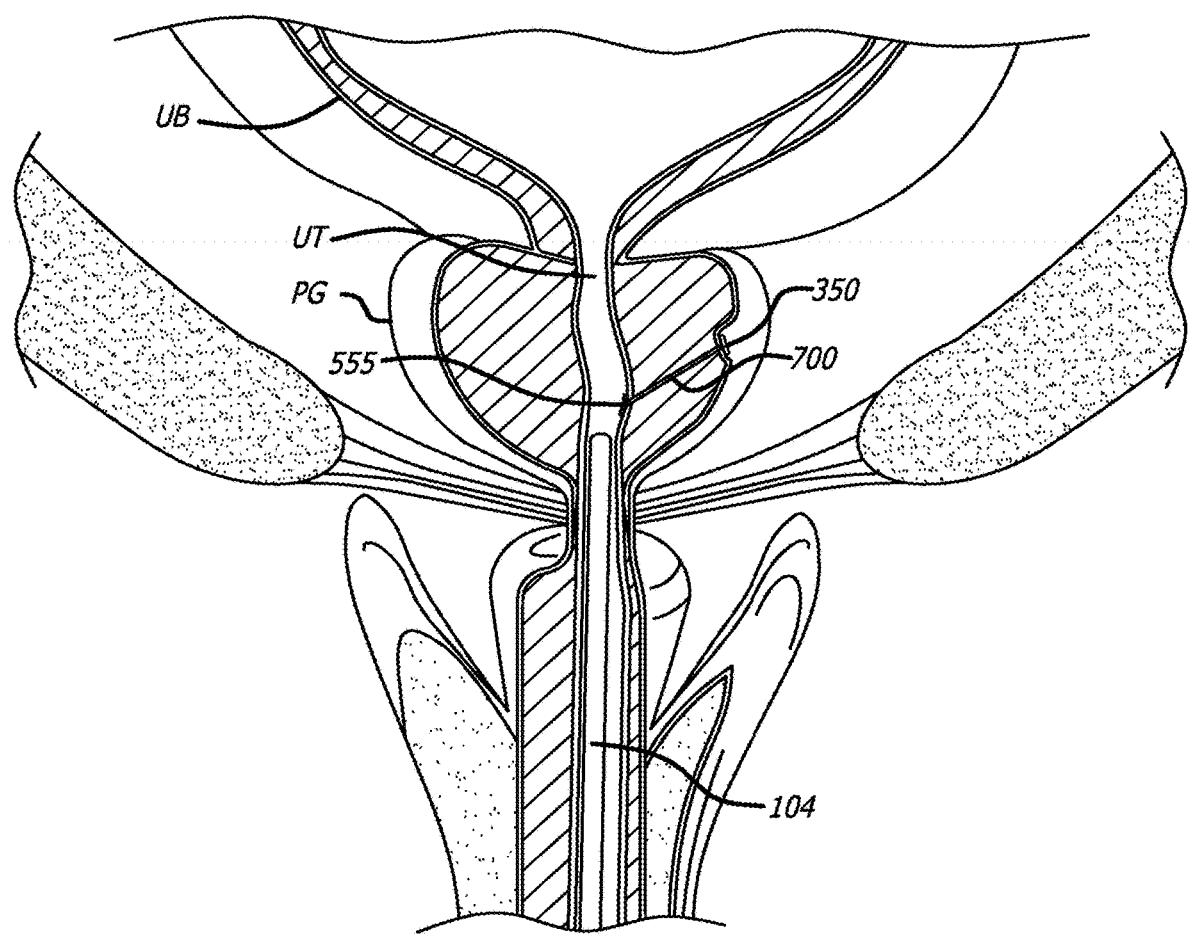
FIG. 62 is a cross-sectional view, depicting release of an assembled anchor assembly within an interventional site.
Figure 63:
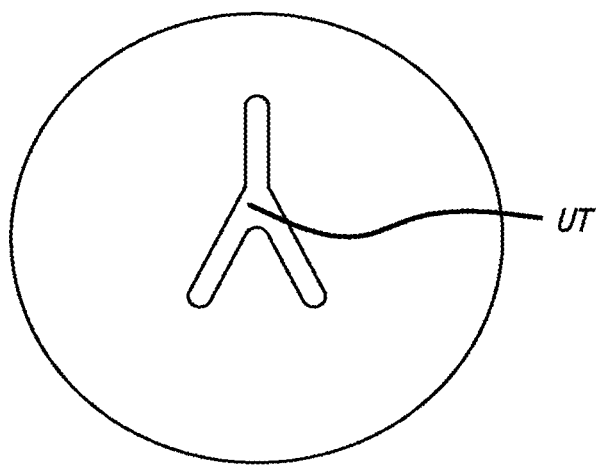
FIG. 63 is a cross-sectional view looking along the axis of the urethra within an enlarged prostate, depicting an untreated interventional site.
Figure 64:
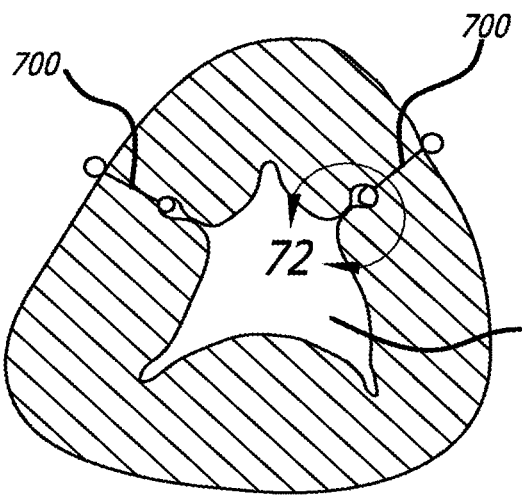
FIG. 64 is a cross-sectional view looking along the axis of the urethra within an enlarged prostate, depicting implantation of two anchor assemblies at an interventional site.
Figure 66:
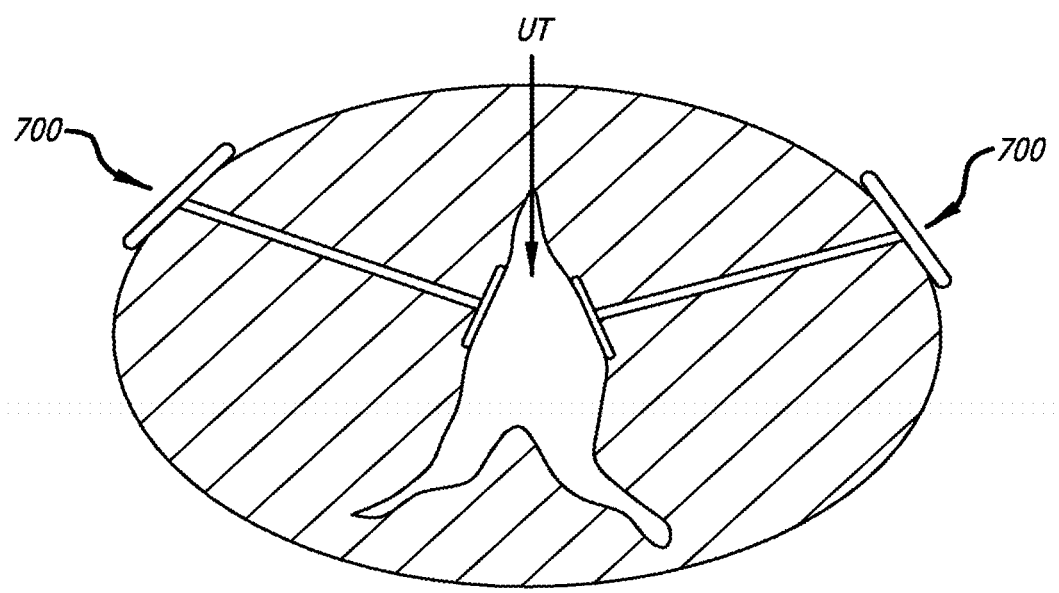
FIG. 66 is a cross-sectional view, depicting another view of two anchor assemblies implanted at an interventional site.

An implanted anchor assembly 700 is shown in FIGS. 62, 64 and 66. FIG. 64 depicts a partial cross-sectional view of the urethra (UT) widened due to the anchor assembly compressing the surrounding enlarged prostate tissue due to the fact that the outer capsular tissue is rather strong, substantially non-compressible and non-displaceable while the adenoma of the prostate gland is compressible and the urethral wall displaceable.

The second anchor component can be embodied in a slotted anchor configured to secure to a connector. The slotted proximal anchor can include a flattened-tubular back end that resembles a flattened tube in shape, with a width in lateral cross-section that is greater than its thickness. The slotted proximal anchor also includes a pair of spaced apart prongs extending from the back end of the slotted proximal anchor to the front end of the slotted proximal anchor. The spaced prongs join together at a slot inception. The prongs are shaped and sized of a configuration and of a rigidity to substantially prevent deflection of the prongs. The prongs can include inwardly facing protrusions that are configured to capture and deform the connector between the protrusions and prevent the connector from disengaging from the slotted anchor device once engaged. The mechanism of suture attachment and strength of the assembly is a combination of compression of the suture between the stiff slotted prongs of the anchor as well as disruption of the suture surface by the discreet edges of the slotted, flattened-tubular anchor. The discreet edges provide a lower contact surface area between anchor prongs and suture and focuses the compressive forces in focal points that cause the suture to conform around both internal recesses and external faces. It is also to be recognized that various further embodiments of slotted anchors or anchors forming a clip are also contemplated. In particular, various embodiments of structures which accordingly provide alternative approaches to attach to a connector can be employed. That is, the anchors can be deformable, deflectable, latching, nested, meltable and/or coiled in structure.

Accordingly, the present disclosure contemplates both pushing directly on anchor portions of an anchor assembly as well as pushing directly upon the connector of the anchor assembly. Moreover, as presented above, the distal or first anchor component is advanced and deployed through a needle assembly and at least one component of the proximal or second anchor component is advanced and deployed from a housing portion of the anchor deployment device. Further, either a single anchor assembly or multiple anchor assemblies can be delivered and deployed at an intervention site by the deployment device. Additionally, a single anchor assembly component can for example, be placed on one side of a prostate or urethra while multiple anchor assembly components can be positioned along an opposite or displaced position of such anatomy. The number and locations of the anchor assemblies can thus be equal and/or symmetrical, different in number and asymmetrical, or simply asymmetrically placed. In the context of prostate treatment, the present disclosure is used for the compression of the prostate gland and the opening of the prostatic urethra, the delivering of an implant at the interventional site, and applying tension between ends of the implant. Moreover, drug delivery is both contemplated and described as a further remedy in BPH and over active bladder treatment as well as treating prostate cancer and prostatitis.

Figure 65:
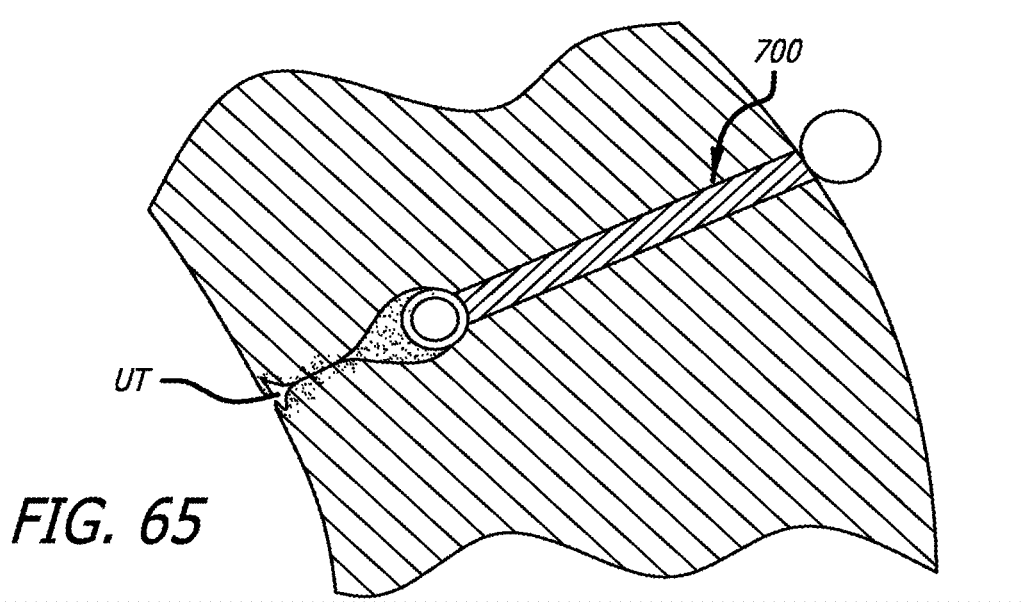
FIG. 65 is an enlarged view of a portion of FIG. 64.

Once implanted, the anchor assembly of the present disclosure accomplishes desired tissue manipulation, approximation, compression or retraction as well as cooperates with the target anatomy to provide an atraumatic support structure. In one preferred embodiment, the shape and contour of the anchor assembly 700 is configured so that the assembly invaginates within target tissue, such as within natural folds formed in the urethra by the opening of the urethra lumen by the anchor assembly (See FIGS. 64-65). In fact, in situations where the anchor assembly is properly placed, wispy or pillowy tissue in the area collapses around the anchor structure. Eventually, the natural tissue can grow over the anchor assembly 700 and new cell growth occurs over time (see FIG. 62). Such cooperation with target tissue facilitates healing and avoids unwanted side effects such as calcification or infection at the interventional site.

Subsequent to the interventional procedure, the patient can be directed to take alpha blockers for 2-4 weeks. Anti-inflammatory medicine can also be taken.

Furthermore, in addition to an intention to cooperate with natural tissue anatomy, the present disclosure also contemplates approaches to accelerate healing or induce scarring. Manners in which healing can be promoted can include employing abrasive materials, textured connectors, biologics and drugs.

It has been observed that placing the anchors at various desired positions within anatomy can extract the best results. For example, when treating a prostate, one portion of an anchor assembly can be placed within an urethra and a second component beyond the outer surface of the prostate. It has been found that implanting the anchor assemblies by using the distal end of the device to displace the prostate lobe on either side (while the tension spring is taking up slack in the connector after the delivery needle has been refracted) while deploying the second anchor component so that the ten o'clock and two o'clock positions (when looking along the axis of the urethra) are supported or retained, effectively holds the anatomy open and also facilitates invagination of the anchor portion within natural tissue. Typically, one to two pairs of anchor assemblies are implanted to create an anterior channel along the urethra within the prostate gland. This is particularly true in the regions of anatomy near the bladder and the juncture at which the ejaculatory duct connects to the urethra.

Additionally, it is contemplated that the components of the anchor assembly or selected portions thereof (of any of the anchor assemblies described or contemplated), can be coated or embedded with therapeutic or diagnostic substances (e.g. drugs or therapeutic agents). Again, in the context of treating a prostate gland, the anchor assembly can be coated or imbedded with substances such as 5-alpha-reductase which cause the prostate to decrease in size. Other substances contemplated include but are not limited to phytochemicals generally, alpha-1a-adrenergic receptor blocking agents, smooth muscle relaxants, and agents that inhibit the conversion of testosterone to dihydrotestosterone. In one particular approach, the connector 95 can for example, be coated with a polymer matrix or gel coating which retains the therapeutic or diagnostic substance and facilitates accomplishing the timed release thereof. Additionally, it is contemplated that bacteriostatic coatings as well as analgesics and antibiotics for prostatitis and other chemical coatings for cancer treatment, can be applied to various portions of the anchor assemblies described herein. Such coatings can have various thicknesses or a specific thickness such that it along with the connector itself matches the profile of a cylindrical portion of an anchor member affixed to the connector. Moreover, the co-delivery of a therapeutic or diagnostic gel or other substances through the implant deployment device or another medical device (i.e. catheter), and moreover an anchor assembly including the same, is within the scope of the present disclosure as is radio-loading devices (such as a capsular or distal ends of implants for cancer or other treatment modalities). In one such approach, the deployment device includes a reservoir holding the gel substance and through which an anchor device can be advance to pick up a desired quantity of therapeutic or diagnostic gel substance.

It is to be recognized that the timing of the dual advancement of the needle and connector assemblies and subsequent relative motion between the assemblies is coordinated. That is, the needle assembly first provides access to an interventional site and then the connector assembly is left extending beyond a terminal end of the needle assembly through the relative motion of the needle and connector assemblies.

It is further contemplated that in certain embodiments, the anchor delivery device can include the ability to detect forces being applied thereby or other environmental conditions. Various sections of the device can include such devices and in one contemplated approach sensors can be placed along the needle assembly. In this way, an operator can detect for example, whether the needle has breached the target anatomical structure at the interventional site and the extent to which such breaching has occurred. Other sensors which can detect particular environmental features can also be employed such as blood or other chemical or constituent sensors. Moreover, one or more pressure sensors or sensors providing feedback on the state of deployment of the anchor assembly during delivery or after implantation are contemplated. For example, tension or depth feedback can be monitored by these sensors. Further, such sensors can be incorporated into the anchor assembly itself, other structure of the deployment device or in the anatomy.

Moreover, it is to be recognized that the foregoing procedure is reversible. In one approach, the connection of an anchor assembly can be severed and a proximal (or second) anchor component removed from the patient's body. For example, the physician can cut the connector and simultaneously remove the second anchor previously implanted for example, in the patient's urethra using electrosurgical, surgical or laser surgical devices used in performing transurethral prostate resection.

An aspect that the various embodiments of the present disclosure provide is the ability to deliver an anchor assembly having a customizable length, each anchor assembly being implanted at a different location without having to remove the device from the patient. Other aspects of the various embodiments of the present disclosure are load-based delivery, of an anchor assembly, anchor assembly delivery with a device having integrated connector, (e.g. suture), cutting, and anchor assembly delivery with an endoscope in the device. The delivery device is uniquely configured to hold the suture with tension during delivery to help ensure that the first anchor component sits firmly against a tissue plane (e.g., the outer capsule of the prostate) and is held relatively firm as the second anchor component is attached to the connector and the delivery device. In this aspect, the needle assembly acting as a penetrating member is cooperatively connected to a mechanism, which pulls on the anchor while the needle assembly is retracted.

It is to be recognized that various materials are within the scope of the present disclosure for manufacturing the disclosed devices. Moreover, one or more components such as distal anchor, proximal anchor, and connector, of the one or more anchor devices disclosed herein can be completely or partially biodegradable or biofragmentable.

Further, as stated, the devices and methods disclosed herein can be used to treat a variety of pathologies in a variety of lumens or organs comprising a cavity or a wall. Examples of such lumens or organs include, but are not limited to urethra, bowel, stomach, esophagus, trachea, bronchii, bronchial passageways, veins (e.g. for treating varicose veins or valvular insufficiency), arteries, lymphatic vessels, ureters, bladder, cardiac atria or ventricles, uterus, fallopian tubes, etc.

Finally, it is to be appreciated that the disclosure has been described hereabove with reference to certain examples or embodiments of the disclosure but that various additions, deletions, alterations and modifications may be made to those examples and embodiments without departing from the intended spirit and scope of the disclosure. For example, any element or attribute of one embodiment or example may be incorporated into or used with another embodiment or example, unless to do so would render the embodiment or example unpatentable or unsuitable for its intended use. Also, for example, where the steps of a method are described or listed in a particular order, the order of such steps may be changed unless to do so would render the method unpatentable or unsuitable for its intended use. All reasonable additions, deletions, modifications and alterations are to be considered equivalents of the described examples and embodiments and are to be included within the scope of the following claims.

Thus, it will be apparent from the foregoing that, while particular forms of the disclosure have been illustrated and described, various modifications can be made without parting from the spirit and scope of the disclosure.

We claim:

1. A system for treatment of body tissue, comprising:
 an anchor assembly, the anchor assembly including a first component attached to a connector and a second anchor component; and
 a delivery device, the delivery device including a handle, an elongate portion extending in a proximal to distal direction from the handle, the elongate portion including a leading end, a needle tube, and a scope lumen terminating within the leading end of the elongate portion, a needle assembly extending through the needle tube and configured to be advanced from the leading end, and the connector extending through the needle assembly;
 wherein a terminal end portion of the needle assembly has a start position distal to and within view of the scope lumen and within the leading end of the elongate portion and the needle tube has a distal end that is distal to and within view of the scope lumen.

2. The system of claim 1, wherein the leading end is configured with a guide to constrain the needle assembly to exit the leading end in a generally perpendicular direction with respect to the elongate portion.

3. The system of claim 1, wherein the needle assembly has a start position in a path of the second anchor component.

4. The system of claim 1, wherein the needle has a beveled tip on another side of the needle assembly from that of an inside radius as it is ejected from the delivery device.

5. The system of claim 1, wherein the scope lumen is laterally offset from the needle tube.

6. The system of claim 5, wherein one or more of the scope lumen and needle assembly are configured to be laterally translated.

7. The system of claim 1, further comprising an endoscope configured to be translated axially within the scope lumen.

8. The system of claim 1, further comprising a cover, wherein the cover is positioned between the needle tube and scope lumen.

9. The system of claim 1, wherein a viewing space is provided distal to scope lumen within the elongate portion.

* * * * *